US009198929B2

(12) United States Patent
Watson et al.

(10) Patent No.: US 9,198,929 B2
(45) Date of Patent: Dec. 1, 2015

(54) COMPOSITIONS AND METHODS FOR ENHANCING PHYSIOLOGICAL PERFORMANCE AND RECOVERY TIME

(75) Inventors: Richard L. Watson, McPherson, KS (US); Anthony B. Wood, Dallas, TX (US); Gregory J. Archambeau, Puyallup, WA (US)

(73) Assignee: Revalesio Corporation, Tacoma, WA (US)

( * ) Notice: Subject to any disclaimer, the term of this patent is extended or adjusted under 35 U.S.C. 154(b) by 999 days.

(21) Appl. No.: 13/102,930

(22) Filed: May 6, 2011

(65) Prior Publication Data
US 2012/0039951 A1 Feb. 16, 2012

Related U.S. Application Data

(60) Provisional application No. 61/332,669, filed on May 7, 2010, provisional application No. 61/358,798, filed on Jun. 25, 2010, provisional application No. 61/413,258, filed on Nov. 12, 2010.

(51) Int. Cl.
*A61K 9/14* (2006.01)
*A61K 33/00* (2006.01)
*A23L 1/30* (2006.01)
*A23L 2/54* (2006.01)
*A61K 41/00* (2006.01)

(52) U.S. Cl.
CPC . *A61K 33/00* (2013.01); *A23L 1/30* (2013.01); *A23L 2/54* (2013.01); *A61K 41/0004* (2013.01); *A23V 2002/00* (2013.01)

(58) Field of Classification Search
CPC ......... A23L 1/30; A23L 2/54; A23V 2002/00
USPC .......................................... 424/400; 977/915
See application file for complete search history.

(56) References Cited

U.S. PATENT DOCUMENTS

| | | | |
|---|---|---|---|
| 1,627,161 A | 5/1927 | Edwards |
| 1,650,561 A | 11/1927 | Williams |
| 1,650,612 A | 11/1927 | Deniston |
| 1,711,154 A | 4/1929 | Michal |
| 2,115,123 A | 4/1938 | Russell |
| 2,159,670 A | 5/1939 | Neitzke |
| 2,278,051 A | 3/1942 | Ambrose |
| 2,591,966 A | 4/1952 | Rider |
| 2,606,502 A | 8/1952 | Carlson |
| 2,639,901 A | 5/1953 | Teale |
| 2,688,470 A | 9/1954 | Marco |
| 2,734,728 A | 2/1956 | Myers |
| 2,798,698 A | 7/1957 | Dooley |
| 2,960,318 A | 11/1960 | Caillaud |
| 2,969,960 A | 1/1961 | Gurley |
| 2,970,817 A | 2/1961 | Gurley, Jr. |
| 2,995,346 A | 8/1961 | Samples |
| 3,174,185 A | 3/1965 | Gerber |
| 3,182,975 A | 5/1965 | Stewart |
| 3,194,540 A | 7/1965 | Hager |
| 3,332,631 A | 7/1967 | Wood |
| 3,333,771 A | 8/1967 | Graham |
| 3,333,828 A | 8/1967 | Boehme |
| 3,471,131 A | 10/1969 | Fritzweiler |
| 3,514,079 A | 5/1970 | Little, Jr. |
| 3,630,498 A | 12/1971 | Bielinski |
| 3,653,637 A | 4/1972 | Eckhardt |
| 3,660,933 A | 5/1972 | Wong, Jr. |
| 3,744,763 A | 7/1973 | Schnoring |

(Continued)

FOREIGN PATENT DOCUMENTS

| CN | 1399559 | 2/2003 |
|---|---|---|
| CN | 1499977 | 5/2004 |

(Continued)

OTHER PUBLICATIONS

Piantadpsi; Title: "Oxygenated" water and athletic performance; Br. J. Sports Med., Sep. 2006 issue, vol. 40(9), pp. 740-741, published online Jul. 19, 2006.*
Definition of the word "electrokinetic" Merriam-Webster Online Dictionary.*
Ostroski et al.; Title: Pro- and anti-inflammatory cytokine balance in strenuous exercise in humans; The Journal of Physiology, 515, pp. 287-291, Feb. 15, 1999.*
Cotman et al.; Title: Exercise builds brain healty: key roles of growth factor cascades and inflammation; Trends in neurosciences, vol. 30, No. 9, p. 464-472, published online Aug. 31, 2007.*
Petersen et al.; Title: The anti-inflammatory effect of exercise; J. Appl. Physiol; vol. 98, pp. 1154-1162, 2005.*

(Continued)

*Primary Examiner* — Johann R Richter
*Assistant Examiner* — Yanzhi Zhang
(74) *Attorney, Agent, or Firm* — Barry L. Davison; Davis Wright Tremaine LLP

(57) ABSTRACT

Provided are methods for enhancing exercise (e.g., intense, eccentric, elevated temperature, repetitive, aerobic, and high altitude) performance, comprising administering electrokinetically-altered aqueous fluids comprising an ionic aqueous solution of stably configured charge-stabilized oxygen-containing nanostructures predominantly having an average diameter of less than 100 nanometers. In certain aspects, enhancing exercise performance comprises at least one of: reducing plasma inflammatory cytokines (e.g., IFN-alpha, ENA-78 and BDNF); ameliorating muscle/tendon damage or enhancing muscle/tendon recovery; reducing biomarkers of exercise-induced muscle injury (e.g., CK-, plasma myoglobin); ameliorating exercise induced tendinosis, tendonitis, tenosynovitis, avulsion, and tendon strain associated with chronic repetitive movement or enhancing recovering therefrom; increasing $VO_2$ max; decreasing RPE; reducing blood lactate; preserving muscle contractile function (e.g., maximal force, joint ROM); reducing muscle soreness; ameliorating onset of fatigue in an exercising subject. Improved methods for producing electrokinetically altered aqueous fluids (including sports beverages) are also provided.

7 Claims, 34 Drawing Sheets

(56) References Cited

U.S. PATENT DOCUMENTS

| | | |
|---|---|---|
| 3,791,349 A | 2/1974 | Schaefer |
| 3,925,243 A | 12/1975 | Brogli |
| 3,937,445 A | 2/1976 | Agosta |
| 3,938,783 A | 2/1976 | Porter |
| 3,939,073 A | 2/1976 | Bats |
| 3,980,280 A | 9/1976 | Benson |
| 3,986,709 A | 10/1976 | Vermeulen |
| 3,996,012 A | 12/1976 | Zucker |
| 3,998,433 A | 12/1976 | Iwako |
| 4,004,553 A | 1/1977 | Stenstrom |
| 4,011,027 A | 3/1977 | Selder |
| 4,014,526 A | 3/1977 | Cramer |
| 4,049,240 A | 9/1977 | Walters |
| 4,051,204 A | 9/1977 | Muller |
| 4,057,223 A | 11/1977 | Rosenberger |
| 4,057,933 A | 11/1977 | Enyeart |
| 4,069,147 A | 1/1978 | Abrams |
| 4,071,225 A | 1/1978 | Holl |
| 4,089,507 A | 5/1978 | Arai |
| 4,097,026 A | 6/1978 | Haindl |
| 4,116,164 A | 9/1978 | Shabi |
| 4,117,550 A | 9/1978 | Folland |
| 4,127,332 A | 11/1978 | Thiruvengadam |
| 4,128,342 A | 12/1978 | Renk |
| 4,136,971 A | 1/1979 | Varlamov |
| 4,143,639 A | 3/1979 | Frenette |
| 4,144,167 A | 3/1979 | Burkett |
| 4,159,944 A | 7/1979 | Erickson |
| 4,162,153 A | 7/1979 | Spector |
| 4,163,712 A | 8/1979 | Smith |
| 4,172,668 A | 10/1979 | Thompson |
| 4,175,873 A | 11/1979 | Iwako |
| 4,183,681 A | 1/1980 | Li |
| 4,201,487 A | 5/1980 | Backhaus |
| 4,213,712 A | 7/1980 | Aanonsen |
| 4,261,521 A | 4/1981 | Ashbrook |
| 4,263,003 A | 4/1981 | Vork |
| 4,284,623 A | 8/1981 | Beck |
| 4,289,733 A | 9/1981 | Saito |
| 4,294,549 A | 10/1981 | Thompson |
| 4,316,673 A | 2/1982 | Speer |
| 4,318,429 A | 3/1982 | Gouttebessis |
| 4,332,486 A | 6/1982 | Mutalibov |
| 4,361,414 A | 11/1982 | Nemes |
| 4,368,986 A | 1/1983 | Fischer |
| 4,383,767 A | 5/1983 | Jido |
| 4,388,915 A | 6/1983 | Shafran |
| 4,393,017 A | 7/1983 | Kim |
| 4,394,966 A | 7/1983 | Snyder |
| 4,408,890 A | 10/1983 | Beckmann |
| 4,416,548 A | 11/1983 | Carre |
| 4,424,797 A | 1/1984 | Perkins |
| 4,436,430 A | 3/1984 | Mayer |
| 4,441,823 A | 4/1984 | Power |
| 4,444,510 A | 4/1984 | Janssen |
| 4,469,595 A | 9/1984 | Napadow |
| 4,474,479 A | 10/1984 | Redelman |
| 4,477,338 A | 10/1984 | Hellmann |
| 4,507,285 A | 3/1985 | Kuhne |
| 4,509,861 A | 4/1985 | Sjonell |
| 4,533,254 A | 8/1985 | Cook |
| 4,539,139 A | 9/1985 | Ichikawa |
| 4,550,022 A | 10/1985 | Garabedian |
| 4,594,228 A | 6/1986 | Lambert |
| 4,619,072 A | 10/1986 | Privett |
| 4,633,909 A | 1/1987 | Louboutin |
| 4,634,675 A | 1/1987 | Freedman |
| 4,645,606 A | 2/1987 | Ashbrook |
| 4,661,243 A | 4/1987 | Hotz |
| 4,663,055 A | 5/1987 | Ling |
| 4,664,680 A | 5/1987 | Weber |
| 4,684,614 A | 8/1987 | Krovak |
| 4,687,579 A | 8/1987 | Bergman |
| 4,696,283 A | 9/1987 | Kohlmetz |
| 4,715,274 A | 12/1987 | Paoletti |
| 4,733,972 A | 3/1988 | Weis |
| 4,735,133 A | 4/1988 | Paoletti |
| 4,749,493 A | 6/1988 | Hicks |
| 4,753,535 A | 6/1988 | King |
| 4,764,283 A | 8/1988 | Ashbrook |
| 4,765,807 A | 8/1988 | Henriksen |
| 4,778,336 A | 10/1988 | Husain |
| 4,793,247 A | 12/1988 | Verweij |
| 4,798,176 A | 1/1989 | Perkins |
| 4,808,007 A | 2/1989 | King |
| 4,820,381 A | 4/1989 | Brown |
| 4,834,545 A | 5/1989 | Inoue |
| 4,838,699 A | 6/1989 | Jour |
| 4,880,445 A | 11/1989 | Watten |
| 4,884,892 A | 12/1989 | Gust |
| 4,886,368 A | 12/1989 | King |
| 4,906,574 A | 3/1990 | Erdei |
| 4,908,101 A | 3/1990 | Frisk |
| 4,937,004 A | 6/1990 | Mandrin |
| 4,957,626 A | 9/1990 | Ashbrook |
| 4,972,801 A | 11/1990 | Hunt |
| 4,973,168 A | 11/1990 | Chan |
| 4,976,547 A | 12/1990 | Hisanaga |
| 4,999,015 A | 3/1991 | DeMaris |
| 5,005,982 A | 4/1991 | Kistner |
| 5,006,352 A | 4/1991 | Zelenak nee Zoltai et al. |
| 5,011,372 A | 4/1991 | Nigrelli et al. |
| 5,024,647 A | 6/1991 | Jubin |
| 5,052,813 A | 10/1991 | Latto |
| 5,075,234 A | 12/1991 | Tunac |
| 5,141,328 A | 8/1992 | Dilley |
| 5,152,212 A | 10/1992 | Chauveau |
| 5,176,447 A | 1/1993 | Bata |
| 5,185,081 A | 2/1993 | Nyman |
| 5,188,090 A | 2/1993 | Griggs |
| 5,205,647 A | 4/1993 | Ricciardi |
| 5,263,774 A | 11/1993 | Delcourt |
| 5,275,486 A | 1/1994 | Fissenko |
| 5,279,262 A | 1/1994 | Muehleck |
| 5,279,463 A | 1/1994 | Holl |
| 5,281,341 A | 1/1994 | Reimers |
| 5,304,001 A | 4/1994 | Kuo |
| 5,318,702 A | 6/1994 | Ashbrook |
| 5,326,484 A | 7/1994 | Nakashima |
| 5,341,692 A | 8/1994 | Sher et al. |
| 5,341,768 A | 8/1994 | Pope |
| 5,366,288 A | 11/1994 | Dahllof |
| 5,370,824 A | 12/1994 | Nagano |
| 5,372,424 A | 12/1994 | Lecouturier |
| 5,372,824 A | 12/1994 | Record et al. |
| 5,378,321 A | 1/1995 | Delcourt |
| 5,380,089 A | 1/1995 | Karasawa |
| 5,380,471 A | 1/1995 | Ban |
| 5,403,089 A | 4/1995 | Kuo |
| 5,407,637 A | 4/1995 | Gibboney |
| 5,419,306 A | 5/1995 | Huffman |
| 5,435,913 A | 7/1995 | Ashbrook |
| 5,450,368 A | 9/1995 | Kubota |
| 5,470,153 A | 11/1995 | De Naeghel |
| 5,474,380 A | 12/1995 | Sukup |
| 5,482,369 A | 1/1996 | Verstallen |
| 5,496,108 A | 3/1996 | Sukup |
| 5,511,877 A | 4/1996 | King |
| 5,538,191 A | 7/1996 | Holl |
| 5,538,343 A | 7/1996 | Tynan |
| 5,551,859 A | 9/1996 | Cantrill |
| 5,552,133 A | 9/1996 | Lambert |
| 5,556,765 A | 9/1996 | Dedolph |
| 5,560,710 A | 10/1996 | Klocke |
| 5,561,944 A | 10/1996 | Ismail |
| 5,563,189 A | 10/1996 | Hosokawa |
| 5,569,416 A | 10/1996 | Cross |
| 5,575,559 A | 11/1996 | Roll |
| 5,590,961 A | 1/1997 | Rasmussen |
| 5,616,304 A | 4/1997 | Stormo |
| 5,630,909 A | 5/1997 | LaRiviere |
| 5,658,380 A | 8/1997 | Dillenbeck |
| 5,665,228 A | 9/1997 | Leaverton et al. |
| 5,671,664 A | 9/1997 | Jacobson |

(56) References Cited

U.S. PATENT DOCUMENTS

| | | |
|---|---|---|
| 5,674,312 A | 10/1997 | Mazzei |
| 5,697,187 A | 12/1997 | Persinger |
| 5,711,887 A | 1/1998 | Gastman et al. |
| 5,711,950 A | 1/1998 | Lorenzen |
| 5,720,551 A | 2/1998 | Shechter |
| 5,744,105 A | 4/1998 | Stormo |
| 5,766,490 A | 6/1998 | Taylor |
| 5,770,062 A | 6/1998 | Isbell |
| 5,779,996 A | 7/1998 | Stormo |
| 5,782,556 A | 7/1998 | Chu |
| 5,791,778 A | 8/1998 | Manninen |
| 5,810,052 A | 9/1998 | Kozyuk |
| 5,810,474 A | 9/1998 | Hidalgo |
| 5,813,758 A | 9/1998 | Delcourt |
| 5,814,222 A | 9/1998 | Zelenak |
| 5,823,671 A | 10/1998 | Mitchell |
| 5,845,993 A | 12/1998 | Shirtum |
| 5,851,068 A | 12/1998 | Rumph |
| 5,863,120 A | 1/1999 | Gallagher et al. |
| 5,865,537 A | 2/1999 | Streiff |
| 5,868,495 A | 2/1999 | Hidalgo |
| 5,868,944 A | 2/1999 | Wright |
| 5,885,467 A | 3/1999 | Zelenak |
| 5,887,383 A | 3/1999 | Soeda |
| 5,893,337 A | 4/1999 | Sevic |
| 5,902,042 A | 5/1999 | Imaizumi |
| 5,904,851 A | 5/1999 | Taylor |
| 5,918,976 A | 7/1999 | Hashimoto |
| 5,921,678 A | 7/1999 | Desai |
| 5,921,679 A | 7/1999 | Muzzio |
| 5,925,292 A | 7/1999 | Ziesenis |
| 5,931,771 A | 8/1999 | Kozyuk |
| 5,938,581 A | 8/1999 | Bibette |
| 5,948,326 A | 9/1999 | Pate |
| 5,951,922 A | 9/1999 | Mazzei |
| 5,957,122 A | 9/1999 | Griggs |
| 5,971,601 A | 10/1999 | Kozyuk |
| 5,993,752 A | 11/1999 | Kobayashi |
| 5,997,717 A | 12/1999 | Miyashita et al. |
| 6,000,840 A | 12/1999 | Paterson |
| 6,017,447 A | 1/2000 | Wright |
| 6,019,499 A | 2/2000 | Selivanov |
| 6,042,792 A | 3/2000 | Shefer |
| 6,086,243 A | 7/2000 | Paul |
| 6,092,921 A | 7/2000 | Wentinck |
| 6,096,221 A | 8/2000 | Kerchouche |
| 6,110,353 A | 8/2000 | Hough |
| 6,120,008 A | 9/2000 | Littman |
| 6,120,668 A | 9/2000 | Kim |
| 6,135,628 A | 10/2000 | DeStefano |
| 6,153,607 A | 11/2000 | Pflugfelder et al. |
| 6,173,526 B1 | 1/2001 | Mazzei |
| 6,180,059 B1 | 1/2001 | Divino |
| 6,190,549 B1 | 2/2001 | Schwartz |
| 6,193,786 B1 | 2/2001 | Henderson |
| 6,210,030 B1 | 4/2001 | Ibar |
| 6,228,259 B1 | 5/2001 | Schwartz |
| 6,234,206 B1 | 5/2001 | Malmberg |
| 6,238,645 B1 | 5/2001 | Spears |
| 6,238,706 B1 | 5/2001 | Sonnenschein |
| 6,241,802 B1 | 6/2001 | Spears |
| 6,250,609 B1 | 6/2001 | Cheng |
| 6,257,754 B1 | 7/2001 | Sondergaard |
| 6,276,825 B2 | 8/2001 | Running |
| 6,279,611 B2 | 8/2001 | Uematsu |
| 6,279,882 B1 | 8/2001 | Littman |
| 6,284,293 B1 | 9/2001 | Crandall |
| 6,290,857 B1 | 9/2001 | Brahmbhatt |
| 6,294,212 B1 | 9/2001 | Huber |
| 6,299,343 B1 | 10/2001 | Pekerman |
| 6,312,647 B1 | 11/2001 | Spears |
| 6,315,942 B1 | 11/2001 | Spears |
| 6,332,706 B1 | 12/2001 | Hall |
| 6,338,569 B1 | 1/2002 | McGill |
| 6,344,489 B1 | 2/2002 | Spears |
| 6,366,751 B1 | 4/2002 | Shakuto et al. |
| 6,367,783 B1 | 4/2002 | Raftis |
| 6,380,264 B1 | 4/2002 | Jameson |
| 6,382,601 B1 | 5/2002 | Ohnari |
| 6,386,751 B1 | 5/2002 | Wootan et al. |
| 6,398,402 B1 | 6/2002 | Thomas |
| 6,402,361 B1 | 6/2002 | Reinemuth |
| 6,412,714 B1 | 7/2002 | Witsken |
| 6,413,418 B2 | 7/2002 | Brahmbhatt |
| 6,431,742 B2 | 8/2002 | Mori |
| 6,443,610 B1 | 9/2002 | Shechter |
| 6,451,328 B1 | 9/2002 | Ionita-Manzatu et al. |
| 6,454,997 B1 | 9/2002 | Divino |
| 6,458,071 B1 | 10/2002 | Jacobson |
| 6,474,264 B1 | 11/2002 | Grimberg |
| 6,474,862 B2 | 11/2002 | Farrell |
| 6,481,649 B1 | 11/2002 | Schmidt |
| 6,485,003 B2 | 11/2002 | Speece |
| 6,488,401 B1 | 12/2002 | Seaman |
| 6,488,765 B1 | 12/2002 | Tseng |
| 6,494,055 B1 | 12/2002 | Meserole |
| 6,499,671 B1 | 12/2002 | Sands et al. |
| 6,521,248 B1 | 2/2003 | Holloway |
| 6,524,475 B1 | 2/2003 | Herrington |
| 6,530,895 B1 | 3/2003 | Keirn |
| 6,538,041 B1 | 3/2003 | Marelli |
| 6,540,436 B2 | 4/2003 | Ogi |
| 6,551,492 B2 | 4/2003 | Hanaoka |
| 6,557,492 B1 | 5/2003 | Robohm |
| 6,576,130 B2 | 6/2003 | Wallace |
| 6,582,387 B2 | 6/2003 | Derek |
| 6,586,441 B2 | 7/2003 | Borroni et al. |
| 6,596,235 B2 | 7/2003 | Divino |
| 6,602,468 B2 | 8/2003 | Patterson |
| 6,613,280 B2 | 9/2003 | Myrick |
| 6,619,399 B1 | 9/2003 | Chatterji |
| 6,627,784 B2 | 9/2003 | Hudson et al. |
| 6,632,014 B2 | 10/2003 | Steinberg |
| 6,649,145 B2 | 11/2003 | McGrath |
| 6,655,830 B1 | 12/2003 | Seaman |
| 6,669,966 B1 | 12/2003 | Antelman |
| 6,676,900 B1 | 1/2004 | Divino |
| 6,682,215 B2 | 1/2004 | Kinsley |
| 6,682,732 B1 | 1/2004 | Blake et al. |
| 6,688,883 B2 | 2/2004 | Tseng |
| 6,689,262 B2 | 2/2004 | Senkiw |
| 6,702,949 B2 | 3/2004 | Wood |
| 6,705,755 B1 | 3/2004 | Innings |
| 6,730,211 B2 | 5/2004 | Hanaoka |
| 6,733,172 B2 | 5/2004 | Lee |
| 6,749,329 B2 | 6/2004 | Shechter |
| 6,752,529 B2 | 6/2004 | Holl |
| 6,764,213 B2 | 7/2004 | Shechter |
| 6,782,924 B2 | 8/2004 | Daoud |
| 6,796,702 B2 | 9/2004 | Wire |
| 6,821,438 B2 | 11/2004 | Hadley |
| 6,837,986 B2 | 1/2005 | Hanaoka |
| 6,857,774 B2 | 2/2005 | Kozyuk |
| 6,869,212 B2 | 3/2005 | Uesugi |
| 6,905,523 B2 | 6/2005 | Vainshelboim |
| 6,910,448 B2 | 6/2005 | Thoma |
| 6,935,768 B2 | 8/2005 | Lowe |
| 6,935,770 B2 | 8/2005 | Schueler |
| 6,936,179 B2 | 8/2005 | DeWald |
| 6,936,221 B1 | 8/2005 | Divino |
| 6,955,713 B2 | 10/2005 | Rittner |
| 6,958,163 B2 | 10/2005 | Ionita-Manzatu et al. |
| 6,959,669 B2 | 11/2005 | Thoma |
| 6,974,546 B2 | 12/2005 | Wood |
| 7,008,535 B1 | 3/2006 | Spears |
| 7,037,842 B2 | 5/2006 | Verhaverbeke |
| 7,069,073 B2 | 6/2006 | Henley et al. |
| 7,089,886 B2 | 8/2006 | Thoma |
| 7,090,753 B2 | 8/2006 | Sumita |
| 7,121,714 B2 | 10/2006 | Metcalfe |
| 7,128,278 B2 | 10/2006 | Archambeau et al. |
| 7,137,620 B2 | 11/2006 | Thomas |
| 7,137,621 B1 | 11/2006 | Bagley |
| 7,179,375 B2 | 2/2007 | Wood |

(56) References Cited

U.S. PATENT DOCUMENTS

| | | |
|---|---|---|
| 7,198,254 B2 | 4/2007 | Holloway et al. |
| 7,201,225 B2 | 4/2007 | Smith |
| 7,223,246 B2 | 5/2007 | Don |
| 7,237,943 B2 | 7/2007 | Brown |
| 7,241,723 B2 | 7/2007 | Zhang et al. |
| 7,243,910 B2 | 7/2007 | Bagley |
| 7,255,881 B2 | 8/2007 | Gillis et al. |
| 7,316,501 B2 | 1/2008 | Thoma |
| 7,334,781 B2 | 2/2008 | Donnelly |
| 7,347,944 B2 | 3/2008 | Bagley |
| 7,360,755 B2 | 4/2008 | Hudson |
| 7,387,262 B2 | 6/2008 | Thoma |
| 7,396,441 B2 | 7/2008 | Senkiw |
| 7,544,365 B2 | 6/2009 | Dosch et al. |
| 7,654,728 B2 | 2/2010 | Wood et al. |
| 7,690,833 B2 | 4/2010 | Metcalfe |
| 7,731,953 B2 | 6/2010 | Leonard |
| 7,749,692 B2 | 7/2010 | Mano |
| 7,770,814 B2 | 8/2010 | Archambeau |
| 7,806,584 B2 | 10/2010 | Wood et al. |
| 7,832,920 B2 | 11/2010 | Wood et al. |
| 7,887,698 B2 | 2/2011 | Wood |
| 7,919,534 B2 | 4/2011 | Wood et al. |
| 8,349,191 B2 | 1/2013 | Wood |
| 8,410,182 B2 | 4/2013 | Wood et al. |
| 8,445,546 B2 | 5/2013 | Wood et al. |
| 8,449,172 B2 | 5/2013 | Wood et al. |
| 8,470,893 B2 | 6/2013 | Wood et al. |
| 2001/0003291 A1 | 6/2001 | Uematsu et al. |
| 2001/0022755 A1 | 9/2001 | Holtzapple |
| 2001/0031740 A1 | 10/2001 | Unger et al. |
| 2001/0040134 A1 | 11/2001 | Brahmbhatt et al. |
| 2002/0045742 A1 | 4/2002 | Jones et al. |
| 2002/0136662 A1 | 9/2002 | Myrick et al. |
| 2002/0138034 A1 | 9/2002 | Derek et al. |
| 2002/0164379 A1 | 11/2002 | Nishihara |
| 2002/0184820 A1 | 12/2002 | Mauney |
| 2002/0187203 A1 | 12/2002 | Cioca et al. |
| 2002/0196702 A1 | 12/2002 | Shechter |
| 2003/0017001 A1 | 1/2003 | Ogi |
| 2003/0022288 A1 | 1/2003 | Zuker et al. |
| 2003/0042174 A1 | 3/2003 | Austin |
| 2003/0056805 A1 | 3/2003 | Sumita |
| 2003/0057163 A1 | 3/2003 | Wood |
| 2003/0072212 A1 | 4/2003 | Wood et al. |
| 2003/0083610 A1 | 5/2003 | McGrath et al. |
| 2003/0147303 A1 | 8/2003 | Schueler |
| 2003/0188740 A1 | 10/2003 | Tribelsky |
| 2003/0199089 A1 | 10/2003 | Surber et al. |
| 2003/0232114 A1 | 12/2003 | Dekleva |
| 2004/0004042 A1 | 1/2004 | Hadley et al. |
| 2004/0019319 A1 | 1/2004 | Derek et al. |
| 2004/0022122 A1 | 2/2004 | Kozyuk |
| 2004/0027915 A1 | 2/2004 | Lowe |
| 2004/0058010 A1 | 3/2004 | Holloway, Jr. et al. |
| 2004/0060446 A1 | 4/2004 | Rittner |
| 2004/0089746 A1 | 5/2004 | Archambeau |
| 2004/0090862 A1 | 5/2004 | Uesugi |
| 2004/0118701 A1 | 6/2004 | Senkiw |
| 2004/0126468 A1 | 7/2004 | Holloway, Jr. et al. |
| 2004/0129112 A1 | 7/2004 | Gillis et al. |
| 2004/0142377 A1 | 7/2004 | Unett et al. |
| 2004/0166171 A1 | 8/2004 | McGrath et al. |
| 2004/0222106 A1 | 11/2004 | Hough |
| 2004/0235732 A1 | 11/2004 | Zhou et al. |
| 2004/0241154 A1 | 12/2004 | Davis et al. |
| 2004/0245186 A1 | 12/2004 | Wood |
| 2004/0248909 A1 | 12/2004 | Sun et al. |
| 2004/0258687 A1 | 12/2004 | Waldman et al. |
| 2004/0266693 A1 | 12/2004 | Ruben et al. |
| 2005/0047270 A1 | 3/2005 | Wood et al. |
| 2005/0048034 A1 | 3/2005 | Fraser et al. |
| 2005/0096458 A1 | 5/2005 | Edwards et al. |
| 2005/0139808 A1 | 6/2005 | Alimi |
| 2005/0142157 A1 | 6/2005 | Alimi |
| 2005/0196370 A1 | 9/2005 | Yu et al. |
| 2005/0196462 A1 | 9/2005 | Alimi |
| 2005/0249712 A1 | 11/2005 | Leonard et al. |
| 2005/0259510 A1 | 11/2005 | Thoma |
| 2005/0263607 A1 | 12/2005 | Thoma |
| 2005/0273018 A1 | 12/2005 | Don |
| 2006/0030900 A1 | 2/2006 | Eckert |
| 2006/0039902 A1 | 2/2006 | Young et al. |
| 2006/0039910 A1 | 2/2006 | Comeau et al. |
| 2006/0045796 A1 | 3/2006 | Anderle et al. |
| 2006/0054205 A1 | 3/2006 | Yabe et al. |
| 2006/0098528 A1 | 5/2006 | Wood |
| 2006/0116419 A1 | 6/2006 | Callahan et al. |
| 2006/0135585 A1 | 6/2006 | Day et al. |
| 2006/0146644 A1 | 7/2006 | Holloway et al. |
| 2006/0150491 A1 | 7/2006 | Senkiw |
| 2006/0198822 A1 | 9/2006 | Booth et al. |
| 2006/0198901 A9 | 9/2006 | Holloway, Jr. |
| 2006/0204458 A1 | 9/2006 | Holloway, Jr. et al. |
| 2006/0210613 A1 | 9/2006 | Carliss |
| 2006/0216360 A1 | 9/2006 | Upadhyay et al. |
| 2006/0235350 A1 | 10/2006 | Alimi |
| 2006/0241546 A1 | 10/2006 | Alimi |
| 2006/0253060 A1 | 11/2006 | Alimi |
| 2006/0272947 A1 | 12/2006 | Bagley |
| 2006/0272954 A1 | 12/2006 | Sumita |
| 2006/0273018 A1 | 12/2006 | Bagley |
| 2006/0273021 A1 | 12/2006 | Bagley |
| 2006/0273029 A1 | 12/2006 | Bagley |
| 2006/0273281 A1 | 12/2006 | Bagley |
| 2006/0273282 A1 | 12/2006 | Bagley |
| 2006/0273475 A1 | 12/2006 | Bagley |
| 2006/0275423 A1 | 12/2006 | Bagley |
| 2006/0292240 A1 | 12/2006 | Bagley |
| 2006/0292241 A1 | 12/2006 | Bagley |
| 2007/0003497 A1 | 1/2007 | Holloway, Jr. et al. |
| 2007/0021331 A1 | 1/2007 | Fraser et al. |
| 2007/0077553 A1 | 4/2007 | Bentwich |
| 2007/0141163 A1 | 6/2007 | Vitaliano et al. |
| 2007/0173460 A1 | 7/2007 | Alimi |
| 2007/0173755 A1 | 7/2007 | Alimi |
| 2007/0189972 A1 | 8/2007 | Chiba et al. |
| 2007/0196357 A1 | 8/2007 | Alimi |
| 2007/0196434 A1 | 8/2007 | Alimi |
| 2007/0205161 A1 | 9/2007 | Chiba et al. |
| 2007/0210180 A1 | 9/2007 | Archambeau et al. |
| 2007/0237787 A1 | 10/2007 | Leonard et al. |
| 2007/0259032 A1 | 11/2007 | Bright et al. |
| 2007/0286795 A1 | 12/2007 | Chiba et al. |
| 2007/0287917 A1 | 12/2007 | Takahashi et al. |
| 2008/0050452 A1 | 2/2008 | Chen et al. |
| 2008/0057486 A1 | 3/2008 | Mano et al. |
| 2008/0063720 A1 | 3/2008 | Gounko et al. |
| 2008/0139674 A1 | 6/2008 | Archambeau et al. |
| 2008/0146679 A1 | 6/2008 | Archambeau et al. |
| 2008/0153795 A1 | 6/2008 | Occleston |
| 2008/0161541 A1 | 7/2008 | Lazar et al. |
| 2008/0206356 A1 | 8/2008 | Guinovart Cirera et al. |
| 2008/0219088 A1 | 9/2008 | Wood et al. |
| 2008/0220089 A1 | 9/2008 | Hojo et al. |
| 2008/0241098 A1 | 10/2008 | Young et al. |
| 2008/0281001 A1 | 11/2008 | Wood et al. |
| 2009/0082264 A1 | 3/2009 | Fischer et al. |
| 2009/0208473 A1 | 8/2009 | Weisleder et al. |
| 2009/0227018 A1 | 9/2009 | Watson et al. |
| 2009/0247458 A1 | 10/2009 | Watson et al. |
| 2009/0263495 A1 | 10/2009 | Watson et al. |
| 2009/0274730 A1 | 11/2009 | Watson et al. |
| 2009/0274771 A1 | 11/2009 | Watson et al. |
| 2010/0003333 A1 | 1/2010 | Watson et al. |
| 2010/0004189 A1 | 1/2010 | Watson et al. |
| 2010/0008997 A1 | 1/2010 | Watson et al. |
| 2010/0009008 A1 | 1/2010 | Watson et al. |
| 2010/0015235 A1 | 1/2010 | Watson et al. |
| 2010/0021464 A1 | 1/2010 | Archambeau et al. |
| 2010/0028441 A1 | 2/2010 | Watson et al. |
| 2010/0028442 A1 | 2/2010 | Archambeau et al. |
| 2010/0028443 A1 | 2/2010 | Watson et al. |
| 2010/0029764 A1 | 2/2010 | Watson et al. |

(56) References Cited

U.S. PATENT DOCUMENTS

| | | |
|---|---|---|
| 2010/0038244 A1 | 2/2010 | Wood et al. |
| 2010/0098659 A1 | 4/2010 | Watson |
| 2010/0098687 A1 | 4/2010 | Watson |
| 2010/0166784 A1 | 7/2010 | Murphy et al. |
| 2010/0186680 A1 | 7/2010 | Matsumura et al. |
| 2010/0252492 A1 | 10/2010 | Wood |
| 2010/0297193 A1 | 11/2010 | Archambeau et al. |
| 2010/0303871 A1 | 12/2010 | Watson et al. |
| 2010/0303917 A1 | 12/2010 | Watson et al. |
| 2010/0303918 A1 | 12/2010 | Watson et al. |
| 2010/0310609 A1 | 12/2010 | Watson et al. |
| 2010/0310664 A1 | 12/2010 | Watson |
| 2010/0310665 A1 | 12/2010 | Watson |
| 2010/0311167 A1 | 12/2010 | Wood et al. |
| 2010/0316723 A1 | 12/2010 | Watson et al. |
| 2010/0323383 A1 | 12/2010 | Manel et al. |
| 2011/0008462 A1 | 1/2011 | Wood et al. |
| 2011/0075507 A1 | 3/2011 | Wootan et al. |
| 2011/0081384 A1 | 4/2011 | Archambeau et al. |
| 2011/0104804 A1 | 5/2011 | Wood et al. |
| 2011/0165172 A1 | 7/2011 | Yarranton |
| 2011/0245107 A1 | 10/2011 | Kuchroo et al. |
| 2012/0015083 A1 | 1/2012 | Wood |
| 2012/0034696 A1 | 2/2012 | Wood |
| 2012/0039884 A1 | 2/2012 | Watson |
| 2012/0039951 A1 | 2/2012 | Watson |
| 2012/0039958 A1 | 2/2012 | Watson |
| 2012/0114702 A1 | 5/2012 | Watson |
| 2012/0121656 A1 | 5/2012 | Watson |
| 2012/0263764 A1 | 10/2012 | Watson |
| 2013/0092368 A1 | 4/2013 | Wood |
| 2013/0252323 A1 | 9/2013 | Wood et al. |
| 2013/0260462 A1 | 10/2013 | Wood et al. |
| 2013/0270478 A1 | 10/2013 | Wood et al. |
| 2013/0295144 A1 | 11/2013 | Wood et al. |

FOREIGN PATENT DOCUMENTS

| | | |
|---|---|---|
| CN | 101237875 | 8/2008 |
| DE | 1557171 | 7/1970 |
| DE | 3123743 | 3/1982 |
| DE | 3436049 | 4/1986 |
| DE | 4008676 | 9/1991 |
| DE | 4317078 | 11/1994 |
| DE | 10105118 | 8/2002 |
| DE | 10227818 | 8/2004 |
| EP | 0363009 | 4/1990 |
| EP | 0555498 | 8/1993 |
| EP | 0682000 | 11/1995 |
| EP | 0880993 | 12/1998 |
| EP | 1201296 | 10/2001 |
| EP | 1797869 | 6/2007 |
| GB | 1279736 | 6/1972 |
| JP | 53-146264 | 12/1978 |
| JP | 56-161893 | 12/1981 |
| JP | 2001171627 | 7/1989 |
| JP | 2003169332 | 7/1991 |
| JP | 2004290531 | 10/1992 |
| JP | 5096470 | 4/1993 |
| JP | 6114254 | 4/1994 |
| JP | 06262050 | 9/1994 |
| JP | 07-327547 | 12/1995 |
| JP | 8198969 | 8/1996 |
| JP | 9122465 | 5/1997 |
| JP | 11507874 | 7/1999 |
| JP | 2000271590 | 10/2000 |
| JP | 2003-144887 | 5/2003 |
| JP | 2003-520820 | 7/2003 |
| JP | 2003340938 | 9/2003 |
| JP | 2003334548 | 11/2003 |
| JP | 2004074131 | 3/2004 |
| JP | 2004121962 | 4/2004 |
| JP | 2004529090 | 9/2004 |
| JP | 2005110552 | 4/2005 |
| JP | 2005-523147 | 8/2005 |
| JP | 2005245817 | 9/2005 |
| JP | 2005246293 | 9/2005 |
| JP | 2005246294 | 9/2005 |
| JP | 2006223239 | 8/2006 |
| JP | 2006-273730 | 10/2006 |
| JP | 2007275089 | 10/2007 |
| JP | 2008063258 | 3/2008 |
| JP | 2008093611 | 4/2008 |
| JP | 2008093612 | 4/2008 |
| JP | 2008155320 | 7/2008 |
| JP | 2008237950 | 10/2008 |
| JP | 2008259456 | 10/2008 |
| JP | 2009039600 | 2/2009 |
| JP | 2010508088 | 3/2010 |
| NO | 152733 | 8/1985 |
| RU | 2091151 | 9/1997 |
| RU | 2131761 | 6/1999 |
| RU | 2165787 | 4/2001 |
| RU | 2166987 | 5/2001 |
| RU | 2284853 | 4/2005 |
| SU | 127999 | 1/1960 |
| SU | 162461 | 12/1961 |
| SU | 280441 | 11/1970 |
| SU | 495099 | 12/1975 |
| SU | 495862 | 12/1976 |
| SU | 889078 | 12/1981 |
| SU | 921611 | 4/1982 |
| SU | 1281290 | 1/1987 |
| SU | 1337098 | 9/1987 |
| SU | 1584990 | 8/1990 |
| SU | 1706683 | 1/1992 |
| SU | 1768269 | 10/1992 |
| SU | 1773469 | 11/1992 |
| SU | 1820861 | 6/1993 |
| WF | WO2006/029385 | 3/2006 |
| WO | WO 92/05792 | 4/1992 |
| WO | WO95/35501 | 12/1995 |
| WO | WO96/23977 | 8/1996 |
| WO | WO97/27146 | 7/1997 |
| WO | WO98/30319 | 7/1998 |
| WO | WO99/16539 | 4/1999 |
| WO | WO00/02651 | 1/2000 |
| WO | WO00/20109 | 4/2000 |
| WO | WO 01/54704 | 8/2001 |
| WO | WO01/87471 | 11/2001 |
| WO | WO02/24222 | 3/2002 |
| WO | WO02/35234 | 5/2002 |
| WO | WO02/38510 | 5/2002 |
| WO | WO02/060458 | 8/2002 |
| WO | WO02/062455 | 8/2002 |
| WO | WO03/044430 | 5/2003 |
| WO | WO03/089123 | 11/2003 |
| WO | WO2004/013049 | 2/2004 |
| WO | WO2004/016344 | 2/2004 |
| WO | WO2004/022098 | 3/2004 |
| WO | WO 2004/112649 | 12/2004 |
| WO | WO2005/007142 | 1/2005 |
| WO | WO2005/030649 | 4/2005 |
| WO | WO2005/032243 | 4/2005 |
| WO | WO2005/084718 | 9/2005 |
| WO | WO2005/084786 | 9/2005 |
| WO | WO2005/085141 | 9/2005 |
| WO | WO2005/113026 | 12/2005 |
| WO | WO 2006/088210 | 8/2006 |
| WO | WO2006/133113 | 12/2006 |
| WO | WO2007/096149 | 8/2007 |
| WO | WO2008/018932 | 2/2008 |
| WO | WO2008/052143 | 5/2008 |
| WO | WO2008/052145 | 5/2008 |
| WO | WO2008/115290 | 9/2008 |
| WO | WO2009/055614 | 4/2009 |
| WO | WO2009/055620 | 4/2009 |
| WO | WO2009/055729 | 4/2009 |
| WO | WO2009/055824 | 4/2009 |
| WO | WO2009/134728 | 11/2009 |

(56) References Cited

FOREIGN PATENT DOCUMENTS

WO WO2010/048425 4/2010
WO WO2010/048455 4/2010

OTHER PUBLICATIONS

Baird et al.; Title: Creatine-kinase- and exercise-rlated muscle damage implications for muscle performance and recovery; Journal of Nutrition and Metabolism, vol. 2012, p. 1-13, Sep. 2011.*
Valmori, Danila et al., "Human ROR•t+ TH17 cells preferentially differentiate from naive FOXP3+Treg in the presence of lineage-specific polarizing factors," Proc. Natl. Acad. Sci. 107(45) 19402-19407, Nov. 9, 2010.
Auclair et al., "Revisiting the Mechanism of P450 Enzymes with the Radical Clocks Norcarane and Spiro[2,5]octane," Journal of the American Chemical Society 124(21):6020-6027, 2002.
Austin et al., "The Non-Heme Diiron Alkane Monooxygenase of Pseudomonas oleovorans (AlkB) Hydroxylates via a Substrate Radical Intermediate," Journal of the American Chemical Society 122:11747-11748, 2000.
Austin et al., "Xylene monooxygenase, a membrane-spanning non-heme diiron enzyme that hydroxylates hydrocarbons via a substrate radical intermediate," Journal of Inorganic Chemistry, 8:733-740, 2003.
Barnes et al., "How Do Corticosteroids Work in Asthma?," Annals of Internal Medicine, 139:359-370, 2003.
Billington et al., "Signaling and regulation of G Protein-coupled receptors in airway smooth muscle," Respiratory Research 4(2):1-23, 2003.
Bonanno, "Corneal Metabolic Activity in Humans: Corneal Oxygen Consumption," Indiana University School of Optometry Faculty Research, http://www.opt.indiana.edu/people/faculty/bonanno/oxygen.htm, 4 pages, Apr. 9, 2003.
Bragg et al., "Hydrated Electron Dynamics: From Clusters to Bulk," Science Magazine 360(5696):669-671, Sep. 16, 2004.
Brazeau et al., "Intermediate Q from Soluble Methane Monooxygenase Hydroxylates the Mechanistic Substrate Probe Norcarane: Evidence for a Stepwise Reaction," Journal of the American Chemical Society, 123(48):11831-11837, Dec. 5, 2001.
Bucy et al., "Initial increase in blood CD4+ lymphocytes after HIV antiretroviral therapy reflects redistribution from lymphoid tissues," The Journal of Clinical Investigation 103(10):1391-1398, 1999.
Bunkin et al., "Existence of charged submicrobubble clusters in polar liquids as revealed by correlation between optical cavitation and electrical conductivity," Colloids and Surfaces A: Physiochemical and Engineering Aspects 110:207-212, 1996.
Campbell et al., "Redox Modulation of L-type Calcium Channels in Ferret Ventricular Myocytes," J. Gen. Physiol, 108:277-293, Abstract, Oct. 1996.
Cavitation Generator, English Translation of SU495099, published Dec. 15, 1975, 5 pages.
Chaplin, "Declustered Water, Anomalous Water and Crystals," London South Bank University, http://lsbu.ac.uk/water/anmlous.html, 4 pages, retrieved Jul. 10, 2006.
De Angelis et al., "Electronic Structure and Reactivity of Isomeric Oxo-Mn(V) Porphyrins: Effects of Spin-State Crossing and pKa Modulation," Inorganic Chemistry 45(10):4268-4276, Feb. 22, 2006.
Faul, "Sonochemistry—General Overview," Pollution Research Group, http://www.und.ac.za/prg/sonochem/ultragen.html, 2 pages, Nov. 21, 2002.
Florusse et al., "Stable Low-Pressure Hydrogen Clusters Stored in a Binary Clathrate Hydrate," Science Magazine 306:469-471, Oct. 15, 2004.
Forney et al., "Fast Competitive Reactions in Tyalor-Couette Flow," Ind. Eng. Chem. Res. 44(19):7306-7312, 2005.
Frauenfelder et al., "The role of structure, energy landscape, dynamics, and allostery in the enzymatic function of myoglobin," Proceedings of the National Academy of Sciences 98(5):2370-2374, Feb. 27, 2001.
Gill et al., "Nanoparticles: Characteristics, mechanisms of action, and toxicity in pulmonary drug delivery—a review," Journal of Biomedical Nanotechnology 3(2):107-119, 2007.
Gomes et al., "Calcium Channel Blocker Prevents T Helper Type 2 Cell-mediated Airway Inflammation," American Journal of Respiratory and Critical Care Medicine 175:1117-1124, 2007.
Gosens et al., "Muscarinic receptor signaling in the pathophysiology of asthma and COPD," Respiratory Research 7(73):1-15, May 9, 2006.
Groves, "High-valent iron in chemical and biological oxidations," Journal of Inorganic Biochemistry 100:434-447, Jan. 14, 2006.
Groves, "Reactivity and mechanisms of metalloporphyrin-catalyzed oxidations," Journal of Porphyrins and Phthalocyanines 4:350-352, 2002.
Guerra et al., "The Effect of Oxygen Free Radicals on Calcium Current and Dihydropyridine Binding Sites in Guinea-pig Ventricular Myocytes," British Journal of Pharmacology 118:1278-1284, 1996.
Hammer et al., "How Do Small Water Clusters Bind an Excess Electron," Science Magazine 306(5696):675-679, Sep. 16, 2004.
Harvitt et al., "Corneal Oxygen Availability and Metabolism with Contact Lens Wear and Re-evaluation of the Oxygen Diffusion Model for Predicting Minimum Contact Lens Dk/t Values Needed to Avoid Corneal Anoxia," retrieved Apr. 9, 2003, from http://vision.berkeley.edu/sarver/mdsl_harvitt_research.html(abstracts only), 2 pages.
Headrick et al., "Spectral Signatures of Hydrated Proton Vibrations in Water Clusters," Science Magazine 308:1765-1770, Jun. 17, 2005.
Hogaboam et al., "Collagen Deposition in a Non-Fibrotic Lung," AM J. Pathol 153(6):1861-1872; abstract, Dec. 1998.
Jia et al., "Atomic-Resolution of Oxygen Concentration in Oxide Materials," Science Magazine 303:2001-2004, Mar. 26, 2004.
Jin et al., "Unusual Kinetic Stability of a Ground-State Singlet Oxomanganese(V) Porphyrin. Evidence for a Spin State Crossing Effect," Journal of the American Chemical Society 121:2923-2924, 1999.
Life 02 International (ASIA) Co., LTD—Medical Industry, www.lifeo2asia.com/medical.htm, 1 page, retrieved Jun. 3, 2003.
Ljunggren et al., "The Lifetime of a Colloid-Sized Gas Bubble in Water and the Cause of the Hydrophobic Attraction," Colloids and Surfaces A: Physicochemical and Engineering Aspects 129-130:151-155, 1997.
Lowenstein et al., "Nitric Oxide: A Physiologic Messenger," Annals of Internal Medicine 120(3):227-237, Abstract, Feb. 1, 1994.
Lower, "The BunkHouse: Water pseudoscience gallery, Gallery of water-related pseudoscience, Junk science in the marketplace," http://chem1.com/CO/gallery.html, 18 pages, retrieved Jul. 25, 2006.
Luo et al., "Mycobactin-mediated iron acquisition within macrophages," Nature Chemical Biology 1(3):149-153, Aug. 2005.
Miyazaki et al., "Infrared Spectroscopic Evidence for Protonated Water Clusters Forming Nanoscale Cages," Science Magazine, 304:1134-1137, Apr. 29, 2004.
Moe et al., "Remarkable Aliphatic Hydroxylation by the Diiron Enzyme Toluene 4-Monooxygenase in reactions with Radical or Cation Diagnostic Probes Norcarane, 1,1-Dimethylcyclopropane, and 1,1-Diethylcyclopropane," American Chemical Society, 43:15688-15701, Jul. 1, 2004.
Morris, "The physiological causes of contact lens complications," Optometry Today 28-33, Dec. 3, 1999.
Murga et al., "Activation of Akt/Protein Kinase B by G Protein-coupled Receptors," The Journal of Biological Chemistry 273(30):19080-19085, especially abstract p. 19085, col. 1, paragraph 3, 1998.
Neuman et al., "Optical Trapping," Review of Scientific Instruments 75(9):2787-2809, Sep. 2004.
Nguyen et al., "Neuroprotection by NGF and BDGF Against Neurotoxin-Exerted Apoptotic Death in Neural Stem Cells Are Mediated Through Trk Receptors, Activating P13-Kinase and MAPK Pathways," Neurochemical Research 34(5):942-951, especially abstract, p. 943, col. 1, paragraphs 2-3, 2009.
Nozaki et al., "New enhancers for the chemiluminescent peroxidase catalyzed chemiluminescent oxidation of pyrogallol and purpurogallin," Journal of Biolumin Chemilumin 10:151-156, 1995.

(56) References Cited

OTHER PUBLICATIONS

Ohgaki et al., "Physiochemical approach to nanobubble solutions," Chemical Engineering Science 65:1296-1300, 2010.
Paik et al., "Electrons in Finite-Sized Water Cavities: Hydration Dynamics Observed in Real Time," Science Express, 306(5696):672-675, Sep. 16, 2004.
Pan et al., "Role of the Rho GTPas in Bradykinin-Stimulated Nuclear Factor-kB Activation and IL-1B Gene Expression in Cultured Human Epithelial Cells," The Journal of Immunology 160:3038-3045, 1998.
Park, et al., "Nitric oxide regulates nitric oxide synthase-2 gene expression by inhibiting NF-KB binding to DNA," Biochem J. 322:609-613, abstract, 1997.
Patent Office of the Russian Federation, Official Action, Application No. 2004133560/15(036500), original in Russian plus English translation, Jan. 27, 2006, 6 pages.
Pronated Water Clusters in Nature, "Protonated Water Clusters in Interstellar Clouds, the Upper Atmosphere and Biomolecules," http://pro3.chem.pitt.edu/richard/prot_clust_nature.html, 1 page, retrieved Oct. 29, 2004.
Robertson, In re Anthony J. Robertson and Charles L. Scripps, United States Court of Appeals Federal Circuit, No. 98-1270, Cite as 169 F.3d 743, Westlaw, 5 Pages, Feb. 25, 1999.
Rutgeerts et al., "Review article: the limitations of corticosteroid therapy in Crohn's disease," Aliment Pharmacol Ther. 15:1515-1525, abstract, Oct. 2001.
Salzman et al., "Nitric oxide dilates tight junctions and depletes ATP in cultured Caco-2BBe intestinal epithelial monolayers," AJP-Gastrointestinal and Liver Physiology 268(2):361-G373, Abstract, 1995.
Schmidt et al., "A role for Rho in receptor- and G protein-stimulated phospholipase C. Reduction in phosphatidylinositol 4,5-bisophosphate by Clostridium difficile toxin B.," Naunyn Schmiedebergs Arch Pharmacol 354(2):87-94, abstract only, Jul. 1996.
Science Week (1) Chemistry: On Protonated Water Clusters, points made by Zwier-Science (2004) 204:1119; (2) On Water Structure, points made by Head-Gordon et al.-Chem. Rev (2002) 102:2651; (3) Liquid Water: Current Research Problems, points made by Keutsch et al., Proc. Nat. Acad. Sci. (2001) 98:10533.
Shin et al., "Infrared Signature of Structures Associated with the H+(H2O)n (n=6 to 27) Clusters, Science Magazine," 304:1137-1140, May 21, 2004.
Stoll et al., "Inflammation and Atherosclerosis Novel Insights into Plaque Formation and Destabilization," American Stroke Association through the American Journal of Heart Association 37:1923-1932, Jul. 2006.
Suslick, "Sonochemistry," Science Magazine 247:1439-1445, Mar. 23, 1990.
Tristani-Firouzi et al., "Oxygen-induced constriction of rabbit ductus arteriosus via inhibition of a 4-aminopyridine-, voltage-sensitive potassium channel," J. Clin Invest 98:1959-1965, 1996.
Wang, "Radical Clocks: Molecular Stopwatches for timing Radical Reactions," 65-72, Apr. 27, 2006.
Warheit et al., "Development of a respiratory Allergy model in male Brown Norway rats," Pulmonary immune and gene expression studies, Ann. Occup. Hyg., 46:362-364, 2002.
Watson, U.S. Appl. No. 13/097,565, filed Apr. 29, 2011.
Watson, U.S. Appl. No. 13/126,117, filed Jul. 19, 2011.
Wojciak-Stothard et al., "Rac and Rho play opposing roles in the regulation of hypoxia/reoxygenation-induced permeability changes in pulmonary artery endothelial cells," Am J of Lung Cell Mol Physiol 288:L749-L760, 2005.
Wood et al., U.S. Appl. No. 12/861,179, filed Aug. 23, 2010.
Wood et al., U.S. Appl. No. 13/016,659, filed Jan. 28, 2011.
Wood et al., U.S. Appl. No. 13/028,058, filed Feb. 15, 2011.
Wronski et al., "Interfacial area in a reactor with helicoidal flow for the twophase gas-liquid system," Chemical Engineering Journal 105:71-79, 2005.
(1) Wunderlich et al. "In vivo observation of oxygen-supersaturated water in the human mouth and stomach", Magnetic Resonance Imaging, 22(4): 551-556, 2004; (2) Divino et al. "Injection of highly supersaturated oxygen solutions without nucleation", Journal of Biomechanical Engineering, 124(6): 676-683, 2002; (3) 02 Canada Water, Product Information from 02 Canada Water, Inc., http://www.ocanadawater.com/BeverageDiffusion.html; (4) FBC Technologies "O2 x-Box (R)Super Oxygenation Process", http://www.fbctech.com/oxbox.htm, http://www.lsbu.ac.uk/water/anmlous.html; (5) Wayne State University Press Researcher Discovers Potential Approach to Hyperoxygenate Blood, Wayne State University Press Release, Apr. 4 2006, 4 pages.
Zozulya et al., "The Role of Regulatory T Cells in Multiple Sclerosis," Nature Clinical Practice Neurology 4(7):384-398, Jun. 24, 2008.
Zwier, "The structure of protonated water clusters," Science Magazine 304(5674):1119-1120, Apr. 29, 2004.
Borsa et al., "Oral consumption of electrokinetically modified water attenuates muscle damage and improves postexercise recovery," Journal of Applied Physiology 114:1736-1742, Apr. 11, 2013.
Akbar, "Expression of the TRPV1 receptor differs in quiescent inflammatory bowel disease with or without abdominal pain," Gut 59:767-774 (doi:10.1136/gut.2009.194449), 2010.
Andrews, "Determination of minimum inhibitory concentrations," Journal of Antimicrobial Chemotherapy vol. 48 (suppl. S1), pp. 5-16, 2001.
Aqueous Fluid (definition), Retrieved from http://www.thefreedictionary.com/aqueous and http://www.habazar.com/opticaldirectory/a2z.htm, Aug. 29, 2013.
Baker et al. "Mutations in progranulin cause tau-negative frontotemporal dementia linked to chromosome 17", Nature, 442(24):916-919, Aug. 2006.
Bates et al., "The use and misuse of Penh in animal models of lung disease," American Journal of Respiratory Cell and Molecular Biology 31(3):373-4, Sep. 2004.
Berger et al., "Antimyelin Antibodies as a Predicator of Clinically Definite Multiple Sclerosis after a First Demyelinating Event," The New England Journal of Medicine 349(2):139-145, Jul. 10, 2003.
Boedker et al., "Budesonide epimer R, LAU-8080 and phenyl butyl nitrone synergistically repress cyclooxygenase-2 induction in [IL-1β+Aβ42]-stressed human neural cells," Neuroscience Letters, 380:176-180, 2005.
Boyle, "Adult Cystic Fibrosis," Journal of the American Medical Association (JAMA) 296(13);1787-1793, Oct. 17, 2007.
Breitner et al., "Extended results of the Alzheimer's disease anti-inflammatory prevention trial (ADAPT)," Alzheimers Dement. 7(4):402-411, published Jul. 2011.
Bulakbasi et al., "Massive Lower Gastrointestinal Hemorrhage from the Surgical Anastomosis in Patients with Multiorgan Trauma: Treatment by Subselective Embolization with Polyvinyl Alcohol Particles," CardioVascular and Interventional Radiology 22:461-467, 1999.
Caro et al., "Healing and Relapse Rates in Gastroesophageal Reflux Disease Treated with the Newer Proton-Pump Inhibitors Lansoprazole, Rabeprazole, and Pantoprazole Compared with Omeprazole, Ranitidine, and Placebo: Evidence from Randomized Clinical Trials," Clinical Therapeutics 23(7):998-1017, 2001.
Celli et al., "Standards for the diagnosis and treatment of patients with COPD: a summary of the ATS/ERS position paper," Eur, Respir. J. 23:932-946, 2004.
Cheng et al., "HCl-acativated neural and epithelial vanilloid receptors (TRPV1) in cat esophageal mucosa, American Journal Physiol Gastrointest Liver Physiol 297:G135-G143, 2009.
Chu et al., "Urokinase-type plasminogen activator, receptor, and inhibitor correlating with gelatinase-B (MMP-9) contribute to inflammation in gouty arthritis of the knee,". The Journal of Rhuematology 33(2):311-317, Feb. 2006.
Corrigan, "Eotaxin and asthma: some answers, more questions," Clinical and Experimental Immunology 1999 116:1-3
Cross, "Can Probiotics Help GERD?" http://www.livestrong.com.article/474546-can-probiotics-help-gerd/, Apr. 5, 2012.
Ex Parte Kubin, No. 2007-0819 (B.P.A.I, May 31, 2007) ("Board Decision"), pages 1-18.(in particular, pp. 10, 14 and 15).
Finkel, "Redox-dependent signal transduction," FEBS Letters 476:52-54, 2000.

(56) References Cited

OTHER PUBLICATIONS

Fletcher et al., "T cells in multiple sclerosis and experimental autoimmune encephalomyelitis," Clinical and Experimental Immunology 162:1-11, 2010.
Gabbey "What are Anaerobic Infections?," Anaerobic Infections/ Definition and Patient Education, published Jun. 18, 201.3, downloaded on Nov. 29, 2014, from http://www.healthline.com/health/anaerobic-infections, 3 pages.
Glass et al., "Mechanism Underlying Inflammation on Neurodegeneration" Cell 140(6):918-934, Mar. 19, 2010.
Godoy et al., "Central and systemic IL-I exacerbates neurodegeneration and motor symptoms in a model of Parkinson's disease," Brain 131:1880-1894, 2008.
Guarino et al., "Increased TRPV1 gene expression in esophageal mucosa of patients with non-erosive and erosive reflux disease," Neurogastroenterol Motil 22:746-e219, 2010.
Harari et al., "NF-kB and innate immunity in ischemic stroke," National Institute of Health Public Access Author Manuscript, published in final edited form as Ann New York Academy of Science 1207: 32-40, Oct. 2010.
Hardy et al. "The Amyloid Hypothesis of Alzheimer's Disease: Progress and Problems on the Road to Therapeutics," Science 297:353-356, Jul. 19, 2002.
Hedbom et al., "Molecular aspects of pathogenesis in osteoarthritis: the role of inflammation," Cellular and Molecular Life Sciences 59(1):45-53, Jan. 2002.
Holub et al, "Cytokines and Chemokines as Biomarkers of Community-Acquired Bacterial Infection," Mediators of Inflammation, vol. 2013, Article ID 190145, published after Mar. 26, 2013, by Hindawi publishing production, 7 pages.
Hong-Qi et al., "Current advances in the treatment of Alzheimer's disease: focused on considerations targeting AB and tau," Translational Neurodegeneration 1:21 (http://www.translationalneurodegeneration.com/content/1/1/21), 12 pages, Oct. 30, 2012.
Hubbard et al., "Cell signalling diversity of the Gqalpha family of heterotrimeric G proteins," Cellular Signalling 18(2):135-150, Sep. 22, 2005.
Kemp et al., "Once-daily budesonide inhalation suspension for the treatment of persistent asthma in infants and young children," Annals of Allergy, Asthma, & Immunology, Sep. 1999, 83(3):231-239.
Khasnavis et al., "Protection of Dopaminergic Neurons in a Mouse Model of Parkinson's Disease by a Physically-Modified Saline Containing Charge-Stabilized Nanobubbles," The Journal of Neuroimmune Pharmacology, Oct. 11, 2013, 15 pages.
Khasnavis et al., "Suppression of Nuclear Factor-KB Activation and Inflammation in Microglia by Physically Modified Saline," The Journal of BioloQical Chemistry, Aug. 24, 2012, 287(35):29529-29542.
Knobloch et al., "Dendritic spine loss and synaptic alterations in Alzheimer's disease,"Mol Neurobiol 37:73-82, 2008.
Lambertsen et al., "Inflammatory cytokines in experimental and human stroke,"Journal of Cerebral Blood Flow & Metabolism 32:1677-1698, 2012.
Lassmann, "Hypoxia-like tissue injury as a component of multiple sclerosis lesions," J. Neurol. Sci. 206(2):187-191 (abstract, p. 190, paragraph 3), Feb. 15, 2003.
Lee et al., "Tau phosphorylation in Alzheimer's disease: pathogen or protector?," TRENDS in Molecular Medicine 11(4):164-169, Apr. 2005.
Licalzi et al., "Effect of hemorrhagic hypotension and hypoventilation on lower esophageal sphincter pressure," Annals of Surgery 192(1):53-57, p. 55, para 6-page 56, para 1, (Document entitled "Licalzi PubMed" included to establish publication date.), Jul. 1980.
Liu, "Thymic stromal lymphopoietin: master switch for allergic inflammation," J. Experimental Medicine 203(2):269-273, 2006.
Lundblad et al., "A reevaluation of the validity of unrestrained plethysmography in mice," J. Appl, Physiol, 93:1198-1207, 2002.
Martin et al., "Cognitive Function Over Time in the Alzheimer's Disease Anti-inflammatory Prevention Trial (ADAPT)," Arch Neurol. 65(7):896-905, Jul. 14, 2008.
Masters et al., "Anti-inflammatory drugs fall short in Alzheimer's disease," Nature Medicine Community Corner 14(9):916, Sep. 2008.
Modi et al., "A Physically-Modified Saline Suppresses Neuronal Apoptosis, Attenuates, Tau Phosphorylation and Protects Memory in an Animal Model of Alzheimer's Disease," Plos One, www.plosone.org, Aug. 2014: 9(8):e103606, 16 pages.
Mondal et al., "Protection of Tregs, Suppression of Th1 and Th17 Cells, and Amelioration of Experimental Allergic Encephalomyelitis by a Physically-Modified Saline," PloS One, Dec. 2012, 7(12)e51869, 18 pages.
Murray et al., "Exacerbation of CNS inflammation and neurodegeneration by systemic LPS treatment is independent of circulating IL-1β and II-6," Journal of Neuroinflammation 8:50, May 17, 2011.
Nickols et al., "Development of allosteric modulators of GPCRs for treatment of CNS disorders," Neurobiology of Disease 61:55-71, available online Sep. 27, 2013.
NIH (National Institute of Health, National Heart, Lung and Blood Institute), "What are the Signs and Symptoms of Cystic Fibrosis?," http://www.nhlbi.nih.gov/health/health-topics/topics/cf/signs.html, retrieved on Jan. 1, 2014.
NIH (National institute of Health, National Heart, Lung and Blood Institute), "What is Atherosclerosis?" http://www.nhlbi.nih.gov/health/health-topics/topics/atherosclerosis, published Jul. 1, 2011, retrieved on Dec. 18, 2013.
NINDS "What is Corticobasal Degeneration?," Corticobasal Degeneration Information Page: National Institute of Neurological Disorders and Stroke (NINDS), retrieved on Jan. 9, 2015, from http://www.ninds.nih.gov/disorders/corticobasal_degeneration.htm.
NINDS, "What is progressive supranuclear palsy?," Progressive Supranuclear Palsy Fact Sheet: National Institute of Neurological Disorders and Stroke (NINDS), retrieved Jan. 9, 2015, from http://www.ninds.nih.gov/disorders/psp/detail_psp.htm.
Partridge, "Bacteria 'cause Asthma'," BBC News Health 2001: retrieved May 28, 2014, from http://news.bbc.co.uk/2/hi/health/1372007.stm 3 pages.
Peles et al., "Differential Effects of TRPV1 Antagonists in Acid-induced Excitation of Esophageal Vagal Afferent Fibers of Rats," Neuroscience 2009 161(2):515-525.(doi:10.1016/j.neuroscience,2009.03.040).
Planas et al., "Signalling pathways mediating inflammatory responses in brain ischaemia," International Symposium on Neurodegeneration and Neuroprotection, Biochemical Society Transactions 34(6):1267-1270, 2006.
Present et al., "Infliximab for the Treatment of Fistulas in Patients with Crohn's Disease" The New England Journal of Medicine 340(18):1398-1405, May 6, 1999.
Rivera et al., "Current Concepts in Antimicrobial Therapy Against Select Gram-Positive Organisms: Methicillin-Resistant *Staphylococcus aureus*, Penicillin-Resistant Pneumococci, and Vancomycin-Resistant Enterococci," Symposium on Antimicrobial Therapy, Mayo Clinic Proceedings 86(12)1230-1243, published Dec. 2011.
Sagel et al., "Induced sputum matrix metalloproteinase-9 correlates with lung function and airway inflammation in children with cystic fibrosis," Pediatr. Pulmon. 39(3):224-232, Mar. 2005.
Sanchez-Pernaute et al., "Selective COX-2 inhibition prevents progressive dopamine neuron degeneration in a rat model of Parkinson's disease," Journal of Neuroinflammation 1(6):1-11, 2004.
Silverman et al., "Inhibition of Daptomycin by Pulmonary Surfactant: In Vitro Modeling and Clinical Impact," Journal of Infectious Diseases, Jun. 15, 2005, 191:2149-52 (published electronically May 5, 2005).
Singh et al., "Benzimidazolone Activators of Chloride Secretion: Potential Therapeutics for Cystic Fibrosis and Chronic Obstructive Pulmonary Disease," J. Pharmacol. and Experimental Therapeutics 296(2):600-611, 2001.
Sjogren et al., "Increased intrathecal inflammatory activity in frontotemporal dementia: pathophysiological implications," J. Neurol. Neurosurg. Psychiatry 75:1107-1111, 2004.
Sun et al., "Role of G protein-coupled receptors in inflammation," Acta Pharmacologica Sinica, 2012, 33:342-350.

(56) References Cited

OTHER PUBLICATIONS

Taylor, "Regulation of intestinal epithelial gene expression in hypoxia," Kidney Int. 66(2):528-531, abstract; p. 530, paragraph 3 (Document entitled "Taylor Ingenta"included to establish publication date), Aug. 2004.

Teronen et al., Annals of the New York Academy of Sciences 878:453-465, Jun. 1999.

Torr, "Conversion between Torr and atm," http://antoine.frostburg.edu/chem/senese/101/solutions/faq/predicting-DO.shtml, retrieved on Dec. 12, 2013.

Torre, "Is Alzheimer's disease a neurodegenerative or a vascular disorder? Data dogma, and dialectics," Neurology 3:184-190, Mar. 2004.

Van Winsen et al., "Sensitivity to glucocorticoids is decreased in relapsing remitting multiple sclerosis," J. Clin. Endocrinol, Metab. 90(2):734-740, abstract, Feb. 2005.

Venken et al., "Disturbed regulatory T cell homeostasis in multiple sclerosis," Trends in Molecular Medicine, 16(2):58-68, Feb. 2010.

Vignali et al., "How regulatory T cells work," Nature Review— Immunology Jul. 2008, 8:523-532.

Viviani et al., "Cytokines and neuronal channels: A molecular basis for age-related decline of neuronal function?," Experimental Gerontology 46:199-206, 2011.

Vliet et al., "Nitric oxide: a pro-inflammatory mediator in lung disease?", Respiratory Research 1:67-72, Aug. 15, 2000.

Watson et al., U.S. Appl. No. 12/258,210, filed Oct. 24, 2008.
Watson et al., U.S. Appl. No. 12/256,774, filed Oct. 23, 2008.
Watson et al., U.S. Appl. No. 12/257,224, filed Oct. 23, 2008.
Watson et al., U.S. Appl. No. 12/257,607, filed Oct. 24, 2008.
Watson et al., U.S. Appl. No. 12/259,101, filed Oct. 27, 2008.
Watson et al., U.S. Appl. No. 61/373,652, filed Aug. 13, 2010 (unpublished).

Whittaker et al., "Matrix Metalloproteinases and their Inhibitors— Current Status and Future Challenges," Celltransmissions 7(1):3-12, 2001.

Wood et al., U.S. Appl. No. 12/945,703, filed Nov. 12, 2010.

Yasuda et al., "Modulation of hypoglossal motoneuron excitability by NK1 receptor activation in neonatal mice in vitro," Journal of Physiology 534(2):447-464, published Jan. 5, 2001.

Zhao et al., "Expression of Matrix Metalloproteinase-9 mRNA in Osteoporotic Bone Tissues," Journal of Tongii Medical University 17(1):28-31, Mar. 1997.

Ziegler et al., "Thymic stromal lymphopoietin in normal and pathogenic T cell development and function," Nature Immunology 7(7):709-714, Jul. 2006.

Ziegler, "The role of thymic stromal lymphopoietin (TSLP) in allergic disorders," Current Opinion in Immunology 22(6):795-799, Dec. 2010.

Ziegler, "Thymic stromallymphopoietin (TSLP) and allergic disease," J. Allergy Clin. Immunol. 130(4):845-852, Oct. 2012.

* cited by examiner

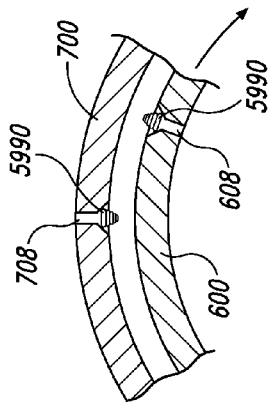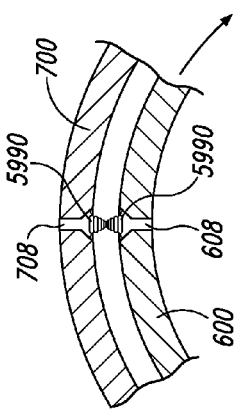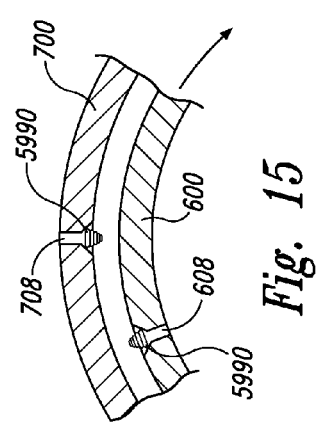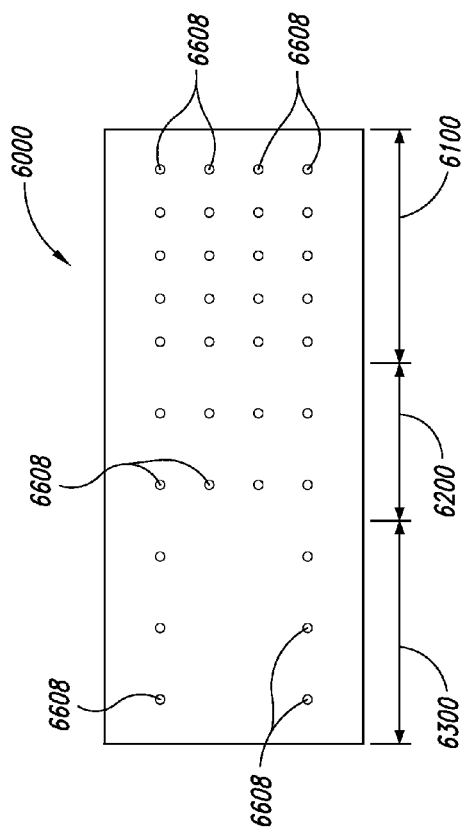

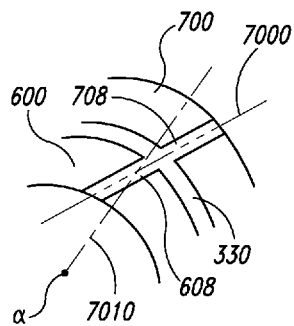
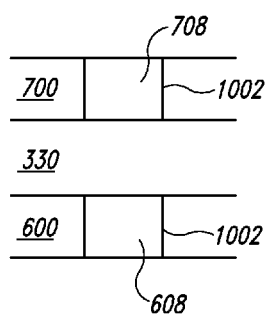
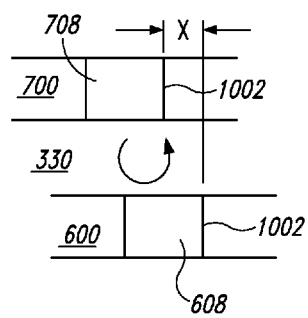
Fig. 19          Fig. 20          Fig. 21
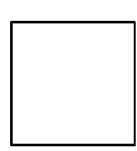
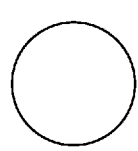
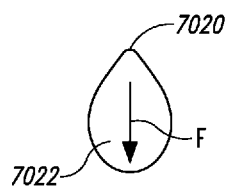
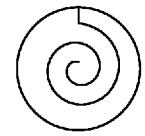
Fig. 22          Fig. 23          Fig. 24          Fig. 25
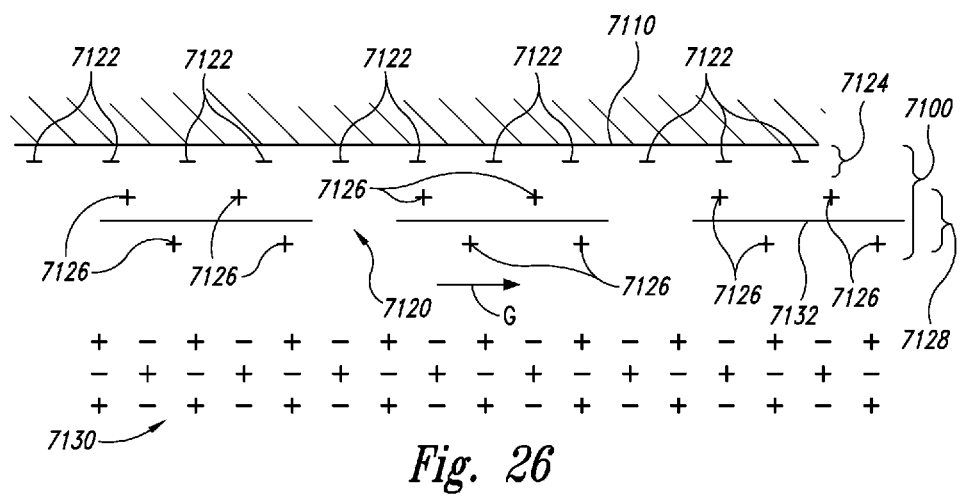
Fig. 26

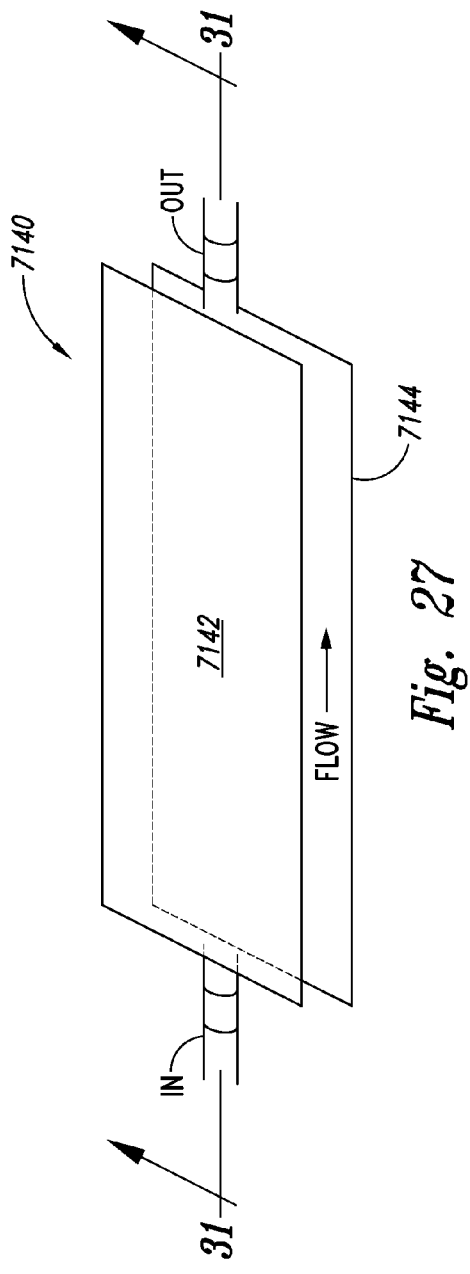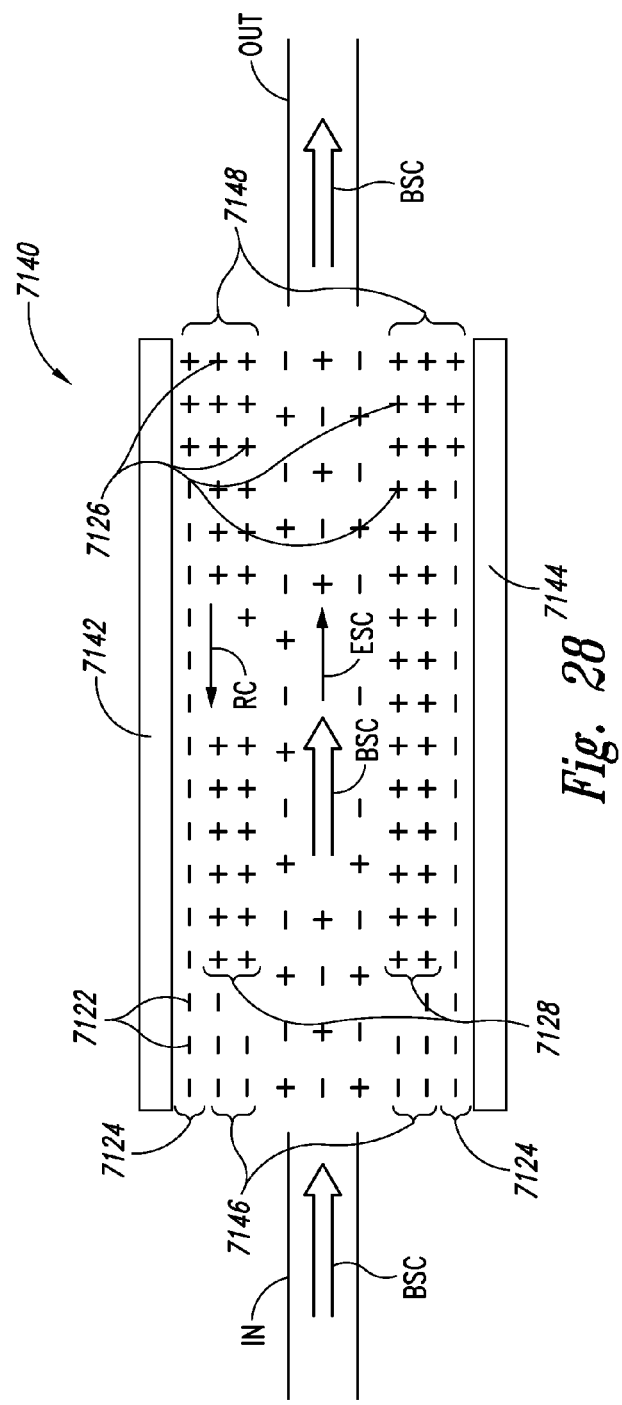

COMPOSITIONS AND METHODS FOR ENHANCING PHYSIOLOGICAL PERFORMANCE AND RECOVERY TIME

CROSS-REFERENCE TO RELATED APPLICATIONS

This application claims the benefit of priority to U.S. Provisional Patent Application Ser. Nos. 61/332,669 filed May 7, 2010, 61/358,798 filed Jun. 25, 2010, and 61/413,258 filed Nov. 12, 2010, all of which are incorporated herein by reference in their entirety.

FIELD OF THE INVENTION

The present invention is directed generally to sports, exercise, energy and/or food beverages and more particularly to electrokinetically-altered, oxygenated sports, energy and/or food beverages. Particular aspects relate to the use of electrokinetically-altered fluids (e.g., gas-enriched (e.g., superoxygenated) electrokinetic fluids, comprising an ionic aqueous solution of charge-stabilized oxygen-containing nanostructures) administered in an amount sufficient to provide for enhancing at least one of physiological performance and recovery time. Certain aspects relate to administering said beverages in an amount sufficient to provide for preventing exercise-induced muscle and/or tendon damage and/or enhancing/facilitating muscle and/or tendon recovery from exercise and/or exercise-induced damage). Certain aspects relate to preventing and/or ameliorating and/or enhancing recovery from muscle or tendon strain associated with chronic, repetitive movement. Further aspects relate to ameliorating the effects of physical exertion of the subject. Certain aspects relate to improved methods for producing electrokinetically altered aqueous fluids (including sports beverages).

BACKGROUND OF THE INVENTION

In humans and other animals, exercise, strenuous training, and exposure to elements (e.g., sunlight, wind, rain, cold and heat) can result in significant physiological changes. Subjects exercising or training are at risk for developing injuries (e.g., muscle and/or tendon damage), especially subjects doing so in extreme conditions (e.g., cold or heat, high altitude, long durations, high intensity, repetitive, aerobic, contact sports, etc.). For example, excessive heat temperatures, in particular, environmental heat illnesses include but are not limited to heat syncope, heat exhaustion, dehydration syndrome, and heat stroke. The potentially fatal clinical syndrome of heat stroke has been described in marathon runners, military recruits, football players, and in hot industrial environments. An epidemic appearance of heat stroke has been described during heat waves in urban areas (Ferguson, M., And M. M. O'brien, "Heat Stroke In New York City: Experience With 25 Cases," N.Y. State J. Med. 60:2531-2538, 1960).

Likewise, impaired or incomplete recovery following high-intensity exercise can negatively affect physical performance and delay functional progression, thereby reducing an athlete's chance of performing at his or her peak level. Athletes are constantly seeking ways to prevent exercise-induced muscle damage and facilitate muscle recovery from strenuous exercise. For example, athletes have used dietary supplements extensively to facilitate tissue growth and repair following muscle-damaging events such as high-intensity resistance exercise and participation in contact sports. Following strenuous exercise, an acute inflammatory response drives the repair process by synthesizing and releasing chemical mediators locally in the injured muscle. However, while inflammatory mediators may help attract growth factors used for protein synthesis and muscle repair, excessive inflammatory response may damage muscle and thereby hinder the repair process.

"Dehydration syndrome" may be characterized and/or accompanied by loss of appetite and limited capacity for work. Evidence of heat exhaustion becomes apparent with losses of, for example, 5% of the body water, and at about 7% loss of body water disorientation and hallucinations may occur. Losses of body water of 10% or greater are extremely hazardous and lead to heat stroke and death if not treated immediately. Heat stroke is accompanied by high body temperature (41.1° C.-43.3° C.; 106° F.-110° F.), deep coma, and in most cases a complete absence of sweating, and failure of major organ systems.

At least three factors determine the thermal balance of the body: metabolic heat production, heat exchange between the organism and its surroundings, and heat loss by the evaporation of sweat (Knochel, J. P. [1980] "Clinical Physiology Of Heat Exposure," In Clinical Disorders Of Fluid And Electrolyte Metabolism, M. H. Maxwell And C. R. Kleeman, Eds., Mcgraw-Hill, New York). For the subject exercising or working, particularly in a hot environment, the capacity to dissipate metabolically produced heat depends for the most part on the subject's ability to form and vaporize sweat (Costill, D. L. And K. E. Sparks "Rapid Fluid Replacement Following Thermal Dehydration," J. Appl. Physiol. 34(3):299-303, 1973; Greenleaf, J. E. "Hyperthermia And Exercise," Int. Rev. Physiol. 20:157-208, 1979).

During exercise, especially in a hot environment, serious deficits in effective circulating volume may occur. Muscular work, independent of environment, results in massive shunting of blood to skeletal muscle, along with a substantial loss of plasma volume into the working muscle. Moreover, effective circulating volume is also diminished by losses of sweat (Knochel [1980] supra). The deficit in intravascular volume impedes the delivery of heated blood to the periphery for evaporative cooling. Thus, in the dehydrated exercising subject, there is a progressive increase in the core body temperature as sweat losses accumulate.

Notable among the many physiological responses to physical exertion are increased body temperature, perspiration and pulse rate, a decrease in the blood volume, and biochemical changes associated with the metabolism of compounds to produce energy. In addition, approximately 90% of the body's energy is created by oxygen. All of the activities of the body, from brain function to elimination, are regulated by oxygen. Blood plasma holds approximately three percent (3%) dissolved oxygen, and red blood cells (hemoglobin) hold ninety-seven percent (97%). From the red blood cells the oxygen passes out into the plasma and is transferred to cells that need oxygen during metabolic processes. These cells pass $CO_2$ back to the plasma where it is then picked up by the red blood cells. This process rapidly increases, for example, during exercise and strenuous training.

Prior research in the art has focused on the ability of glycerol to cause water retention. However, water retention alone has little or no correlation with enhanced endurance or physiological performance. In order to have a beneficial effect on endurance and performance, water must be appropriately allocated throughout the body. Mere reduction in urine output is insufficient. Water must be available for sweating (efficient cooling), hydration of cells, and plasma volume must be maintained. Only if these physiological objectives are met can endurance and performance be enhanced.

Osmotic pressure is primarily responsible for the direction and rate of movement of water across semi permeable membranes in the body. Thus, water will move across a semi permeable membrane such that the net flow of water will be across the membrane into the fluid which initially had the highest concentration of solutes, and thus the allocation of water between digestive organs, blood plasma, and cells depends upon the relative osmotic pressures between these sites. Although it has been established that the ingestion of massive amounts of glycerol results in the retention of water within the body (i.e., the rate of urine flow is decreased), this observation alone produces no information as to whether the body's physiological responses to heat or physical exertion have been enhanced. For example, a large concentration of glycerol in the stomach or intestine can cause water to move across the gastrointestinal membranes into the digestive tract and cause detrimental responses to physical exertion and heat exposure. Alternatively, high concentrations of plasma glycerol can cause water to leave the cells and enter the plasma, resulting in detrimental cellular dehydration.

There is, therefore, a pronounced need in the art for novel and effective methods to enhance exercise performance and recovery time and related conditions as described herein.

BRIEF DESCRIPTION OF THE SEVERAL VIEWS OF THE DRAWING(S)

FIG. 15 is a cross-sectional view of the mixing chamber of the mixing device of FIG. 2 taken through a plane orthogonal to the axis of rotation depicting a rotary flow pattern caused by cavitation bubbles when a through-hole of the rotor approaches (but is not aligned with) an aperture of the stator.

FIG. 16 is a cross-sectional view of the mixing chamber of the mixing device of FIG. 2 taken through a plane orthogonal to the axis of rotation depicting a rotary flow pattern caused by cavitation bubbles when the through-hole of the rotor is aligned with the aperture of the stator.

FIG. 17 is a cross-sectional view of the mixing chamber of the mixing device of FIG. 2 taken through a plane orthogonal to the axis of rotation depicting a rotary flow pattern caused by cavitation bubbles when a through-hole of the rotor that was previously aligned with the aperture of the stator is no longer aligned therewith.

FIG. 18 is a side view of an alternate embodiment of a rotor.

FIG. 19 is an enlarged fragmentary cross-sectional view taken through a plane orthogonal to an axis of rotation of the rotor depicting an alternate configuration of through-holes formed in the rotor and through-holes formed in the stator.

FIG. 20 is an enlarged fragmentary cross-sectional view taken through a plane passing through and extending along the axis of rotation of the rotor depicting a configuration of through-holes formed in the rotor and through-holes formed in the stator.

FIG. 21 is an enlarged fragmentary cross-sectional view taken through a plane passing through and extending along the axis of rotation of the rotor depicting an alternate offset configuration of through-holes formed in the rotor and through-holes formed in the stator.

FIG. 22 is an illustration of a shape that may be used to construct the through-holes of the rotor and/or the apertures of the stator.

FIG. 23 is an illustration of a shape that may be used to construct the through-holes of the rotor and/or the apertures of the stator.

FIG. 24 is an illustration of a shape that may be used to construct the through-holes of the rotor and/or the apertures of the stator.

FIG. 25 is an illustration of a shape that may be used to construct the through-holes of the rotor and/or the apertures of the stator.

FIG. 26 is an illustration of an electrical double layer ("EDL") formed near a surface.

FIG. 27 is a perspective view of a model of the inside of the mixing chamber.

FIG. 28 is a cross-sectional view of the model of FIG. 27.

FIGS. 45A and 45B illustrate a graphical representation of a exemplary embodiments of a bioreactor system 3300a.

Figure 47A:
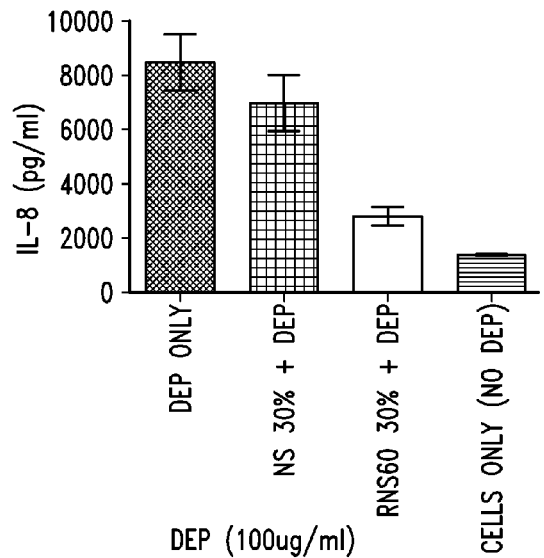
Figure 47B:
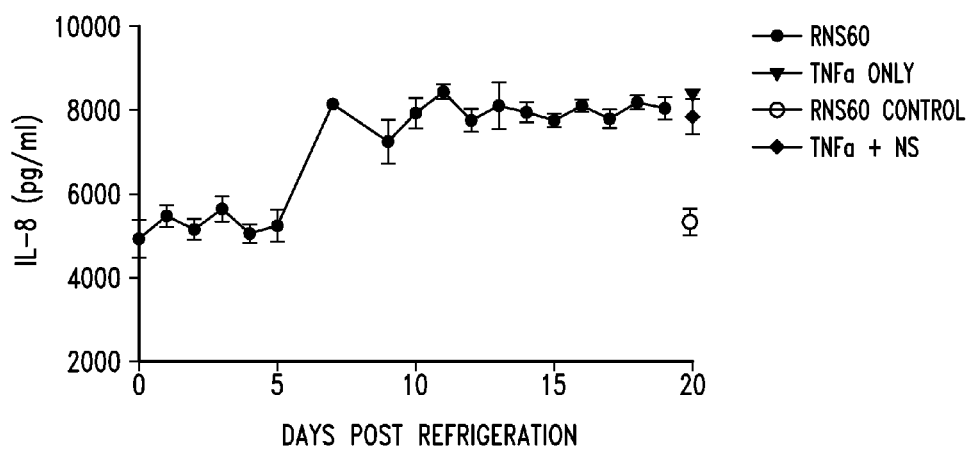

FIG. 47A shows the effect that RNS60 has on DEP mediated IL-8 stimulation in human bronchial epithelial cells. FIG. 47B shows that RNS60 regulates rTNFa induced IL-8, and it retains its biological activity at room temperature for days. Note that the points for "TNFα ONLY", RNS60 CONTROL", and TNFα+NS were only measured at 20 days.

Figure 48:
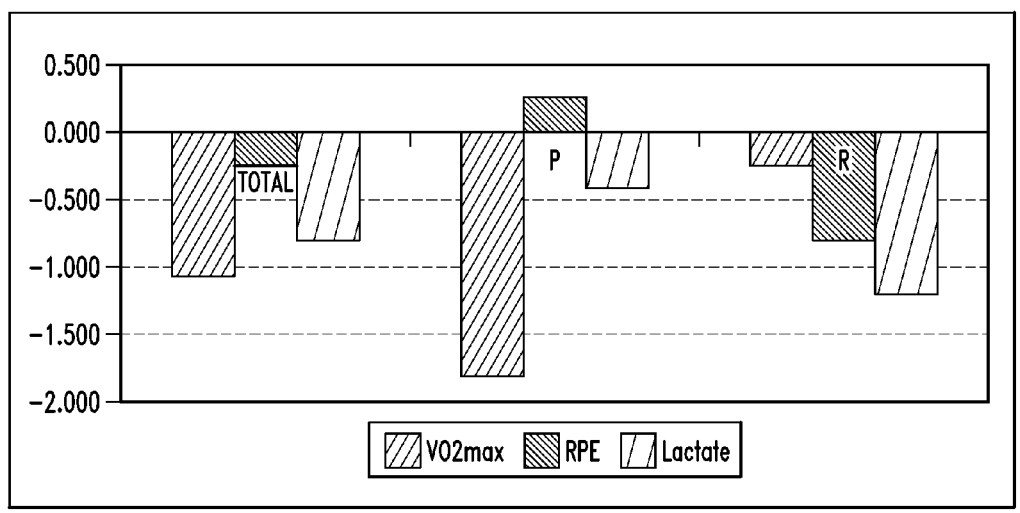

FIG. 48 illustrates the benefits of consuming the electrokinetically-altered fluids for exercising individuals. The results (see Table 4 herein below) indicate that the beverage had an effect on all 3 measured parameters of exercise performance, and that the direction of the effect was favorable in all 3 areas (i.e., positive for $VO_2$ max, negative for RPE (rating of perceived exertion), and negative for lactate).

Figure 49:
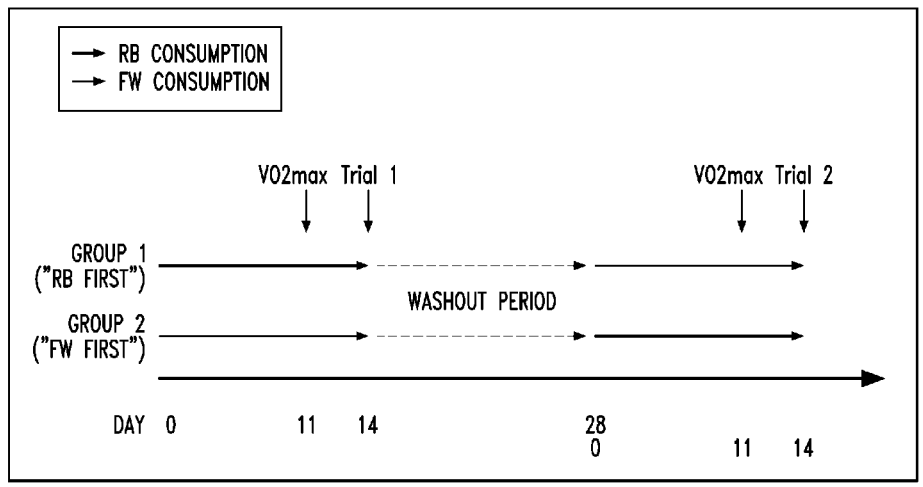

FIG. 49 shows a study design overview.

FIGS. 50 A and B show that RB consumption improves $VO_2$max in fitter athletes.

Figure 51:
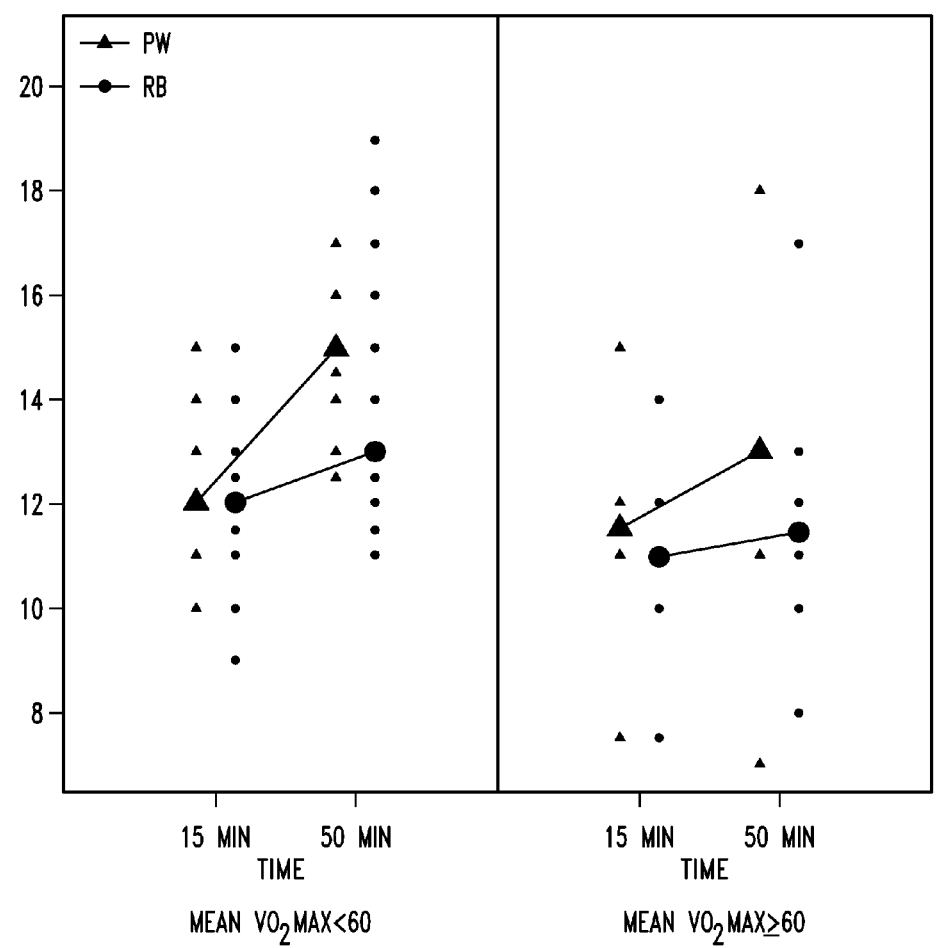

FIG. 51 shows that RB consumption decreases RPE. RPE is plotted on the Y-axis, and was recorded according to the Modified Borg Scale.

Figure 52:
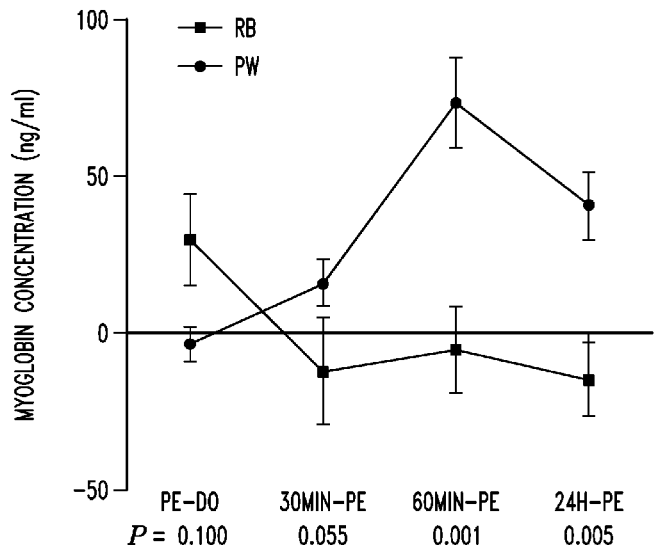

FIG. 52 shows time point differences in levels of plasma myoglobin.

Figure 53:
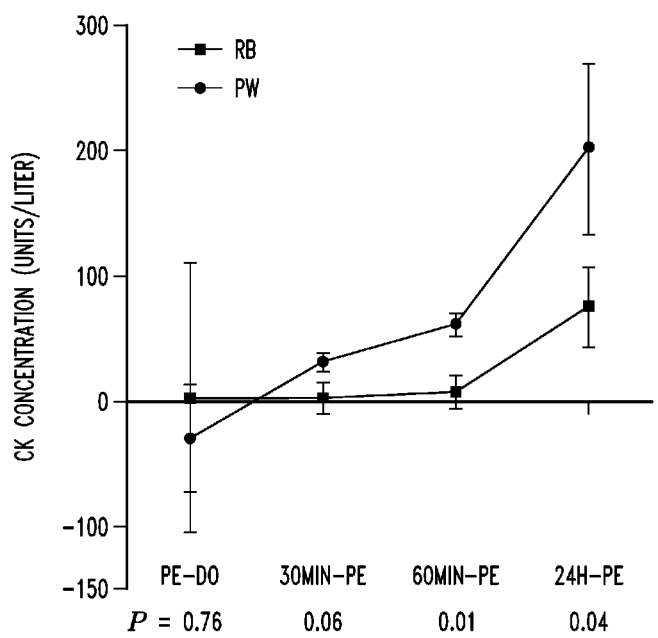

FIG. 53 shows time point differences in plasma CK levels.

Figure 54A:
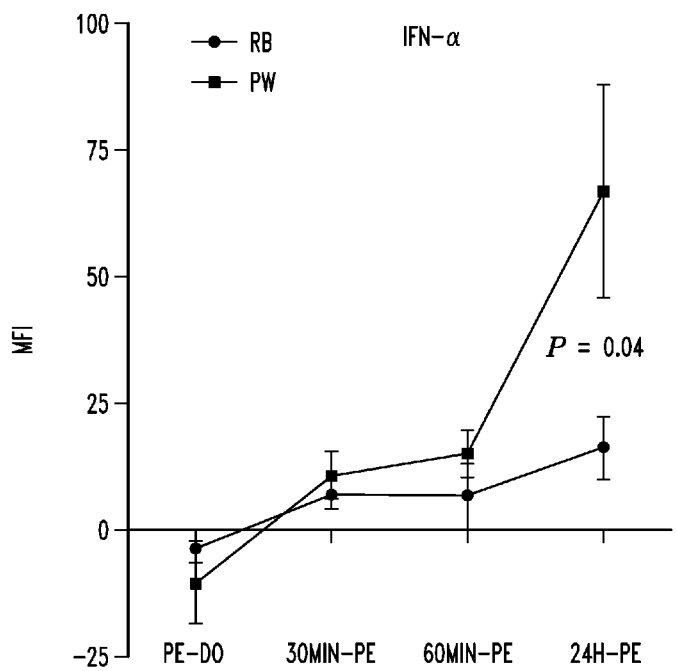
Figure 54B:
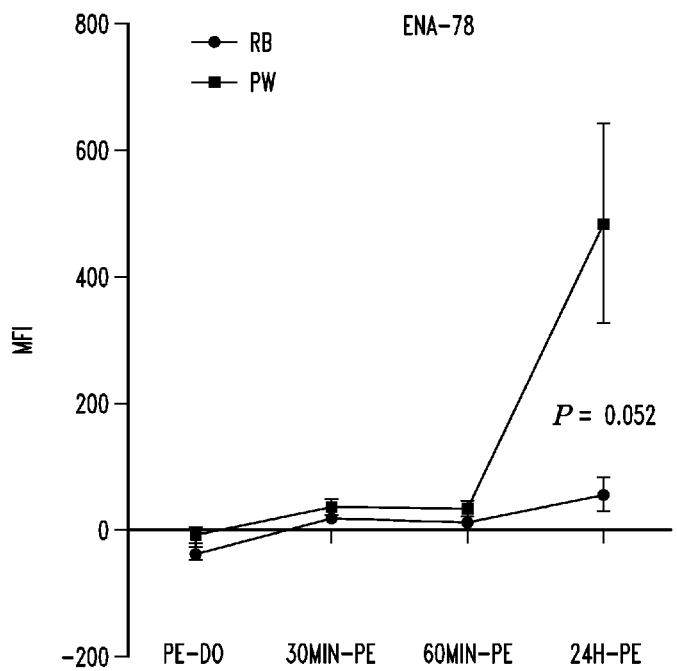

FIG. 54 shows that RB inhibited the exercise-induced increase of plasma levels of IFN-α (A) and ENA-78 (B). Mean fluorescence intensity units (MFI) are plotted on the Y-axis.

Figure 55:
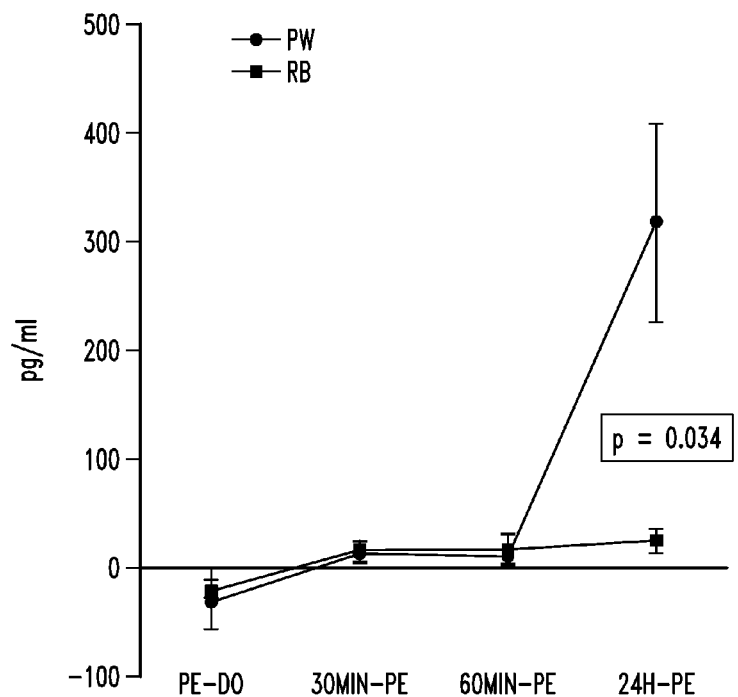

FIG. 55 shows that RB consumption prevents the rise in BDNF plasma concentration 24 hours after the exercise trial. Picograms/milliliter (pg/ml) of BDNF is plotted on the Y-axis.

Figure 56:
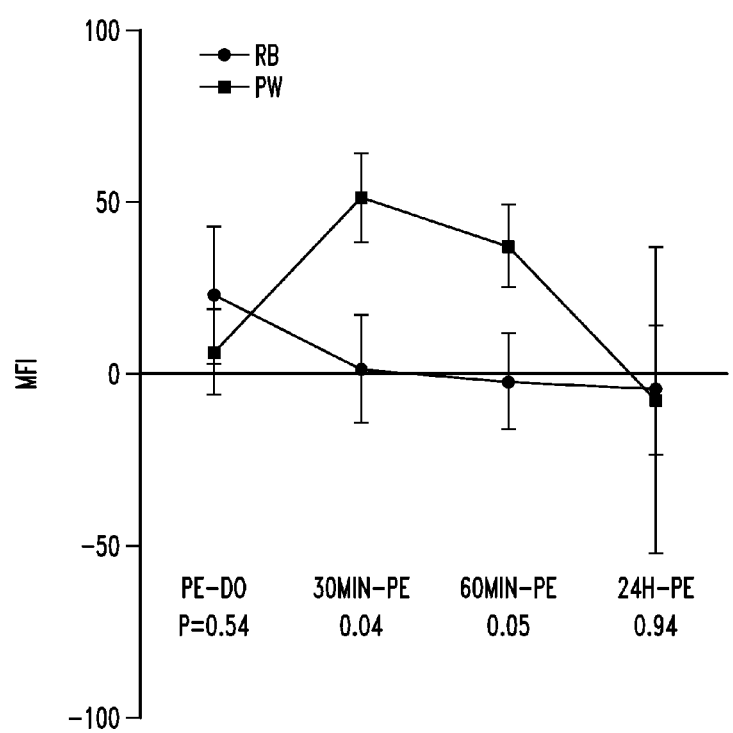

FIG. 56 shows the effect of RB consumption on circulating sCD40L levels. Mean fluorescence intensity units (MFI) are plotted on the Y-axis.

SUMMARY OF EXEMPLARY EMBODIMENTS

Particular aspects provide methods for enhancing exercise performance, comprising administering to a subject in need thereof, an electrokinetically altered aqueous fluid comprising an ionic aqueous solution of charge-stabilized oxygen-containing nanostructures predominantly having an average diameter of less than 100 nanometers and stably configured in the ionic aqueous solution in an amount sufficient to provide for enhancing at least one of exercise performance and recovery time, wherein a method for enhancing exercise performance is afforded.

In certain method aspects, enhancing exercise performance comprises reducing exercise-induced increases of plasma inflammatory cytokine levels in the subject. In particular aspects, the exercise-induced plasma inflammatory cytokine is one selected from the group consisting of interferon-alpha (IFN-alpha), epithelial neutrophil activating protein 78 (ENA-78), and brain-derived neurotrophic factor (BDNF).

In particular method aspects, enhancing exercise performance comprises at least one of preventing or ameliorating exercise-mediated muscle and/or tendon damage and enhancing muscle and/or tendon recovery therefrom (e.g., comprises at least one of preventing or alleviating extent of muscle fiber micro-injury, and enhancing recovery therefrom; comprises reducing biomarkers of exercise-induced muscle injury (e.g., creatine kinase (CK), plasma myoglobin); or comprises ameliorating or enhancing recovering from at least one of exercise induced tendinosis, tendonitis, tenosynovitis, avulsion, and tendon strain associated with chronic, repetitive movement).

In certain aspects, enhancing exercise performance comprises at least one of: increasing the maximum amount of oxygen that the subject can utilize during intense or maximal exercise ($VO_2$ max); decreasing the rating of perceived exertion (RPE); reducing exercise-mediated increase blood lactate levels; preserving muscle contractile function, preferably maximal force or joint ROM; reducing muscle soreness; and ameliorating the onset of fatigue in response to exercise in the subject.

In particular method aspects, the exercise comprises at least one of intense exercise, eccentric exercise, exercise in elevated ambient temperature, repetitive exercise, aerobic exercise, and high altitude exercise.

In certain aspects, the electrokinetically altered aqueous fluid is superoxygenated (e.g., wherein, the electrokinetically-altered aqueous fluid comprises oxygen in an amount of at least 15, ppm, at least 25 ppm, at least 30 ppm, at least 40 ppm, at least 50 ppm, or at least 60 ppm oxygen at atmospheric pressure)

In certain aspects, the ionic aqueous solution comprises a saline solution, and may comprise at least one ion or salt disclosed in Tables 1 an 2 herein.

In particular aspects, the charge-stabilized oxygen-containing nanostructures are stably configured in the ionic aqueous fluid in an amount sufficient to provide, upon contact of a living cell by the fluid, modulation of at least one of cellular membrane potential and cellular membrane conductivity. In particular aspects, the ability to modulate of at least one of cellular membrane potential and cellular membrane conductivity persists for at least two, at least three, at least four, at least five, at least 6, at least 12 months, or longer periods, in a closed gas-tight container, optimally at about 4° C. In certain aspects, modulation of at least one of cellular membrane potential and cellular membrane conductivity comprises altering of a conformation, ligand binding activity, or a catalytic activity of a membrane associated protein. In certain aspects, modulation of at least one of cellular membrane potential and cellular membrane conductivity, comprises modulating whole-cell conductance. In particular aspects, modulation of at least one of cellular membrane potential and cellular membrane conductivity comprises modulation of at least one of: a calcium dependant cellular messaging pathway or system; phospholipase C activity; and adenylate cyclase (AC) activity.

In particular embodiments, administering the electrokinetically altered aqueous fluid comprises oral administration of an aqueous solution or sports beverage (e.g., a sports beverage comprising a sugar, carbohydrate, electrolyte or other sports beverage ingredient).

Additional aspects provide improved methods for producing an electrokinetically-altered oxygenated aqueous fluid or solution, comprising: providing a flow of aqueous fluid material between two spaced surfaces defining a mixing volume therebetween; and introducing oxygen gas into the flowing aqueous fluid material, at or substantially at the temperature of highest density of the aqueous fluid material, within the mixing volume under conditions suitable to infuse at least 20 ppm gas into the material in less than 400 milliseconds, wherein an electrokinetically altered aqueous fluid comprising an ionic aqueous solution of charge-stabilized oxygen-containing nanostructures predominantly having an average diameter of less than 100 nanometers and stably configured in the ionic aqueous fluid is provided. In particular aspects, the dwell time of the flowing material within the mixing volume is greater than 0.06 seconds or greater than 0.1 seconds. In certain aspects, the ratio of surface area to the volume is at least 12, at least 20, at least 30, at least 40, or at least 50.

Yet additional aspects provide improved methods for producing an electrokinetically-altered oxygenated aqueous fluid or solution, comprising use of a mixing device for creating an output mixture by mixing a first aqueous material and a second material, the device comprising: a first chamber configured to receive the first aqueous material from a source of the first aqueous material; a stator; a rotor having an axis of rotation, the rotor being disposed inside the stator and configured to rotate about the axis of rotation therein, at least one of the rotor and stator having a plurality of through-holes; a mixing chamber defined between the rotor and the stator, the mixing chamber being in fluid communication with the first chamber and configured to receive the first aqueous material therefrom, and oxygen being provided to the mixing chamber via the plurality of through-holes formed in the one of the rotor and stator; a second chamber in fluid communication with the mixing chamber and configured to receive the output material therefrom; and a first internal pump housed inside the first chamber, the first internal pump being configured to pump the first aqueous material from the first chamber into the mixing chamber, at or substantially at the temperature of highest density of the aqueous fluid material, wherein an electrokinetically altered aqueous fluid comprising an ionic aqueous solution of charge-stabilized oxygen-containing nanostructures predominantly having an average diameter of less than 100 nanometers and stably configured in the ionic aqueous fluid is provided.

Further aspects provide improved methods for producing an electrokinetically-altered oxygenated aqueous fluid or solution, comprising use of a mixing device for creating an output mixture by mixing a first aqueous material and a second material, the device comprising: a stator; a rotor having an axis of rotation, the rotor being disposed inside the stator and configured to rotate about the axis of rotation therein; a mixing chamber defined between the rotor and the stator, the mixing chamber having an open first end through which the first aqueous material enters the mixing chamber at or substantially at the temperature of highest density of the aqueous fluid material, and an open second end through which the output material exits the mixing chamber, the second material, oxygen gas, entering the mixing chamber through at least one of the rotor and the stator; a first chamber in communication with at least a majority portion of the open first end of the mixing chamber; and a second chamber in communication with the open second end of the mixing chamber, to electrokinetically alter the aqueous material, wherein an electrokinetically altered aqueous fluid comprising an ionic aqueous solution of charge-stabilized oxygen-containing nanostructures predominantly having an average diameter of less than 100 nanometers and stably configured in the ionic aqueous fluid is provided.

In particular aspects of the methods, the first internal pump is configured to impart a circumferential velocity into the aqueous material before it enters the mixing chamber.

Yet further aspects provide methods for producing an electrokinetically-altered oxygenated aqueous fluid or solution in an arcuate mixing chamber formed between two contoured surfaces to create an output mixture, the arcuate mixing chamber having a first end portion opposite a second end portion, the method comprising: providing a first aqueous material; introducing the first aqueous material into the first end portion of the arcuate mixing chamber, at or substantially at the temperature of highest density of the aqueous fluid material, in a flow direction having a first component that is substantially tangent to the arcuate mixing chamber and a second component that is directed toward the second end portion; and introducing oxygen gas into the arcuate mixing chamber though at least one of the two contoured surfaces between the first end portion of the arcuate mixing chamber and the second end portion of the arcuate mixing chamber, wherein an electrokinetically altered aqueous fluid comprising an ionic aqueous solution of charge-stabilized oxygen-containing nanostructures predominantly having an average diameter of less than 100 nanometers and stably configured in the ionic aqueous fluid is provided. In particular embodiments, the first end portion of the mixing chamber is coupled to a first chamber, the method further comprising: before introducing the first aqueous material into the first end portion of the arcuate mixing chamber, introducing the first aqueous material into the first chamber, and imparting a circumferential flow into said material in the first chamber. In further embodiments, the first end portion of the mixing chamber is coupled to a first chamber, the mixing chamber is formed between an outer contoured surface of a rotating cylindrical rotor and an inner contoured surface of a stationary cylindrical stator, and the rotor rotates inside the stator about an axis of rotation, the method further comprising: before introducing the first aqueous material into the first end portion of the arcuate mixing chamber, introducing the first aqueous material into the first chamber, and imparting a circumferential flow substantially about an axis of rotation into said material in the first chamber; introducing oxygen gas into a hollow portion of a rotating rotor having a plurality of through-holes, each through-hole of the plurality extending from the hollow portion to the outer contoured surface of the rotor; flowing the oxygen gas from the hollow portion of the rotating rotor through the plurality of through-holes into the mixing chamber; flowing the aqueous material from the first chamber into the mixing chamber; and rotating the rotor relative to the stator thereby mixing aqueous material and the oxygen gas together inside the mixing chamber.

In further aspects of all of the above methods, the aqueous fluid material comprises at least one salt or ion from Tables 1 and 2 disclosed herein.

In certain embodiments, the methods comprises production of a sports or exercise beverage, or of a component thereof.

DETAILED DESCRIPTION OF THE INVENTION

Provided are methods for enhancing exercise performance, comprising administering electrokinetically altered aqueous fluids comprising an ionic aqueous solution of charge-stabilized oxygen-containing nanostructures predominantly having an average diameter of less than 100 nanometers and stably configured in the ionic aqueous solution. In certain aspects, enhancing exercise performance comprises: reducing plasma inflammatory cytokines (e.g., IFN-alpha, ENA-78 and BDNF); and/or ameliorating exercise-mediated muscle/tendon damage and enhancing muscle/tendon recovery; and/or reducing biomarkers of exercise-induced muscle injury (e.g., CK, plasma myoglobin); and/or ameliorating or enhancing recovering from exercise induced tendinosis, tendonitis, tenosynovitis, avulsion, and tendon strain associated with chronic repetitive movement; and/or increasing $VO_2$ max; and/or decreasing RPE; reducing blood lactate levels; and/or preserving muscle contractile function (e.g., maximal force or joint ROM); and/or reducing muscle soreness; and/or ameliorating the onset of fatigue in response to exercise in the subject. In particular method aspects, the exercise comprises at least one of intense exercise, eccentric exercise, exercise in elevated ambient temperature, repetitive exercise, aerobic exercise, and high altitude exercise. Improved methods for producing electrokinetically altered aqueous fluids (including sports beverages) are also provided.

Provided are electrokinetically-altered fluid sports beverage compositions, comprising an electrokinetically-altered aqueous fluid comprising an ionic aqueous solution of charge-stabilized oxygen-containing nanostructures substantially having an average diameter of less than about 100 nanometers and stably configured in the ionic aqueous fluid in an amount sufficient to provide for enhancing at least one of physiological performance and recovery time. In certain aspects, the charge-stabilized oxygen-containing nanostructures are stably configured in the ionic aqueous fluid in an amount sufficient to provide, upon contact of a living cell by the fluid, modulation of at least one of cellular membrane potential and cellular membrane conductivity. In certain aspects, the charge-stabilized oxygen-containing nanostructures are the major charge-stabilized gas-containing nanostructure species in the fluid. In particular aspects, the percentage of dissolved oxygen molecules present in the fluid as the charge-stabilized oxygen-containing nanostructures is a percentage selected from the group consisting of greater than: 0.01%, 0.1%, 1%, 5%; 10%; 15%; 20%; 25%; 30%; 35%; 40%; 45%; 50%; 55%; 60%; 65%; 70%; 75%; 80%; 85%; 90%; and 95%. In certain embodiments, the total dissolved gas is substantially present in the charge-stabilized gas-containing nanostructures. In certain aspects, the charge-stabilized gas-containing nanostructures substantially have an average diameter of less than a size selected from the group consisting of: 90 nm; 80 nm; 70 nm; 60 nm; 50 nm; 40 nm; 30 nm; 20 nm; 10 nm; and less than 5 nm.

In particular aspects, the ionic aqueous solution comprises a saline solution. In certain aspects, the fluid is super-oxygenated.

In certain embodiments, the charge-stabilized gas-containing nanostructures comprise at least one ion or salt disclosed in Tables 1 an 2 herein, or at least one ion selected from the group consisting of alkali metal based salts including Li+, Na+, K+, Rb+, and Cs+, alkaline earth based salts including Mg++ and Ca++, and transition metal-based positive ions including Cr, Fe, Co, Ni, Cu, and Zn, in each case along with any suitable counterionic components.

In certain aspects, the fluid comprises at least one of a form of solvated electrons, and an electrokinetically modified or charged oxygen species. In certain aspects, the form of solvated electrons or electrokinetically modified or charged oxygen species are present in an amount of at least 0.01 ppm, at least 0.1 ppm, at least 0.5 ppm, at least 1 ppm, at least 3 ppm, at least 5 ppm, at least 7 ppm, at least 10 ppm, at least 15 ppm, or at least 20 ppm. In certain aspects, the electrokinetically-altered fluid comprises a form of solvated electrons stabilized, at least in part, by molecular oxygen.

In particular aspects, the ability to modulate of at least one of cellular membrane potential and cellular membrane conductivity persists for at least two, at least three, at least four, at least five, at least 6, at least 12 months, or longer periods, in a closed gas-tight container, optimally at about 4° C.

In certain aspects, alteration of the electrokinetically altered aqueous fluid comprises exposure of the fluid to hydrodynamically-induced, localized electrokinetic effects. In certain aspects, exposure to the localized electrokinetic effects comprises exposure to at least one of voltage pulses and current pulses. In certain aspects, the exposure of the fluid to hydrodynamically-induced, localized electrokinetic effects, comprises exposure of the fluid to electrokinetic effect-inducing structural features of a device used to generate the fluid.

In certain embodiments, modulation of at least one of cellular membrane potential and cellular membrane conductivity comprises altering of a conformation, ligand binding activity, or a catalytic activity of a membrane associated protein. In certain aspects, the membrane associated protein comprises at least one selected from the group consisting of receptors, transmembrane receptors, ion channel proteins, intracellular attachment proteins, cellular adhesion proteins, integrins, etc. In certain aspects, the transmembrane receptor comprises a G-Protein Coupled Receptor (GPCR). In particular aspects, the G-Protein Coupled Receptor (GPCR) interacts with a G protein a subunit. In certain aspects, the G protein α subunit comprises at least one selected from the group consisting of $G\alpha_s$, $G\alpha_i$, $G\alpha_q$, and $G\alpha_{12}$ (e.g., wherein the G protein α subunit is $G\alpha_q$).

In certain aspects, modulation of at least one of cellular membrane potential and cellular membrane conductivity, comprises modulating whole-cell conductance. In particular aspects, modulating whole-cell conductance, comprises modulating at least one of a linear or non-linear voltage-dependent contribution of the whole-cell conductance.

In certain embodiments, modulation of at least one of cellular membrane potential and cellular membrane conductivity comprises modulation of a calcium dependant cellular messaging pathway or system. In certain aspects, modulation of at least one of cellular membrane potential and cellular membrane conductivity comprises modulation of phospholipase C activity. In certain aspects, modulation of at least one of cellular membrane potential and cellular membrane conductivity comprises modulation of adenylate cyclase (AC) activity.

In certain aspects, the electrokinetically-altered sports beverage composition comprises dissolved oxygen in an amount of at least 8 ppm, at least 15, ppm, at least 25 ppm, at least 30 ppm, at least 40 ppm, at least 50 ppm, or at least 60 ppm oxygen at atmospheric pressure. In certain aspects, the gas in the charge-stabilized nanostructures of the fluid or solution is present in an amount of at least 25 ppm.

Additionally provided are methods for producing a sports beverage composition, comprising: providing a sports beverage fluid formulation or composition; providing a flow of the sports beverage fluid formulation or composition material between two spaced surfaces in relative motion and defining a mixing volume therebetween, wherein the dwell time of a single pass of the flowing fluid material within and through the mixing volume is greater than 0.06 seconds or greater than 0.1 seconds; and introducing oxygen gas into the flowing fluid material within the mixing volume under conditions suitable to dissolve at least 20 ppm, at least 25 ppm, at least 30, at least 40, at least 50, or at least 60 ppm gas into the material, and electrokinetically alter the fluid material, wherein a sports beverage composition comprising an electrokinetically altered aqueous fluid comprising an ionic aqueous solution of charge-stabilized gas-containing nanostructures substantially having an average diameter of less than about 100 nanometers and stably configured in the ionic aqueous fluid in an amount sufficient to provide for enhancing at least one of physiological performance and recovery time is provided. In certain aspects, the oxygen gas is infused into the material in less than 100 milliseconds, less than 200 milliseconds, less than 300 milliseconds, or less than 400 milliseconds.

Further aspects provide a method of producing a sports beverage composition, comprising: providing a sports beverage fluid formulation or composition; providing a flow of the sports beverage fluid formulation or composition material between two spaced surfaces defining a mixing volume therebetween; and introducing oxygen gas into the flowing material within the mixing volume under conditions suitable to infuse at least 20 ppm, at least 25 ppm, at least 30, at least 40, at least 50, or at least 60 ppm gas into the material in less than 100 milliseconds, less than 200 milliseconds, less than 300 milliseconds, or less than 400 milliseconds, to electrokinetically alter the sports beverage fluid formulation or composition, wherein a sports beverage fluid formulation or composition comprising an electrokinetically altered aqueous fluid comprising an ionic aqueous solution of charge-stabilized gas-containing nanostructures substantially having an average diameter of less than about 100 nanometers and stably configured in the ionic aqueous fluid in an amount sufficient to provide for enhancing at least one of physiological performance and recovery time is provided. In certain aspects, the dwell time of the flowing material within the mixing volume is greater than 0.06 seconds or greater than 0.1 seconds. In certain aspects, the ratio of surface area to the volume is at least 12, at least 20, at least 30, at least 40, or at least 50.

Yet further aspects provide a method of producing a sports beverage composition, comprising use of a mixing device for creating an output mixture by mixing a first material and a second material, the device comprising: providing a sports beverage fluid formulation or composition; a first chamber configured to receive the sports beverage fluid formulation or composition material from a source of the first material; a stator; a rotor having an axis of rotation, the rotor being disposed inside the stator and configured to rotate about the axis of rotation therein, at least one of the rotor and stator having a plurality of through-holes; a mixing chamber defined between the rotor and the stator, the mixing chamber being in fluid communication with the first chamber and configured to receive the sports beverage fluid formulation or composition material therefrom, and oxygen being provided to the mixing chamber via the plurality of through-holes formed in the one of the rotor and stator; a second chamber in fluid communication with the mixing chamber and configured to receive the output material therefrom; and a first internal pump housed inside the first chamber, the first internal pump being configured to pump the sports beverage fluid formulation or composition material from the first chamber into the mixing chamber, to electrokinetically alter the sports beverage fluid formulation or composition material, wherein a sports beverage fluid formulation or composition comprising an electrokinetically altered aqueous fluid comprising an ionic aqueous solution of charge-stabilized gas-containing nanostructures substantially having an average diameter of less than about 100 nanometers and stably configured in the ionic aqueous fluid in an amount sufficient to provide for enhancing at least one of physiological performance and recovery time is provided.

Additional aspects provide a method of producing a sports beverage composition, comprising use of a mixing device for creating an output mixture by mixing a first material and a second material, the device comprising: providing a sports beverage fluid formulation or composition; a stator; a rotor having an axis of rotation, the rotor being disposed inside the stator and configured to rotate about the axis of rotation therein; a mixing chamber defined between the rotor and the stator, the mixing chamber having an open first end through which the sports beverage fluid formulation or composition material enters the mixing chamber and an open second end through which the output material exits the mixing chamber, the second material, oxygen gas, entering the mixing chamber through at least one of the rotor and the stator; a first chamber in communication with at least a majority portion of the open first end of the mixing chamber; and a second chamber in communication with the open second end of the mixing chamber, to electrokinetically alter the sports beverage fluid formulation or composition material, wherein a sports beverage fluid formulation or composition material comprising an electrokinetically altered aqueous fluid comprising an ionic aqueous solution of charge-stabilized gas-containing nanostructures substantially having an average diameter of less than about 100 nanometers and stably configured in the ionic aqueous fluid in an amount sufficient to provide for enhancing at least one of physiological performance and recovery time is provided. In certain aspects, the first internal pump is configured to impart a circumferential velocity into the sports beverage fluid formulation or composition material before it enters the mixing chamber.

Yet additional aspects provide a method of producing a sports beverage composition material in an arcuate mixing chamber formed between two contoured surfaces to create an output mixture, the arcuate mixing chamber having a first end portion opposite a second end portion, the method comprising: providing a sports beverage fluid formulation or composition; introducing the sports beverage fluid formulation or composition material into the first end portion of the arcuate mixing chamber in a flow direction having a first component that is substantially tangent to the arcuate mixing chamber and a second component that is directed toward the second end portion; and introducing oxygen gas into the arcuate mixing chamber though at least one of the two contoured surfaces between the first end portion of the arcuate mixing chamber and the second end portion of the arcuate mixing chamber, wherein a sports beverage fluid formulation or composition material comprising an electrokinetically-altered aqueous fluid comprising an ionic aqueous solution of charge-stabilized gas-containing nanostructures substantially having an average diameter of less than about 100 nanometers and stably configured in the ionic aqueous fluid in an amount sufficient to provide for enhancing at least one of physiological performance and recovery time is provided. In certain aspects, the first end portion of the mixing chamber is coupled to a first chamber, the method further comprising: before introducing the sports beverage fluid formulation or composition material into the first end portion of the arcuate mixing chamber, introducing the sports beverage fluid formulation or composition material into the first chamber, and imparting a circumferential flow into said material in the first chamber. In certain aspects, the first end portion of the mixing chamber is coupled to a first chamber, the mixing chamber is formed between an outer contoured surface of a rotating cylindrical rotor and an inner contoured surface of a stationary cylindrical stator, and the rotor rotates inside the stator about an axis of rotation, the method further comprising: before introducing the sports beverage fluid formulation or composition material into the first end portion of the arcuate mixing chamber, introducing the sports beverage fluid formulation or composition material into the first chamber, and imparting a circumferential flow substantially about an axis of rotation into said material in the first chamber; introducing oxygen has into a hollow portion of a rotating rotor having a plurality of through-holes, each through-hole of the plurality extending from the hollow portion to the outer contoured surface of the rotor; flowing the oxygen gas from the hollow portion of the rotating rotor through the plurality of through-holes into the mixing chamber; flowing the sports beverage fluid formulation or composition material from the first chamber into the mixing chamber; and rotating the rotor relative to the stator thereby mixing the sports beverage fluid formulation or composition material and the oxygen gas together inside the mixing chamber.

Further aspects provide an electrokinetically-altered sports beverage composition made according to any of the methods disclosed herein.

In particular aspects, the charge-stabilized oxygen-containing nanostructures of the electrokinetically-alterd fluid comprise at least one salt or ion from Tables 1 and 2 disclosed herein.

In certain aspects, the electrokinetically-altered sports beverage compositions disclosed herein comprise at least one art-recognized sports beverage ingredient. In certain aspects, they comprise a sugar or carbohydrate, and/or caffeine.

Additionally provided are methods for enhancing physiological performance and recovery time, comprising administration, to a subject in need thereof, a electrokinetically-altered sports beverage composition as disclosed herein in an amount sufficient to provide for enhancing at least one of physiological performance and recovery time. In certain aspects, the methods comprise ameliorating the effects of physical exertion of the subject.

Additionally provided are methods for administering a sugar, carbohydrate or other sports beverage ingredient to a subject, comprising orally administering to a subject in need thereof an electrokinetically-altered sports beverage compositions as disclosed herein, and comprising a sugar or carbohydrate, to the subject.

Further aspects provide methods for producing a sports beverage composition material, comprising: obtaining at least one sports beverage ingredient; and combining the least one sports beverage ingredient with an electrokinetically-altered aqueous fluid comprising an ionic aqueous solution of charge-stabilized oxygen-containing nanostructures substantially having an average diameter of less than about 100 nanometers and stably configured in the ionic aqueous fluid in an amount sufficient to provide for enhancing at least one of physiological performance and recovery time. In certain aspects, the at least one sports beverage ingredient comprises a concentrated sports beverage ingredient. In certain aspects, the at least one sports beverage ingredient comprises a solid sports beverage ingredient.

Additional aspects provide a method for preventing muscle damage and/or enhancing/facilitating muscle recovery from exercise (e.g., eccentric exercise), comprising administration, to a subject in need thereof, a electrokinetically-altered sports beverage composition according to any one of claims 1-29 in an amount sufficient to provide for preventing muscle damage and/or enhancing/facilitating muscle recovery from exercise. In particular aspects, the methods involve reducing biomarkers of exercise-induced muscle injury (e.g., creatine kinase (CK)). In further aspects, the methods comprise reducing subjective ratings of muscle soreness. In particular aspects, the methods comprise preserving muscle contractile function (e.g., maximal force, joint ROM). In certain aspects, the methods comprise improving exercise performance.

Additionally provided are methods for preventing exercise-induced tendon damage and/or enhancing/facilitating tendon recovery from exercise and/or exercise-induced damage and/or surgery, comprising administration, to a subject in need thereof, a electrokinetically-altered sports beverage composition as disclosed herein in an amount sufficient to provide for preventing exercise-induced tendon damage and/or enhancing/facilitating tendon recovery from exercise and/or exercise-induced damage and/or surgery. In certain aspects, the methods comprise preventing or ameliorating at least one of exercise-induced tendinosis, tendonitis, tenosynovitis, and avulsion.

Further provided are methods for preventing and/or ameliorating and/or enhancing recovery from tendon strain associated with chronic, repetitive movement, comprising administration, to a subject in need thereof, a electrokinetically-altered sports beverage as disclosed herein in an amount sufficient to provide for preventing and/or ameliorating and/or enhancing recovery from tendon strain associated with chronic, repetitive movement.

Electrokinetically-generated Fluids:

"Electrokinetically generated fluid," as used herein, refers to Applicants' inventive electrokinetically-generated fluids generated, for purposes of the working Examples herein, by the exemplary Mixing Device described in detail herein (see also US2008/02190088 (now U.S. Pat. No. 7,832,920), US2008/0281001 (now U.S. Pat. No. 7,919,534); US2010/0038244, WO2008/052143, US2009/0227018; WO2009/055614, and US20100029764 (all incorporated herein by reference in their entirety for their teachings regarding the nature and biological activities of electrokinetically-altered fluids). The electrokinetic fluids, as demonstrated by the data disclosed and presented herein, represent novel and fundamentally distinct fluids relative to prior art non-electrokinetic fluids, including relative to prior art oxygenated non-electrokinetic fluids (e.g., pressure pot oxygenated fluids and the like). As disclosed in various aspects herein, the electrokinetically-generated fluids have unique and novel physical and biological properties including, but not limited to the following:

In particular aspects, the electrokinetically altered aqueous fluid comprise an ionic aqueous solution of charge-stabilized oxygen-containing nanostructures substantially having an average diameter of less than about 100 nanometers and stably configured in the ionic aqueous fluid in an amount sufficient to provide, upon contact of a living cell by the fluid, modulation of at least one of cellular membrane potential and cellular membrane conductivity.

In particular aspects, electrokinetically-generated fluids refers to fluids generated in the presence of hydrodynamically-induced, localized (e.g., non-uniform with respect to the overall fluid volume) electrokinetic effects (e.g., voltage/current pulses), such as device feature-localized effects as described herein. In particular aspects said hydrodynamically-induced, localized electrokinetic effects are in combination with surface-related double layer and/or streaming current effects as disclosed and discussed herein.

In particular aspects the administered inventive electrokinetically-altered fluids comprise charge-stabilized oxygen-containing nanostructures in an amount sufficient to provide modulation of at least one of cellular membrane potential and cellular membrane conductivity. In certain embodiments, the electrokinetically-altered fluids are superoxygenated (e.g., RNS-20, RNS-40 and RNS-60, comprising 20 ppm, 40 ppm and 60 ppm dissolved oxygen, respectively, in standard saline). In particular embodiments, the electrokinetically-altered fluids are not-superoxygenated (e.g., RNS-10 or Solas, comprising 10 ppm (e.g., approx. ambient levels of dissolved oxygen in standard saline). In certain aspects, the salinity, sterility, pH, etc., of the inventive electrokinetically-altered fluids is established at the time of electrokinetic production of the fluid, and the sterile fluids are administered by an appropriate route. Alternatively, at least one of the salinity, sterility, pH, etc., of the fluids is appropriately adjusted (e.g., using sterile saline or appropriate diluents) to be physiologically compatible with the route of administration prior to administration of the fluid. Preferably, and diluents and/or saline solutions and/or buffer compositions used to adjust at least one of the salinity, sterility, pH, etc., of the fluids are also electrokinetic fluids, or are otherwise compatible.

In particular aspects, the inventive electrokinetically-altered fluids comprise saline (e.g., one or more dissolved salt(s); e.g., alkali metal based salts (Li+, Na+, K+, Rb+, Cs+, etc.), alkaline earth based salts (e.g., Mg++, Ca++), etc., or transition metal-based positive ions (e.g., Cr, Fe, Co, Ni, Cu, Zn, etc.,), in each case along with any suitable anion components, including, but not limited to F−, Cl−, Br−, I−, PO4−, SO4−, and nitrogen-based anions. Particular aspects comprise mixed salt based electrokinetic fluids (e.g., Na+, K+, Ca++, Mg++, transition metal ion(s), etc.) in various combinations and concentrations, and optionally with mixtures of counterions. In particular aspects, the inventive electrokinetically-altered fluids comprise standard saline (e.g., approx. 0.9% NaCl, or about 0.15 M NaCl). In particular aspects, the inventive electrokinetically-altered fluids comprise saline at a concentration of at least 0.0002 M, at least 0.0003 M, at least 0.001 M, at least 0.005 M, at least 0.01 M, at least 0.015 M, at least 0.1 M, at least 0.15 M, or at least 0.2 M. In particular aspects, the conductivity of the inventive electrokinetically-altered fluids is at least 10 µS/cm, at least 40 µS/cm, at least 80 µS/cm, at least 100 µS/cm, at least 150 µS/cm, at least 200 µS/cm, at least 300 µS/cm, or at least 500 µS/cm, at least 1 mS/cm, at least 5, mS/cm, 10 mS/cm, at least 40 mS/cm, at least 80 mS/cm, at least 100 mS/cm, at least 150 mS/cm, at least 200 mS/cm, at least 300 mS/cm, or at least 500 mS/cm. In particular aspects, any salt may be used in preparing the inventive electrokinetically-altered fluids, provided that they allow for formation of biologically active salt-stabilized nanostructures (e.g., salt-stabilized oxygen-containing nanostructures) as disclosed herein.

According to particular aspects, the biological effects of the inventive fluid compositions comprising charge-stabilized gas-containing nanostructures can be modulated (e.g., increased, decreased, tuned, etc.) by altering the ionic components of the fluids, and/or by altering the gas component of the fluid.

According to particular aspects, the biological effects of the inventive fluid compositions comprising charge-stabilized gas-containing nanostructures can be modulated (e.g., increased, decreased, tuned, etc.) by altering the gas component of the fluid. In preferred aspects, oxygen is used in preparing the inventive electrokinetic fluids. In additional aspects mixtures of oxygen along with at least one other gas selected from Nitrogen, Oxygen, Argon, Carbon dioxide, Neon, Helium, krypton, hydrogen and Xenon. As described above, the ions may also be varied, including along with varying the gas constituent(s).

Given the teachings and assay systems disclosed herein (e.g., cell-based cytokine assays, $VO_2$ max assays, RPE (rating of perceived exertion) assays, lactate assays, etc.) one of skill in the art will readily be able to select appropriate salts and concentrations thereof to achieve the biological activities disclosed herein.

TABLE 1

Exemplary cations and anions.

| Name | Formula | Other name(s) |
|---|---|---|
| Exemplary Cations: | | |
| Aluminum | $Al^{+3}$ | |
| Ammonium | $NH_4^+$ | |
| Barium | $Ba^{+2}$ | |
| Calcium | $Ca^{+2}$ | |
| Chromium(II) | $Cr^{+2}$ | Chromous |
| Chromium(III) | $Cr^{+3}$ | Chromic |
| Copper(I) | $Cu^+$ | Cuprous |
| Copper(II) | $Cu^{+2}$ | Cupric |
| Iron(II) | $Fe^{+2}$ | Ferrous |
| Iron(III) | $Fe^{+3}$ | Ferric |
| Hydrogen | $H^+$ | |
| Hydronium | $H_3O^+$ | |
| Lead(II) | $Pb^{+2}$ | |
| Lithium | $Li^+$ | |
| Magnesium | $Mg^{+2}$ | |
| Manganese(II) | $Mn^{+2}$ | Manganous |
| Manganese(III) | $Mn^{+3}$ | Manganic |
| Mercury(I) | $Hg_2^{+2}$ | Mercurous |
| Mercury(II) | $Hg^{+2}$ | Mercuric |
| Nitronium | $NO_2^+$ | |
| Potassium | $K^+$ | |
| Silver | $Ag^+$ | |
| Sodium | $Na^+$ | |
| Strontium | $Sr^{+2}$ | |
| Tin(II) | $Sn^{+2}$ | Stannous |
| Tin(IV) | $Sn^{+4}$ | Stannic |
| Zinc | $Zn^{+2}$ | |
| Exemplary Anions: | | |
| Simple ions: | | |
| Hydride | $H^-$ | Oxide $O^{2-}$ |
| Fluoride | $F^-$ | Sulfide $S^{2-}$ |
| Chloride | $Cl^-$ | Nitride $N^{3-}$ |
| Bromide | $Br^-$ | |
| Iodide | $I^-$ | |
| Oxoanions: | | |
| Arsenate | $AsO_4^{3-}$ | Phosphate $PO_4^{3-}$ |
| Arsenite | $AsO_3^{3-}$ | Hydrogen phosphate $HPO_4^{2-}$ |
| | | Dihydrogen phosphate $H_2PO_4^-$ |
| Sulfate | $SO_4^{2-}$ | Nitrate $NO_3^-$ |
| Hydrogen sulfate | $HSO_4^-$ | Nitrite $NO_2^-$ |
| Thiosulfate | $S_2O_3^{2-}$ | |
| Sulfite | $SO_3^{2-}$ | |
| Perchlorate | $ClO_4^-$ | Iodate $IO_3^-$ |
| Chlorate | $ClO_3^-$ | Bromate $BrO_3^-$ |
| Chlorite | $ClO_2^-$ | |
| Hypochlorite | $OCl^-$ | Hypobromite $OBr^-$ |
| Carbonate | $CO_3^{2-}$ | Chromate $CrO_4^{2-}$ |
| Hydrogen carbonate or Bicarbonate | $HCO_3^-$ | Dichromate $Cr_2O_7^{2-}$ |
| Anions from Organic Acids: | | |
| Acetate | $CH_3COO^-$ | formate $HCOO^-$ |
| Others: | | |
| Cyanide | $CN^-$ | Amide $NH_2^-$ |
| Cyanate | $OCN^-$ | Peroxide $O_2^{2-}$ |
| Thiocyanate | $SCN^-$ | Oxalate $C_2O_4^{2-}$ |
| Hydroxide | $OH^-$ | Permanganate $MnO_4^-$ |

TABLE 2

Exemplary cations and anions.

| Formula | Charge | Name |
|---|---|---|
| Monoatomic Cations | | |
| $H^+$ | 1+ | hydrogen ion |
| $Li^+$ | 1+ | lithium ion |
| $Na^+$ | 1+ | sodium ion |
| $K^+$ | 1+ | potassium ion |
| $Cs^+$ | 1+ | cesium ion |
| $Ag^+$ | 1+ | silver ion |
| $Mg^{2+}$ | 2+ | magnesium ion |
| $Ca^{2+}$ | 2+ | calcium ion |
| $Sr^{2+}$ | 2+ | strontium ion |
| $Ba^{2+}$ | 2+ | barium ion |
| $Zn^{2+}$ | 2+ | zinc ion |
| $Cd^{2+}$ | 2+ | cadmium ion |
| $Al^{3+}$ | 3+ | aluminum ion |
| Polyatomic Cations | | |
| $NH_4^+$ | 1+ | ammonium ion |
| $H_3O^+$ | 1+ | hydronium ion |
| Multivalent Cations | | |
| $Cr^{2+}$ | 2 | chromium(II) or chromous ion |
| $Cr^{3+}$ | 3 | chromium(III) or chromic ion |
| $Mn^{2+}$ | 2 | manganese(II) or manganous ion |
| $Mn^{4+}$ | 4 | manganese(IV) ion |
| $Fe^{2+}$ | 2 | iron(II) or ferrous ion |
| $Fe^{3+}$ | 3 | iron(III) or ferric ion |
| $Co^{2+}$ | 2 | cobalt(II) or cobaltous ion |
| $Co^{3+}$ | 3 | cobalt(III) or cobaltic ion |
| $Ni^{2+}$ | 2 | nickel(II) or nickelous ion |
| $Ni^{3+}$ | 3 | nickel(III) or nickelic ion |
| $Cu^+$ | 1 | copper(I) or cuprous ion |
| $Cu^{2+}$ | 2 | copper(II) or cupric ion |
| $Sn^{2+}$ | 2 | tin(II) or atannous ion |
| $Sn^{4+}$ | 4 | tin(IV) or atannic ion |
| $Pb^{2+}$ | 2 | lead(II) or plumbous ion |
| $Pb^{4+}$ | 4 | lead(IV) or plumbic ion |
| Monoatomic Anions | | |
| $H^-$ | 1− | hydride ion |
| $F^-$ | 1− | fluoride ion |
| $Cl^-$ | 1− | chloride ion |
| $Br^-$ | 1− | bromide ion |
| $I^-$ | 1− | iodide ion |
| $O^{2-}$ | 2− | oxide ion |
| $S^{2-}$ | 2− | sulfide ion |
| $N^{3-}$ | 3− | nitride ion |
| Polyatomic Anions | | |
| $OH^-$ | 1− | hydroxide ion |
| $CN^-$ | 1− | cyanide ion |
| $SCN^-$ | 1− | thiocyanate ion |
| $C_2H_3O_2^-$ | 1− | acetate ion |
| $ClO^-$ | 1− | hypochlorite ion |
| $ClO_2^-$ | 1− | chlorite ion |
| $ClO_3^-$ | 1− | chlorate ion |
| $ClO_4^-$ | 1− | perchlorate ion |
| $NO_2^-$ | 1− | nitrite ion |
| $NO_3^-$ | 1− | nitrate ion |
| $MnO_4^-$ | 2− | permanganate ion |
| $CO_3^{2-}$ | 2− | carbonate ion |
| $C_2O_4^{2-}$ | 2− | oxalate ion |
| $CrO_4^{2-}$ | 2− | chromate ion |
| $Cr_2O_7^{2-}$ | 2− | dichromate ion |
| $SO_3^{2-}$ | 2− | sulfite ion |
| $SO_4^{2-}$ | 2− | sulfate ion |
| $PO_3^{3-}$ | 3− | phosphite ion |
| $PO_4^{3-}$ | 3− | phosphate ion |

The present disclosure sets forth novel electrokinetically-generated gas-enriched fluids, including, but not limited to electrokinetically-generated gas-enriched water, ionic water, aqueous solutions, beverages, sports drinks, energy drinks, food drinks, aqueous saline solutions (e.g., standard aqueous saline solutions, and other saline solutions as discussed herein and as would be recognized in the art, including any physiological compatible saline solutions).

In particular aspects, the electrokinetically altered aqueous fluids are suitable to modulate $^{13}$C-NMR line-widths of reporter solutes (e.g., trehalose) dissolved therein. NMR line-width effects are in indirect method of measuring, for example, solute 'tumbling' in a test fluid as described herein in particular working Examples.

In particular aspects, the electrokinetically altered aqueous fluids are characterized by at least one of: distinctive square wave voltametry peak differences at any one of −0.14V, −0.47V, −1.02V and −1.36V; polarographic peaks at −0.9 volts; and an absence of polarographic peaks at −0.19 and −0.3 volts, which are unique to the electrokinetically generated fluids as disclosed herein in particular working Examples.

In particular aspects, the electrokinetically altered aqueous fluids are suitable to alter at least one of cellular membrane potential and cellular membrane conductivity (e.g., a voltage-dependent contribution of the whole-cell conductance as measure in patch clamp studies disclosed herein).

In particular aspects, the electrokinetically altered aqueous fluids are gasified (e.g., oxygenated), wherein the gas (e.g., oxygen) in the fluid is present in an amount of at least 15, ppm, at least 25 ppm, at least 30 ppm, at least 40 ppm, at least 50 ppm, or at least 60 ppm dissolved gas (e.g., oxygen) at atmospheric pressure. In particular aspects, the electrokinetically altered aqueous fluids have less than 15 ppm, less that 10 ppm of dissolved gas (e.g., oxygen) at atmospheric pressure, or approximately ambient oxygen levels.

In particular aspects, the electrokinetically altered aqueous fluids are oxygenated, wherein the gas (e.g., oxygen) in the fluid is present in an amount between approximately 8 ppm and approximately 15 ppm, and in this case is sometimes referred to herein as "Solas" or Solas-based fluids.

In particular aspects, the electrokinetically altered aqueous fluid comprises at least one of solvated electrons (e.g., stabilized by molecular oxygen), and electrokinetically modified and/or charged gas (e.g., oxygen) species, and wherein in certain embodiments the solvated electrons and/or electrokinetically modified or charged gas (e.g., oxygen)(species are present in an amount of at least 0.01 ppm, at least 0.1 ppm, at least 0.5 ppm, at least 1 ppm, at least 3 ppm, at least 5 ppm, at least 7 ppm, at least 10 ppm, at least 15 ppm, or at least 20 ppm.

In particular aspects, the electrokinetically altered aqueous fluids are suitable to alter cellular membrane structure or function (e.g., altering of a conformation, ligand binding activity, or a catalytic activity of a membrane associated protein) sufficient to provide for modulation of intracellular signal transduction, wherein in particular aspects, the membrane associated protein comprises at least one selected from the group consisting of receptors, transmembrane receptors (e.g., G-Protein Coupled Receptor (GPCR), TSLP receptor, beta 2 adrenergic receptor, bradykinin receptor, etc.), ion channel proteins, intracellular attachment proteins, cellular adhesion proteins, and integrins. In certain aspects, the effected G-Protein Coupled Receptor (GPCR) interacts with a G protein α subunit (e.g., $G\alpha_s$, $G\alpha_i$, $G\alpha_q$, and $G\alpha_{12}$).

In particular aspects, the electrokinetically altered aqueous fluids are suitable to modulate intracellular signal transduction, comprising modulation of a calcium dependant cellular messaging pathway or system (e.g., modulation of phospholipase C activity, or modulation of adenylate cyclase (AC) activity).

In particular aspects, the electrokinetically altered aqueous fluids are characterized by various biological activities (e.g., regulation of cytokines, receptors, enzymes and other proteins and intracellular signaling pathways) described in the working Examples and elsewhere herein.

In particular aspects, the electrokinetically altered aqueous fluids reduce DEP-induced TSLP receptor expression in bronchial epithelial cells (BEC).

In particular aspects, the electrokinetically altered aqueous fluids inhibit the DEP-induced cell surface-bound MMP9 levels in bronchial epithelial cells (BEC).

In particular aspects, the physical and biological effects (e.g., the ability to alter cellular membrane structure or function sufficient to provide for modulation of intracellular signal transduction) of the electrokinetically altered aqueous fluids persists for at least two, at least three, at least four, at least five, at least 6 months, or longer periods, in a closed container (e.g., closed gas-tight container), preferably at 4° C.

Therefore, further aspects provide said electrokinetically-generated solutions and methods of producing an electrokinetically altered gasofied (e.g., oxygenated) aqueous fluid or solution, comprising: providing a flow of a fluid material between two spaced surfaces in relative motion and defining a mixing volume therebetween, wherein the dwell time of a single pass of the flowing fluid material within and through the mixing volume is greater than 0.06 seconds or greater than 0.1 seconds; and introducing oxygen ($O_2$) into the flowing fluid material within the mixing volume under conditions suitable to dissolve at least 20 ppm, at least 25 ppm, at least 30, at least 40, at least 50, or at least 60 ppm gas (e.g., oxygen) into the material, and electrokinetically alter the fluid or solution. In certain aspects, the gas (e.g., oxygen) is infused into the material in less than 100 milliseconds, less than 200 milliseconds, less than 300 milliseconds, or less than 400 milliseconds. In particular embodiments, the ratio of surface area to the volume is at least 12, at least 20, at least 30, at least 40, or at least 50.

Yet further aspects, provide a method of producing an electrokinetically altered gasified (e.g., oxygenated) aqueous fluid or solution, comprising: providing a flow of a fluid material between two spaced surfaces defining a mixing volume therebetween; and introducing gas (e.g., oxygen) into the flowing material within the mixing volume under conditions suitable to infuse at least 20 ppm, at least 25 ppm, at least 30, at least 40, at least 50, or at least 60 ppm gas (e.g., oxygen) into the material in less than 100 milliseconds, less than 200 milliseconds, less than 300 milliseconds, or less than 400 milliseconds. In certain aspects, the dwell time of the flowing material within the mixing volume is greater than 0.06 seconds or greater than 0.1 seconds. In particular embodiments, the ratio of surface area to the volume is at least 12, at least 20, at least 30, at least 40, or at least 50.

Additional embodiments provide a method of producing an electrokinetically altered gasified (e.g., oxygenated) aqueous fluid or solution, comprising use of a mixing device for creating an output mixture by mixing a first material and a second material, the device comprising: a first chamber configured to receive the first material from a source of the first material; a stator; a rotor having an axis of rotation, the rotor being disposed inside the stator and configured to rotate about the axis of rotation therein, at least one of the rotor and stator having a plurality of through-holes; a mixing chamber defined between the rotor and the stator, the mixing chamber being in fluid communication with the first chamber and configured to receive the first material therefrom, and the second material being provided to the mixing chamber via the plurality of through-holes formed in the one of the rotor and stator; a second chamber in fluid communication with the mixing chamber and configured to receive the output material therefrom; and a first internal pump housed inside the first chamber, the first internal pump being configured to pump the first material from the first chamber into the mixing chamber. In certain aspects, the first internal pump is configured to impart a circumferential velocity into the first material before it enters the mixing chamber.

Further embodiments provide a method of producing an electrokinetically altered gasified (e.g., oxygenated) aqueous fluid or solution, comprising use of a mixing device for creating an output mixture by mixing a first material and a second material, the device comprising: a stator; a rotor having an axis of rotation, the rotor being disposed inside the stator and configured to rotate about the axis of rotation therein; a mixing chamber defined between the rotor and the stator, the mixing chamber having an open first end through which the first material enters the mixing chamber and an open second end through which the output material exits the mixing chamber, the second material entering the mixing chamber through at least one of the rotor and the stator; a first chamber in communication with at least a majority portion of the open first end of the mixing chamber; and a second chamber in communication with the open second end of the mixing chamber.

Additional aspects provide an electrokinetically altered gasified (e.g., oxygenated) aqueous fluid or solution made according to any of the above methods.

The phrases "enhancing exercise performance" and "enhancing recovery time" refer to, and include but limited to, reversing, alleviating, inhibiting the progress of, or preventing a negative or limiting condition or symptom of exercise (e.g., exercise stress and other variable as discussed and disclosed herein), and/or enhancing a positive or beneficial condition or symptom of exercise and/or enhancing and/or speeding recovery from such negative or limiting conditions or symptoms of exercise (e.g., exercise stress), as various taught and/or defined herein.

The phrases "performance enhancing amount" and "recovery enhancing amount" refer to, and include, administration (or consumption) an amount of the electrokineticially-altered fluids and beverages disclosed herein that is sufficient to reverse, alleviate, inhibit the progress of, or prevent a negative or limiting condition or symptom of exercise (e.g., exercise stress), and/or enhance a positive or beneficial condition or symptom of exercise, and/or enhanced and/or accelerated recovery from such negative or limiting conditions or symptoms of exercise (e.g., exercise stress), as various taught and/or defined herein.

Electrokinetically Gas (e.g., Oxygen)-Enriched Aqueous Fluids and Solutions

In the Figures and Examples that follow, it is to be understood that while oxygen is the preferred gas used in producing the inventive electrokinetic fluids, and the describe biological activities, the present invention encompasses other electrokinetically-altered fluids comprising the use of various positive ions and counter ions as discussed herein above, and including other additives as will be familiar to those of ordinary skill in the beverage art (e.g., sports beverage, energy beverage, etc.). In certain aspects, such electrokinetic fluid variants have the ability to modulate at least one of cellular membrane potential or cellular membrane conductance, and/or modulate at least one biological activity as taught herein with the exemplary oxygen embodiments that comprise charge-stabilized oxygen-containing nanostructures substantially having an average diameter less than about 100 nm.

Charge-stabilized Nanostructures (e.g., Charge Stabilized Oxygen-containing Nanostructures):

As described in detail in US2008/02190088 (now U.S. Pat. No. 7,832,920), US2008/0281001 (now U.S. Pat. No. 7,919, 534); US2010/0038244, WO2008/052143, US2009/ 0227018; WO2009/055614, and US20100029764 (all incorporated herein by reference in their entirety for their teachings regarding the nature and biological activities of electrokinetically-altered fluids, and see particularly under "Double Layer Effect," "Dwell Time," "Rate of Infusion," and "Bubble size Measurements," thereof) the electrokinetic mixing device creates, in a matter of milliseconds, a unique non-linear fluid dynamic interaction of the first material (e.g., water, saline, etc.) and the second material (e.g., gas, such as oxygen, etc.) with complex, dynamic turbulence providing complex mixing in contact with an effectively enormous surface area (including those of the device and of the exceptionally small gas bubbles of less that 100 nm) including certain surface features that provide for the novel electrokinetic effects. The, feature-localized electrokinetic effects have been demonstrated using a specially designed mixing device comprising insulated rotor and stator features (Id).

As well-recognized in the art, charge redistributions and/or solvated electrons are known to be highly unstable in aqueous solution. According to particular aspects, Applicants' electrokinetic effects (e.g., charge redistributions, including, in particular aspects, solvated electrons) are surprisingly stabilized within the output material (e.g., water, saline solutions, ionic solutions, beverage solutions, etc.). In fact, the stability of the properties and biological activity of the inventive electrokinetic fluids can be maintained for months in a gas-tight container (preferably at 4° C., indicating involvement of dissolved gas (e.g., oxygen) in helping to generate and/or maintain, and/or mediate the properties and activities of the inventive solutions. Significantly, the charge redistributions and/or solvated electrons are stably configured in the inventive electrokinetic ionic aqueous fluids in an amount sufficient to provide, upon contact with a living cell (e.g., mammalian cell) by the fluid, modulation of at least one of cellular membrane potential and cellular membrane conductivity (see, e.g., US2009/0227018; WO2009/055614, and US20100029764, all incorporated by reference herein in the entirety for their teachings on the nature and biological activity of electrokinetically-altered fluids).

According to particular aspects, interactions between the water molecules and the molecules of the substances (e.g., oxygen) dissolved in the water change the collective structure of the water and provide for nanoscale structures (e.g., caged oxygen structures or clusters), including charge-stabilized nanostructures comprising oxygen and/or stabilized and/or associated charges (e.g., nanostructures comprising gas along with ions and/or electrons) imparted to the inventive output materials. Without being bound by mechanism, and according to the properties and activities described herein, the configuration of the nanostructures in particular aspects is such that they: comprise (at least for formation and/or stability and/or biological activity) dissolved gas (e.g., oxygen); enable the electrokinetic fluids (e.g., hydration beverages, sports beverages, performance beverages, energy beverages, etc.) to modulate (e.g., impart or receive) charges and/or charge effects (e.g., modulation of membrane potential and/or conductivity) upon contact or sufficient proximity with a cell membrane or related constituent thereof; and in particular aspects provide for stabilization (e.g., carrying, harboring, trapping) solvated electrons and/or electric fields in a biologically-relevant form.

According to particular aspects, in ionic or saline (e.g., water, saline, standard saline, etc.) solutions, the inventive nanostructures comprise charge stabilized nanostructures (e.g., average diameter less that 100 nm) that may comprise at least one dissolved gas molecule (e.g., oxygen) within a charge-stabilized hydration shell. According to additional aspects, and as described elsewhere herein, the charge-stabilized hydration shell may comprise a cage or void harboring the at least one dissolved gas molecule (e.g., oxygen). According to further aspects, by virtue of the provision of suitable charge-stabilized hydration shells, the charge-stabilized nanostructure and/or charge-stabilized oxygen containing nano-structures may additionally comprise a solvated electron (e.g., stabilized solvated electron).

Without being bound by mechanism or particular theory, charge-stabilized microbubbles stabilized by ions in aqueous liquid in equilibrium with ambient (atmospheric) gas have been proposed (Bunkin et al., *Journal of Experimental and Theoretical Physics*, 104:486-498, 2007; incorporated herein by reference in its entirety). According to particular aspects of the present invention, Applicants' novel electrokinetic fluids comprise a novel, biologically active form of charge-stabilized oxygen-containing nanostructures, and may further comprise novel arrays, clusters or associations of such structures.

According to the charge-stabilized microbubble model, the short-range molecular order of the water structure is destroyed by the presence of a gas molecule (e.g., a dissolved gas molecule initially complexed with a nonadsorptive ion provides a short-range order defect), providing for condensation of ionic droplets, wherein the defect is surrounded by first and second coordination spheres of water molecules, which are alternately filled by adsorptive ions (e.g., acquisition of a 'screening shell of $Na^+$ ions to form an electrical double layer) and nonadsorptive ions (e.g., $Cl^-$ ions occupying the second coordination sphere) occupying six and 12 vacancies, respectively, in the coordination spheres. In under-saturated ionic solutions (e.g., undersaturated saline solutions), this hydrated 'nucleus' remains stable until the first and second spheres are filled by six adsorptive and five nonadsorptive ions, respectively, and then undergoes Coulomb explosion creating an internal void containing the gas molecule, wherein the adsorptive ions (e.g., $Na^+$ ions) are adsorbed to the surface of the resulting void, while the nonadsorptive ions (or some portion thereof) diffuse into the solution (Bunkin et al., supra). In this model, the void in the nanostructure is prevented from collapsing by Coulombic repulsion between the ions (e.g., $Na^+$ ions) adsorbed to its surface. The stability of the void-containing nanostructures is postulated to be due to the selective adsorption of dissolved ions with like charges onto the void/bubble surface and diffusive equilibrium between the dissolved gas and the gas inside the bubble, where the negative (outward electrostatic pressure exerted by the resulting electrical double layer provides stable compensation for surface tension, and the gas pressure inside the bubble is balanced by the ambient pressure. According to the model, formation of such microbubbles requires an ionic component, and in certain aspects collision-mediated associations between particles may provide for formation of larger order clusters (arrays) (Id).

The charge-stabilized microbubble model of Bunkin et al., suggests that the particles can be gas microbubbles, but contemplates only spontaneous formation of such structures in ionic solution in equilibrium with ambient air, is uncharacterized and silent as to whether oxygen is capable of forming such structures, how such structures might be further stabilized, and is likewise silent as to whether solvated electrons might be associated and/or stabilized by such structures.

According to particular aspects of the present invention, the inventive electrokinetic fluids comprising charge-stabilized nanostructures and/or charge-stabilized oxygen-containing nanostructures are novel and fundamentally distinct from the postulated non-electrokinetic, atmospheric charge-stabilized microbubble structures according to the microbubble model. Significantly, this conclusion is unavoidable, deriving, at least in part, from the fact that control saline solutions do not have the biological properties disclosed herein, whereas Applicants' charge-stabilized nanostructures provide a novel, biologically active form of charge-stabilized oxygen-containing nanostructures.

According to particular aspects of the present invention, Applicants' novel electrokinetic device and methods provide for novel electrokinetically-altered fluids comprising significant quantities of charge-stabilized nanostructures in excess of any amount that may or may not spontaneously occur in ionic fluids in equilibrium with air, or in any non-electrokinetically generated fluids. In particular aspects, the charge-stabilized nanostructures comprise charge-stabilized oxygen-containing nanostructures. In additional aspects, the charge-stabilized nanostructures are all, or substantially all charge-stabilized oxygen-containing nanostructures, or the charge-stabilized oxygen-containing nanostructures is the major charge-stabilized gas-containing nanostructure species in the electrokinetic fluid.

According to yet further aspects, the charge-stabilized nanostructures and/or the charge-stabilized oxygen-containing nanostructures may comprise or harbor a solvated electron and/or electric field (electric double layer), and thereby provide a novel stabilized solvated electron, or electric field carrier. In particular aspects, the charge-stabilized nanostructures and/or the charge-stabilized oxygen-containing nanostructures provide a novel type of electride (or inverted electride), which in contrast to conventional solute electrides having a single organically coordinated cation, rather have a plurality of cations stably arrayed about a void or a void containing an oxygen atom, wherein the arrayed sodium ions are coordinated by water hydration shells, rather than by organic molecules. According to particular aspects, a solvated electron and or electric field (electric double layer) may be accommodated by the hydration shell of water molecules, or a hydrated electron may be accommodated within the nanostructure void and distributed over all the cations. In certain aspects, therefore, the inventive nanostructures provide a novel 'super electride' structure in solution by not only providing for distribution/stabilization of the solvated electron and/or electric field over multiple arrayed sodium cations, but also providing for association or partial association of a solvated electron with the caged oxygen molecule(s) in the void—the solvated electron distributing over an array of sodium atoms and at least one oxygen atom. According to particular aspects, therefore, 'solvated electrons' in the inventive electrokinetic fluids, may not be solvated in the traditional model comprising direct hydration by water molecules. Alternatively, in limited analogy with dried electride salts, solvated electrons in the inventive electrokinetic fluids may be distributed over multiple charge-stabilized nanostructures to provide a 'lattice glue' to stabilize higher order arrays in aqueous solution.

In particular aspects, the inventive charge-stabilized nanostructures and/or the charge-stabilized oxygen-containing nanostructures are capable of interacting with cellular membranes or constituents thereof, or proteins, etc., to mediate biological activities. In particular aspects, the inventive charge-stabilized nanostructures and/or the charge-stabilized oxygen-containing nanostructures harboring a solvated electron and/or electric field (electric double layer) are capable of interacting with cellular membranes or constituents thereof, or proteins, etc., to mediate biological activities.

In particular aspects, the inventive charge-stabilized nanostructures and/or the charge-stabilized oxygen-containing nanostructures interact with cellular membranes or constituents thereof, or proteins, etc., as a charge and/or charge effect donor (delivery) and/or as a charge and/or charge effect recipient to mediate biological activities. In particular aspects, the inventive charge-stabilized nanostructures and/or the charge-stabilized oxygen-containing nanostructures harboring a solvated electron and/or electric field (electric double layer) interact with cellular membranes as a charge and/or charge effect donor and/or as a charge and/or charge effect recipient to mediate biological activities.

In particular aspects, the inventive charge-stabilized nanostructures and/or the charge-stabilized oxygen-containing nanostructures are consistent with, and account for the observed stability and biological properties of the inventive electrokinetic fluids, and further provide a novel electride (or inverted electride) that provides for stabilized solvated electrons and/or electric fields (e.g., electric double layers) in aqueous ionic solutions (e.g., water, saline solutions, berverages, etc.).

In particular aspects, the charge-stabilized oxygen-containing nanostructures substantially comprise, take the form of, or can give rise to, charge-stabilized oxygen-containing nanobubbles. In particular aspects, charge-stabilized oxygen-containing clusters provide for formation of relatively larger arrays of charge-stabilized oxygen-containing nanostructures, and/or charge-stabilized oxygen-containing nanobubbles or arrays thereof. In particular aspects, the charge-stabilized oxygen-containing nanostructures can provide for formation of hydrophobic nanobubbles upon contact with a hydrophobic surface.

In particular aspects, the charge-stabilized oxygen-containing nanostructures substantially comprise at least one oxygen molecule. In certain aspects, the charge-stabilized oxygen-containing nanostructures substantially comprise at least 1, at least 2, at least 3, at least 4, at least 5, at least 10 at least 15, at least 20, at least 50, at least 100, or greater oxygen molecules. In particular aspects, charge-stabilized oxygen-containing nanostructures comprise or give rise to surface nanobubbles (e.g., hydrophobic nanobubbles) of about 20 nm×1.5 nm, comprise about 12 oxygen molecules (e.g., based on the size of an oxygen molecule (approx 0.3 nm by 0.4 nm), assumption of an ideal gas and application of n=PV/RT, where P=1 atm, R=0.0820571.atm/mol.K; T=295K; V=pr$^2$h=4.7×10$^{-22}$ L, where r=10×10$^{-9}$ m, h=1.5×10$^{-9}$ m, and n=1.95×10$^{-22}$ moles).

In certain aspects, the percentage of oxygen molecules present in the fluid that are in charge-stabilized nanostructures, or arrays thereof, having a charge-stabilized configuration in the ionic aqueous fluid is a percentage amount selected from the group consisting of greater than: 0.1%, 1%; 2%; 5%; 10%; 15%; 20%; 25%; 30%; 35%; 40%; 45%; 50%; 55%; 60%; 65%; 70%; 75%; 80%; 85%; 90%; and greater than 95%. Preferably, this percentage is greater than about 5%, greater than about 10%, greater than about 15% f, or greater than about 20%. In additional aspects, the substantial, or biologically relevant size (average or mean diameter) of the charge-stabilized oxygen-containing nanostructures, or arrays thereof, having a charge-stabilized configuration in the ionic aqueous fluid is a size selected from the group consisting of less than: 100 nm; 90 nm; 80 nm; 70 nm; 60 nm; 50 nm;

40 nm; 30 nm; 20 nm; 10 nm; 5 nm; 4 nm; 3 nm; 2 nm; and 1 nm. Preferably, this size is less than about 50 nm, less than about 40 nm, less than about 30 nm, less than about 20 nm, or less than about 10 nm.

In certain aspects, the inventive electrokinetic fluids comprise solvated electrons and/or stabilized electric fields. In further aspects, the inventive electrokinetic fluids comprises charge-stabilized nanostructures and/or charge-stabilized oxygen-containing nanostructures, and/or arrays thereof, which comprise at least one of: solvated electron(s); and unique charge distributions (polar, symmetric, asymmetric charge distribution) or electric field. In certain aspects, the charge-stabilized nanostructures and/or charge-stabilized oxygen-containing nanostructures, and/or arrays thereof, have paramagnetic properties.

By contrast, relative to the inventive electrokinetic fluids, control pressure pot oxygenated fluids (non-electrokinetic fluids) and the like do not comprise such charge-stabilized biologically-active nanostructures and/or biologically-active charge-stabilized oxygen-containing nanostructures and/or arrays thereof, capable of modulation of at least one of cellular membrane potential and cellular membrane conductivity.

In additional aspects, the inventive electrokinetic fluids comprise charge-stabilized nanostructures as disclosed herein, comprising variations in at least one of the ionic components (e.g., variations in the cation(s) or counterion(s)) and the gas component(s). As described elsewhere herein, in particular aspects, the inventive electrokinetically-altered fluids comprise saline (e.g., one or more dissolved salt(s); e.g., alkali metal based salts (Li+, Na+, K+, Rb+, Cs+, etc.), alkaline earth based salts (e.g., Mg++, Ca++), etc., or transition metal-based positive ions (e.g., Cr, Fe, Co, Ni, Cu, Zn, etc.,), in each case along with any suitable anion components, including, but not limited to F−, Cl−, Br−, I−, PO4−, SO4−, and nitrogen-based anions. Particular aspects comprise mixed salt based electrokinetic fluids (e.g., Na+, K+, Ca++, Mg++, transition metal ion(s), etc.) in various combinations and concentrations, and optionally with mixtures of counterions. In particular aspects, the inventive electrokinetically-altered fluids comprise standard saline (e.g., approx. 0.9% NaCl, or about 0.15 M NaCl). In particular aspects, the inventive electrokinetically-altered fluids comprise saline at a concentration of at least 0.0002 M, at least 0.0003 M, at least 0.001 M, at least 0.005 M, at least 0.01 M, at least 0.015 M, at least 0.1 M, at least 0.15 M, or at least 0.2 M. In particular aspects, the conductivity of the inventive electrokinetically-altered fluids is at least 10 µS/cm, at least 40 µS/cm, at least 80 µS/cm, at least 100 µS/cm, at least 150 µS/cm, at least 200 µS/cm, at least 300 µS/cm, or at least 500 µS/cm, at least 1 mS/cm, at least 5, mS/cm, 10 mS/cm, at least 40 mS/cm, at least 80 mS/cm, at least 100 mS/cm, at least 150 mS/cm, at least 200 mS/cm, at least 300 mS/cm, or at least 500 mS/cm. In particular aspects, any salt may be used in preparing the inventive electrokinetically-altered fluids, provided that they allow for formation of biologically active salt-stabilized nanostructures (e.g., salt-stabilized oxygen-containing nanostructures) as disclosed herein.

According to particular aspects, the biological effects of the inventive fluid compositions comprising charge-stabilized gas-containing nanostructures can be modulated (e.g., increased, decreased, tuned, etc.) by altering the ionic components of the fluids, and/or by altering the gas component of the fluid.

According to particular aspects, the biological effects of the inventive fluid compositions comprising charge-stabilized gas-containing nanostructures can be modulated (e.g., increased, decreased, tuned, etc.) by altering the gas component of the fluid. In preferred aspects, oxygen is used in preparing the inventive electrokinetic fluids. In additional aspects mixtures of oxygen along with at least one other gas selected from Nitrogen, Oxygen, Argon, Carbon dioxide, Neon, Helium, krypton, hydrogen and Xenon. As described above, the ionic components (cation(s) and/or counterion(s)) may also be varied, including along with varying the gas constituent(s).

According to particular aspects, the inventive electrokinetically-altered fluid compositions can be formulated as orally consumable beverages/drinks (e.g., water, sports drinks, exercise drinks, energy drinks, hydration beverages, food beverages, etc.). According to particular aspects, such beverages may have one or more additives, such as those already widely recognized in the relevant arts.

For example, a food beverage or fluid related to the present invention is a food in which a liquid or a food comprising the inventive electrokinetically-altered fluid compositions. Since foods can be mixed with a liquid or a food additive under various categories, such as an agricultural food, a livestock food, a fishery food, a fermented food, a canned food, an instant food and the like, according to states and forms of respective food additives, and no specific limitation is imposed on a kind, and state and form of food related to the present invention. Still further examples of food beverages of the present invention may include nutritional supplements and the like such as health foods in states and forms including liquid, powder, a tablet, a capsule, in which the inventive liquid or food additive is incorporated.

Beverages related to the present invention are, for example, beverages in which an electrokinetically-altered fluid of the present invention is added as a feature. Electrokinetically-altered fluid can be added to, or formulated as various kinds of beverages according to a kind, state and form thereof, no specific limitation is imposed on a kind, state and form of beverage. Examples thereof that can be named include alcoholic beverages, soft beverages or refreshing beverages such as fruit juice, concentrated fruit juice, nectar, soda pop, cola beverage, teas, coffee, black tea, water, sports drinks, exercise drinks, energy drinks, hydration beverages, food beverages, and the like. Alternatively, preformed beverages can be electrokinetically processed to produce the described biologically-active beverages.

According to certain aspects, the electrokinetically-altered fluids are produced as a sports, energy and/or food drink. According to further aspects, the sports, energy and/or food drink made with electrokinetically-altered fluids can contain additional components. These additional components can be added for many desirable traits, including but not limited to, mouth feel, taste, and increased nutrients. For example, additional components can be juice, carbohydrates, (e.g., mono- di- and polysaccharides, including but not limited to sucrose, glucose, fructose, dextrose, mannose, galactose, maltose lactose, maltodextrins, glucose polymers, maltotriose, high fructose corn syrup, beet sugar, cane sugar, and sucanat ketohexoses such sugars being arabinose, ribose, fructose, sorbose, tagatose sorbitol and those described in European Patent Specification Publication No. 223,540 incorporated herein by reference) salts, (including but not limited to those made from sodium, potassium, chloride, phosphorus, magnesium, calcium, sodium chloride, potassium phosphate, potassium citrate, magnesium succinate, calcium pantothenate, sodium acetate, acidic sodium citrate, acidic sodium phosphate, sodium bicarbonate, sodium bromide, sodium citrate, sodium lactate, sodium phosphate, anhydrous sodium sulphate, sodium sulphate, sodium tartrate, sodium benzoate, sodium selenite, potassium chloride, potassium acetate, potassium bicarbonate, potassium bromide, potassium citrate, potassium-D-gluconate, monobasic potassium phosphate, potassium tartrate, potassium sorbate, potassium iodide, magnesium chloride, magnesium oxide, magnesium sulphate, magnesium carbonate, magnesium aspartate and magnesium silicate) (European Patent Application Publication No. 587, 972, incorporated herein by reference, provides an extensive discussion of such salts and suitable concentrations thereof) vitamins, (e.g., vitamin C, the B vitamins, vitamin E, pantothenic acid, thiamin, niacin, niacinamide, riboflavin, iron and biotin) minerals, (e.g., chromium, magnesium and zinc) amino acids, (e.g. alanine, glycine, tryptophan, cysteine, taurine, tyrosine, histidine and arginine) electrolytes, trace elements, flavoring aids, phosphoric acid, citric acid, malic acid, fumaric acid, adipic acid, gluconic acid, lactic acid, calcium or sodium caseinate, whey protein, whey protein concentrate, whey protein isolate, whey protein hydrolyzate, demineralized whey protein, milk protein, soy protein, soy protein isolate, soy protein concentrate, pea protein, rice protein, casein hydrolyzate, soy flour, rice protein, wheat protein, corn protein and yeast concentrate.

Other ingredients including, but not limited to, coloring, flavor, artificial sweeteners and preservatives may also be added. Suitable amounts and types of all ingredients described herein are known in, the art and are not described in detail herein. It is within the skill of one in the art to prepare a beverage formulation having suitable concentrations of all the components.

Other component constituents of the nutritional composition in dry and liquid form include flavor components and/or colorant components. The flavor component for the nutritional composition of the present invention is provided to impart a particular and characteristic taste and sometimes an aroma to the nutritional composition. The use of a flavor component in the nutritional composition also provides an enhanced aesthetic quality to the nutritional composition which will increase the user's appeal in using the product, including fruit flavoring. The flavor component is selected from the group consisting of water soluble natural or artificial extracts that include apple, banana, cherry, cinnamon, cranberry, grape, honeydew, honey, kiwi, lemon, lime, orange, peach, peppermint, pineapple, raspberry, tangerine, watermelon., wild cherry, and equivalents and combinations thereof.

The colorant component for the nutritional composition of the present invention is provided to impart a characteristic color in conjunction with a particular flavor to the nutritional composition. For example, a yellow color is used for a banana flavor, or a red color for a cherry flavor. The colorant component is selected from the group consisting of water soluble natural or artificial dyes that include FD&C dyes (food, drug and cosmetic use dyes) of blue, green, orange, red, yellow and violet; iron oxide dyes; ultramarine pigments of blue, pink, red and violet; and equivalents thereof. The dyes discussed above are well known, and are commercially available materials, with their chemical structure being described, e.g., in 21 C.F.R. Part 74 (as revised Apr. 1, 1988) and the CTFA Cosmetic Ingredient Handbook, (1988), published by the Cosmetics, Toiletry and Fragrancy Association, Inc.

Different compositions for beverages have been described in related references. U.S. Pat. No. 3,657,424 to Donald et al., issued Apr. 18, 1972, teaches a citrus juice fortified with sodium, calcium and chloride ions beyond what are naturally present in the juice. The ions are added to supplement the requirements of individuals having diminished amounts of these substances present in his or her body fluids. This patent is incorporated herein by reference in its entirety, including for its teaching regarding the addition of additional components.

U.S. Pat. No. 4,042,684 to Kahm, issued Aug. 16, 1977, discloses a beverage for supplementing the dietetic requirements of sugar and essential salts in a mammalian body depleted through physical activity. The beverage contains an aqueous solution of fructose, glucose, sodium chloride, potassium chloride, and free citric acid. The patent teaches to include glucose in the beverage in an amount at least twice that of fructose. This patent is incorporated herein by reference in its entirety, including for its teaching regarding the addition of additional components.

U.S. Pat. No. 4,309,417 to Staples, issued Jan. 5, 1982, describes a protein fortified isotonic beverage containing sodium ions, potassium ions, chloride ions, phosphate ions, and a sweetener. Most of the electrolytes needed in the beverage are provided by the whey protein concentrate added to the beverage. The osmolarity of the beverage ranges from about 140 to about 375 mOs/kg. This patent is incorporated herein by reference in its entirety, including for its teaching regarding the addition of additional components.

U.S. Pat. No. 4,312,856 to Korduner et al., issued Jan. 26, 1982, discloses a beverage product adapted for rapid replacement of liquid and carbohydrate in the human body during periods of heavy muscle work. The product is a hypotonic solution that is free of monosaccharide. It contains mineral salts, soluble oligosaccharides and/or polysaccharides. This patent is incorporated herein by reference in its entirety, including for its teaching regarding the addition of additional components.

U.S. Pat. No. 4,322,407 to Ko, issued Mar. 30, 1982, teaches a chemical composition for reconstituting with water to provide electrolyte drink. The drink consists of sodium, potassium, magnesium, chloride, sulfate, phosphate, citrate, sucrose, dextrose, ascorbic acid, and pyridoxine. This patent is incorporated herein by reference in its entirety, including for its teaching regarding the addition of additional components.

U.S. Pat. No. 4,448,770 to Epting, Jr., issued May 15, 1984, describes a dietetic beverage adapted for human consumption to maintain the balance of body fluids during periods of fluid depletion or potassium depletion. The beverage contains potassium ions, calcium ions, magnesium ions, and sucrose. The amount of sucrose present ranges from 5 to 10 ounces per gallon of the beverage. This patent is incorporated herein by reference in its entirety, including for its teaching regarding the addition of additional components.

U.S. Pat. No. 4,551,342 to Nakel et al., issued Nov. 5, 1985, describes a beverage suitable for carbonated soft drinks having a pH range from about 2.5 to about 6.5. The beverage contains a mixture of calcium, potassium, and magnesium cations, defined by a first regression formula. Also included are acids, such as citric, malic, succinic and phosphoric acids, defined by a second regression formula. This patent is incorporated herein by reference in its entirety, including for its teaching regarding the addition of additional components.

U.S. Pat. No. 4,592,909 to Winer et al., issued Jun. 3, 1986, teaches a water based drink formulated for consumption by an athlete. The drink contains water to which have been added salts of sodium, potassium, calcium, and magnesium. The drink does not contain any sugar so that the osmolality of the drink can be kept low. This patent is incorporated herein by reference in its entirety, including for its teaching regarding the addition of additional components.

U.S. Pat. No. 4,649,051 to Gyllang et al., issued Mar. 10, 1987, discloses a beverage product adapted for administration of water and carbohydrates to a human body. The drink is monosaccharide-free. This patent is incorporated herein by reference in its entirety, including for its teaching regarding the addition of additional components.

U.S. Pat. No. 4,737,375 to Nakel et al., issued Apr. 12, 1988, teaches beverages and beverage concentrates nutritionally supplemented with mixtures of citric, malic, phosphoric acids, and also significant levels of solubilized calcium. The beverages and concentrates are substantially free of sugar alcohol. This patent is incorporated herein by reference in its entirety, including for its teaching regarding the addition of additional components.

U.S. Pat. No. 4,738,856 to Clark, issued Apr. 19, 1988, teaches a beverage solution containing ions of calcium, magnesium and potassium. The beverage also contains a sweetener and a stabilizer. This patent is incorporated herein by reference in its entirety, including for its teaching regarding the addition of additional components.

U.S. Pat. No. 4,830,862 to Braun et al., issued May 16, 1989, describes beverages and beverage concentrates supplemented with significant levels of solubilized calcium and low levels of sulfate and chloride ions. They also contain acids selected from phosphoric acid, citric acid, malic acid, fumaric acid, adipic acid, gluconic acid, and lactic acid, as well as mixtures of these acids. This patent is incorporated herein by reference in its entirety, including for its teaching regarding the addition of additional components.

U.S. Pat. No. 4,871,550 to Millman, issued on Oct. 3, 1989, teaches a nutrient composition. The composition contains free amino acids, carbohydrates, vitamins, minerals and trace elements, electrolytes, and flavoring aids. This patent is incorporated herein by reference in its entirety, including for its teaching regarding the addition of additional components.

Canadian Patent No. 896486 to Babagan et al., issued on Mar. 28, 1972, teaches an essentially isotonic beverage containing dextrose and electrolytes in contrast to the customary beverages that utilize sucrose. This patent is incorporated herein by reference in its entirety, including for its teaching regarding the addition of additional components.

A wide variety of electrolyte and sport drinks are available in the market. These drinks allegedly replenish water, carbohydrates, essential electrolytes, and other ingredients lost from a human body through dehydration.

Gatorade® Thirst Quencher, marketed by Stokely-Van Camp, Inc., contains about 6% of sucrose and glucose. It also contains sodium, potassium, chloride, and phosphorus. The drink has an osmolality in the range of between 280-360 mOs/liter.

Exceed® Fluid Replacement & Energy Drink, marketed by Ross Laboratories, contains about 7% of glucose polymers and fructose. It also includes sodium, potassium, calcium, magnesium, and chloride. The drink has an osmolality of 250 mOs/liter.

Quickkick®, marketed by Cramer Products, Inc., contains about 4.7% of fructose and sucrose. The drink is also provided with sodium, potassium, calcium, chloride, and phosphorus. The drink has an osmolality of 305 mOs/liter.

Sqwincher® the Activity Drink, marketed by Universal Products, Inc., contains glucose, fructose, sodium, potassium calcium, magnesium, phosphorus, chloride, and Vitamin C. The drink has an osmolality of 470 mOs/liter.

10-K™, marketed by Beverage Products, Inc., contains sucrose, glucose, fructose, sodium, potassium, Vitamin C, chloride, and phosphorus. The drink has an osmolality of 350 mOs/liter.

USA Wet™, marketed by Texas Wet, Inc., contains sucrose, sodium, potassium, chloride, and phosphorus. The drink has an osmolality of 450 mOs/liter.

Additional patents that disclose adding components to drinks include U.S. Pat. No. 5,114,723 to Stray-Gundersen, issued on May 19, 1992; U.S. Pat. No. 5,891,888 to Strahl, issued on Apr. 6, 1999; U.S. Pat. No. 6,455,511 to Kamping a, issued on Sep. 24, 2002; U.S. Pat. No. 6,989,171 to Portman, issued on Jan. 24, 2006. All of which are incorporated herein by reference in their entirety, including for its teaching regarding the addition of additional components.

Sports drinks to enhance stamina have been disclosed.

Prinkkila in U.S. Pat. No. 4,853,237 discloses a fitness drink powder containing glucose polymer, various salts and fruit acid. The drink composition of Prinkkila is designed to be available to the body in an optimum manner. In addition, the drink product is designed to maintain a high sugar concentration in the blood during physical exertion.

In U.S. Pat. No. 5,032,411 Stray-Gunderson discloses a hypotonic beverage with essential electrolytes, minerals and carbohydrates. Because the beverage composition is hypotonic, the stomach empties very rapidly and the composition can produce a beneficial physiologic response.

Kahm in U.S. Pat. No. 4,042,684 discloses a dietetic beverage containing sugar and essential salts. The composition is said to enhance energy stores. In addition, the composition does not require preservatives. The mixture of glucose and fructose used in the composition produces rapid transport of glucose out of the digestive system while fructose is more slowly transported out of the system.

Strahl in U.S. Pat. No. 6,039,987 discloses a composition to prevent dehydration and prevent cramps which contains electrolytes, carbohydrates and quinine.

King in U.S. Pat. No. 5,780,094 discloses a sports beverage containing a saccharide in the amount of 1.25% weight to volume of glucose.

Simone in U.S. Pat. No. 5,397,786 discloses a rehydration drink that contains carbohydrate, various electrolytes and one ammonia neutralizer such as aspartate, arginine and glutamate.

A flavored and sweetened aqueous dietetic beverage used to rehydrate the body is disclosed by Boyle in U.S. Pat. No. 4,874,606. L-aspartyl-L-phenyl-alanine methyl ester is included in the beverage to increase the degree of gastric emptying.

EXAMPLES

Example 1

According to Particular Aspects, Producing Biologically Active Electrokinetic Fluids is Enhanced by Processing the Fluids as Described Herein at Low Temperatures and/or Elevated Gas Pressures According to particular aspects, the optimal temperature for the electrokinetic production of the biologically active electrokinetic aqueous fluids is at a temperature between about −2° C. and about 10° C., between about −2° C. and about 5° C., between about 0° C. and about 5° C., and preferably at about 4° C. or a temperature equivalent to the maximum aqueous density of the fluid being processed (as the maximum density may vary somewhat with the salt concentration of the aqueous fluid). In particular aspects, the optimal temperature for the electrokinetic production of the biologically active electrokinetic aqueous fluids is at about 0° C. to about 4° C., 0° C. to about 3° C., 0° C. to about 2° C., 0° C. to about 1° C., 2° C. to about 4° C., or 3° C. to about 4° C.

In additional aspects, the optimal temperature for the electrokinetic production of the biologically active electrokinetic aqueous fluids is at the temperature of highest density of the aqueous (e.g., water or saline) fluid (e.g., 4° C.). For pure water this occurs at about 4° C., and is 1.0000 g/cm$^3$ plus or minus 0.0001.

Without being bound by mechanism, the optimal temperature for producing biologically active electrokinetic fluids likely coincides with providing a water structure that unexpectedly (with respect to water structures present at other temperatures or temperature ranges) facilitates the formation of charge-stabilized oxygen-containing nanostructures according to the present specification.

As appreciated in the art, the maximum density of water occurs at about 4° C., with the density falling with decreasing or increasing temperature. According to particular aspects, this temperature density profile indicates that prior to freezing, there is a unique water structure that occurs at or near the maximum density, and/or between the freezing point temperature of the aqueous fluid and the temperature of maximum aqueous density of the fluid, wherein said unique water structure optimally facilitates the formation of charge-stabilized oxygen-containing nanostructures according to the present specification. In particular aspects, this may reflect a water structure providing hydrogen bonding that is similar to, or required in the hydrogen bonding in the aqueous hydration shells of the charge-stabilized oxygen-containing nanostructures according to the present specification.

In further aspects, optimal production of biologically active electrokinetic aqueous fluids comprises introduction of gas at elevated pressures, including at elevated pressures in combination with the optimal temperature parameters discussed above. The standard atmosphere (atm) is a unit of pressure defined as being equal to 101,325 Pa or 101.325 kPa (e.g., 0.101 Mpa, 760 mmHg (Torr), 29.92 in Hg, 14.696 PSI, 1013.25 millibars). In particular aspects, the gas (e.g., oxygen gas in introduced into the mixing chamber of the electrokinetic mixing device at a pressure of at least 0.5 psi, at least 15 psi, at least 30, at least 45, at least 60, at least 75, at least 90, and preferably a pressure is used that is between about 15 psi and 100 psi. In particular aspects the oxygen pressure is at least 35 psi. In particular aspects, there is a gradient of pressure across the rotating mixing chamber from one end to the other (e.g., from 25 psi to 15 psi, with a 10 psi drop across the device), where such gradient may comprise, for example, pressure gradients within the range of about 0.5 psi and 100 psi, or within a sub range thereof.

In particular aspects, feature-induced cavitations of a rotating mixing device having an array of features (US2008/02190088 (now U.S. Pat. No. 7,832,920), US2008/0281001 (now U.S. Pat. No. 7,919,534); US2010/0038244, WO2008/052143,) provide for elaboration, within the mixing chamber, of discontinuous cavitation-induced pressurization-depressurization events localized at or near the features during electrokinetic fluid processing. In particular aspects, elaboration of discontinuous cavitation-induced pressurization-depressurization events with the mixing chamber is combined with introduction of oxygen to the mixing chamber at increased pressure as described above.

In particular aspects, oxygen is introduced into the mixing chamber of the electrokinetic mixing device by introducing liquid oxygen into the mixing chamber of the electrokinetic mixing device.

Example 2

The Stability of the Biological Activity of the Disclosed Electrokinetic Aqueous Fluids was Shown to be Temperature Dependent RNS60 modulates the expression of IL8. RNS60 is produced when isotonic saline is processed through the disclosed electrokinetic mixing device under 1 atmosphere of oxygen back-pressure, resulting in an oxygen content of 60 ppm. In order to test if RNS60 has additional effects on the bronchial epithelial cells, we tested for the release of multiple inflammatory mediators. Inflammation of the airway tissues is considered highly relevant in respiratory disease progression. Respiratory tract proinflammatory cytokines, such as IL-8 are used to access the epithelial cell response to environmental stimulants. In this experiment, we tested the effects of RNS60 on IL-8 secretion in human airway epithelial cells, when challenged with diesel exhaust particle (DEP) and recombinant TNFa(rTNFα).

Methods. The HBEpC cells were pretreated with serum free media containing saline solutions (NS or RNS60) and incubated at 37° C. for 1 hour. Cells were then stimulated with rTNFa or DEP and incubated over night. HBEpC culture supernatants were harvested and IL-8 ELISA was performed.

Results. The experiments were repeated three times and representative data is shown here. FIG. 47a shows that RNS60 regulates DEP-induced IL8 secretion. HBEpC were pre-treated with 10-30% NS or RNS60 for 1 hour, then stimulated with 100 ug/ml of DEP and incubated overnight at 37° C., supernatants were harvested and IL-8 ELISA was performed. Averaged data from three replicates are shown here.

FIG. 47b shows that RNS60 regulates rTNFa induced IL8, and it retains its biological activity at room temperature for days. HBEpC were pre-treated with 30% NS or RNS60 and stimulated with 100 ng/ml of rTNFa as described above, supernatants were harvested and IL-8 ELISA was performed. Averaged data from three replicates are shown.

As shown in FIGS. 47a & b, RNS60 significantly suppresses DEP or rTNFa induced IL-8 secretion by primary human bronchial cells. Moreover, the biological activity (IL-8 efficacy) of RNS60 can be reversed, at least in part, by leaving the fluid at 18-22° C. (room temperature) for 8 to 10 days as demonstrated by FIG. 47b.

According to particular aspects, therefore, once produced, the stability of the biological activity of the disclosed electrokinetic aqueous fluids is also temperature dependent. According to particular aspects, the optimal temperature for the stability of the biological activity of the disclosed electrokinetic aqueous fluids is at a temperature between about −2° C. and about 10° C., between about −2° C. and about 5° C., between about 0° C. and about 5° C., and preferably at about 4° C. or a temperature equivalent to the maximum aqueous density of the fluid being processed (as the maximum density may vary somewhat with the salt concentration of the aqueous fluid). In particular aspects, the optimal temperature for the stability of the biological activity of the disclosed electrokinetic aqueous fluids is at about 0° C. to about 4° C., 0° C. to about 3° C., 0° C. to about 2° C., 0° C. to about 1° C., 2° C. to about 4° C., or 3° C. to about 4° C.

In additional aspects, the optimal temperature for the stability of the biological activity of the disclosed electrokinetic aqueous fluids is also at the temperature of highest density of the aqueous (e.g., water or saline) fluid (e.g., 4° C.). For pure water an most saline solutions this occurs at about 4° C., and is 1.0000 g/cm$^3$ plus or minus 0.0001.

In particular aspects the stability of the biological activity of the electrokinetically-altered fluid is also enhanced if it is stored in a closed container with no, or little "head" volume. Preferably, if there is a "head volume" in the storage container, it is minimal oxygen-comprising head volume.

Example 3

Beneficial Effects of Electrokinetically Processed Fluids on Human Exercise Performance and/or Recovery were Demonstrated Overview:

Athletic performance is determined by many parameters that include age, genetics, training, and biomechanics. In addition, optimized diet and hydration are important factors in achieving and sustaining maximal performance. Beverages currently available in the market place aim at boosting performance by additives that include electrolytes, proteins, carbohydrates, or caffeine. Particular aspects of the present invention provide an innovative approach to athletic performance enhancement by offering a product that protects muscle cells through charge-stabilized nanostructure (CSN) technology.

CSN-containing fluids were generated using Applicant's proprietary process that involves Taylor-Couette-Poiseuille flow in the presence of oxygen.

The effects of electrokinetically-processed water on human treadmill exercise performance was evaluated by Seattle Performance Medicine, Seattle, Wash.

According to particular aspects, therefore, daily consumption of RSB prior to strenuous exercise improves performance and enhance training adaptation.

Materials and Methods:

RSB was produced using a proprietary pump involving Taylor-Couette-Poiseuille flow in the presence of oxygen as described herein. The test fluid was an electrokinetically-altered purified water (BEV-A) processed as described herein (see also US2008/02190088 (now U.S. Pat. No. 7,832,920), US2008/0281001 (now U.S. Pat. No. 7,919,534); US2010/0038244, WO2008/052143). The dissolve oxygen concentration (D.O.) for the test fluid was 52.4 ppm. The control (negative control) was a corresponding, but non-electrokinetically-processed purified water.

A double blind, randomized crossover study, was performed wherein 25 fit, male subjects (age: 18 to 35 years) consumed either RSB (CSN-containing fluid; BEV-A) or purified water (PW) as control for 2 weeks followed by a 60-minute treadmill exercise at 75% maximal oxygen consumption ($VO_2$max). $VO_2$max was determined according to the Modified Astrand protocol and rating of perceived exertion (RPE) was recorded according to the Modified Borg Scale at 15 and 50 minutes. Plasma markers of skeletal muscle breakdown, myoglobin and creatine kinase (CPK), were measured by ELISA. In addition, plasma concentrations of selected cytokines were measured with a Luminex 52-plex cytokine assay.

Consent forms, dietary and exercise protocols and diary workbooks were provided to all subjects. Prior to consumption of the study test and control beverages, Groups A and B consumed the same non-electrokinetically-altered "washout" beverage. Group A subjects began to consume their respective washout beverage one day before Group B and consumption of washout beverage continued for approx one-month prior to the start of the comparative study.

Group A and B subjects consumed their respective alternate beverage for 2 weeks.

TABLE 3

| Day 1 | Day 2 | Day 3 | Day 4 | Day 5 |
|---|---|---|---|---|
| M | T | W | Th | F |
| $VO_2$max 1 | $VO_2$max 1 | | Exhaustive Test | Exhaustive Test |
| Group A | Group B | | Group A | Group B |
| 10-12 subjects | | | 10-12 subjects | |
| Schedule in pairs | | | Schedule in pairs | |
| 1.5 hr blocks | | | 2 hr blocks | |
| 9:00-10:30 | | | 7:00-9:00 | |
| 10:30-12:00 | | | 9:00-11:00 | |
| 12:00-1:30 | | | 11:00-1:00 | |
| 2:00-3:30 | | | 1:00-3:00 | |
| 3:30-5:00 | | | 3:00-5:00 | |
| 5:00-6:30 | | | 5:00-7:00 | |
| (optional) | | | (optional) | |

Subjects maintained hydration, carbohydrate intake and exercise levels during the study.

Test Article:

Both control and test articles were stored under refrigerated conditions. Each bottle was labeled at the time of manufacture with the label key confidentially maintained at the Sponsor's facility. Both test and control articles were distributed to the subjects and kept refrigerated prior to consumption.

Study Subjects:

The study subjects were males between the ages of 18 and 35, having varying levels of fitness. The subjects were determined to be in good health with no pre-existing conditions and on no medications. Diet and activity levels were standardized prior to the start of the test article consumption.

Blood Samples:

Blood samples were taken for lactic acid at 20, 40 and 60 minutes (just prior to the end of exercise) during exercise. Venous samples were drawn prior to each beverage cycle, just prior to exercise, at 30 and 60 minutes after the start of exercise, and then 24 hrs after the exercise was completed. These samples included a cbc, complete metabolic profile, magnesium, calcium, phosphorous, myoglobin, lactic acid, CPK, CRP and Luminex cytokine analysis. Luminex samples were analyzed for cytokines including IL-1b, TNF-a, IL-6, IL-8, INF-g, IL-4 and others as determined by the sponsor. 24-hr urine collection for total volume, creatinine clearance, osmolarity and urine electrolytes was collected prior to starting beverage, prior to exhaustive exercise and 24 hrs after exercise.

Statistical Analysis:

Statistical analysis was stratified based on $VO_2$ Max (as example: 25-40 ml/kg/min and 41-60 ml/kg/min) and also examined as a whole.

$VO_2$ max, or maximal oxygen uptake, is one factor that can determine an athlete's capacity to perform sustained exercise and is linked to aerobic endurance. $VO_2$ max refers to the maximum amount of oxygen that an individual can utilize during intense or maximal exercise. It is measured as "milliliters of oxygen used in one minute per kilogram of body weight."

RPE refers to the rating of perceived exertion, wherein a visual analog scale was used to assess perceived fatigue (i.e., maximal exertion), at the end of the VO2 max.

Lactate refers to blood Lactate levels. Lactate in the blood can be correlated with the accumulation level of lactic acid in muscle tissue.

Results:

In Table 4 and FIG. 48, "P" corresponds to control (non-electrokinetic beverage) group, and "R": corresponds to the electrokinetic beverage test group.

The results (see Table 4 below and FIG. 48) indicate that the beverage had an effect on all 3 parameters of exercise performance, and that the direction of the effect was favorable direction in all 3 areas (positive for $VO_2$ max, negative for RPE (rating of perceived exertion) negative for lactate). The RPE had the most substantial shift, and is the most relevant factor for exercise performance.

Documenting performance improvement is really the end point goal of all research in sports science. Measurements such as VO2, lactate, your lab tests results are mildly persuasive but performance data is what really moves athletes, coaches and sports scientists.

TABLE 4

|  | | Average Change | | Largest Change | Largest Change |
| --- | --- | --- | --- | --- | --- |
|  | Total | P | R | P | R |
| $VO_2$max 2-1 | −1.078 | −1.826 | −0.267 | −7.540 | −5.380 |
| RPE 2-1 | −0.260 | 0.250 | −0.813 | 1.500 | −2.000 |
| Lactate 2-1 | −0.808 | −0.423 | −1.225 | −2.380 | −4.850 |

|  | MEANS | STANDARD DEVIATIONS | T-VALUE |
| --- | --- | --- | --- |
| vo2max: | 8216 | 3.1191 | 1.3170 |
| RPE | −.5200 | 1.1248 | −2.3115 |
| lactate: | −.3679 | 1.9895 | −0.9246 |

T-test Conclusions:
vo2max: With 80% confidence, the expected value of (R-P) will be in [−0.0006, 1.6438]. With 95% confidence, the expected value of (R-P) will be in [−0.4660, 2.1092].
RPE: With 95% confidence, the expected value of (R-P) will be in [−0.9843, −0.0557]. Note that the expected value of R—P is negative with 95% confidence.
lactate: With 80% confidence, the expected value of (R-P) will be in [−0.8923, 0.1565]. With 95% confidence, the expected value of (R-P) will be in [−1.189, 0.4534].

According to particular aspects, therefore, the present invention has substantial utility for enhancing exercise performance and recovery.

In particular aspects, the present invention has substantial utility for maintaining, and in some aspects normalizing, a reduced oxygenated blood level in an animal subsequent to a blood oxygen-lowering effect activity, such as what typically occurs in an animal, such as a human, after an oxygen-consuming activity, such as exercise. Changes in these physiologically measurable parameters are typically attendant an increase in physical activity, stress or other fatigue-inducing event.

In particular aspects, changes in heart rate, oxygen saturation, blood lactate, oxygen consumption, and fatigue assessment by a patient in response to a defined exercise regimen were favorably improved after consuming a defined quantity of the electrokinetically-altered fluids relative to control non-electrokinetically-altered fluid.

In particular aspects, the present invention has substantial utility for inhibiting and/or delaying onset of fatigue in a human. In particular aspects, subjects consuming electrokinetically-altered oxygenated fluids have a lesser drop in oxygen saturation compared to subjects consuming electrokinetically-altered oxygenated fluids.

In particular aspects, the present compositions and methods have substantial utility for inhibiting and/or reducing the increase in levels of blood lactate attendant human exercise, for reducing muscle soreness, and for reducing lactic acid accumulation in muscle.

In particular aspects, the present compositions and methods have substantial utility for reducing and/or inhibiting the onset of fatigue in response to exercise in a human.

In particular aspects, the present compositions and methods have substantial utility for increasing and/or replenishing available oxygen in the blood stream by consuming the oxygen-enriched nanostructured fluid preparations.

Example 4

Consumption of the Disclosed Sports Beverage Altered Markers of Exercise Performance and Cardio-respiratory Fitness)

Overview:

Currently available beverages designed to boost performance contain additives that include electrolytes, proteins, carbohydrates, or caffeine. Disclosed herein is a novel approach providing a beverage that aims at protecting muscle cells through charge-stabilized nanostructures (CSN). CSN-containing solutions are generated through Applicants' proprietary process that involves Taylor-Couette-Poiseuille flow in the presence of oxygen. Applicants have previously demonstrated that RNS60, a saline therapeutic formulation, alters the cellular response to various stressors through effects on voltage-gated ion channels and potentially other voltage-sensing proteins. Voltage-gated ion channels tightly regulate skeletal muscle contraction and cardiac function, and maximum oxygen uptake ($VO_2$max), a widely used measure of cardio-respiratory fitness, is in part determined by cardiac output.

In this Example, Applicants investigated whether oral consumption of Applicants' Sports Beverage (RB), a water beverage processed in a similar manner to RNS60, would alter selected physiological responses during exercise. In a double blind, randomized, crossover study, RB consumption led to a 5% increase in $VO_2$max in highly fit subjects and a decrease in the rating of perceived exertion in lesser-trained subjects. In addition, RB lowered the plasma levels of myoglobin and creatine kinase, two markers of the response to strenuous exercise, and attenuated exercise-induced circulating levels of several cytokines. Test and control fluids were as described in Example 3.

According to particular aspects, therefore, ingesting RB (e.g., in days preceding strenuous exercise) improves performance and enhances training adaptation.

Athletic performance is determined by many parameters that include age, genetics, training, and biomechanics. In addition, optimized diet and hydration are important factors in achieving and sustaining maximal performance. Beverages currently available in the market place aim at boosting performance by additives that include electrolytes, proteins, carbohydrates, or caffeine. Applicants have developed an innovative approach to athletic performance enhancement by providing fluid compositions that protectsmuscle cells through charge-stabilized nanostructure (CSN) technology.

As primary study endpoints, Applicants measured maximum oxygen uptake ($VO_2$max) and rating of perceived exertion (RPE). $VO_2$max has been linked to aerobic exercise performance, and while it is clear that $VO_2$max alone is not a predictor of overall athletic performance, it is an important measure of cardio-respiratory fitness [2]. $VO_2$max is influenced to a large extent by cardiac output, and cardiac function is controlled by a tightly regulated interplay of voltage-gated ion channels [3]. RPE is a subjective rating of physical exertion that is widely used as a general measure of physiological stress and the capability to sustain physical exercise [4]. In addition, Applicants measured plasma levels of myoglobin and plasma creatine kinase (CK), two routinely used markers of skeletal muscle damage [5].

Strenuous exercise has been shown to induce a cytokine response[6]. Among the cytokines released from skeletal muscle, interleukin-6 (IL-6) has been reported to undergo the most rapid and profound upregulation [6,7,8]. IL-6 has been suggested to induce an anti-inflammatory response that may be involved in preventing excessive tissue damage [9], but it has also been linked to general fatigue and underperformance syndrome (a.k.a. overtraining syndrome), a syndrome that is characterized by symptoms ranging from lack of performance improvement to signs of clinical depression [10,11]. In two independent treadmill exercise studies, plasma levels of IL-6 have been linked to $VO_2$max and RPE: in the first study, IL-6 levels were inversely correlated with $VO_2$max [12], whereas in the second, the lowering of plasma IL-6 levels induced by consumption of a carbohydrate beverage was associated with a lower RPE [13].

The response of other cytokines to exercise is less well studied. Circulating levels of soluble CD40 ligand (sCD40L, CD154) have been reported to be lowered by ultra-endurance exercise in athletes [14] and moderate exercise in heart failure patients [15]. CD40 and its ligand are involved in inflammatory processes in atherosclerotic plaque and the development of arterial thrombi that cause myocardial infarction, and sCD40L was identified as a risk marker in patients with acute coronary syndrome [16]. Colony-stimulating factors including macrophage colony-stimulating factor (M-CSF) have been shown to be upregulated in response to exercise [17], but the implications are unknown at this time. Based on the increasing recognition of exercise effects related to inflammatory processes, Applicants screened for changes in circulating levels of a comprehensive panel of cytokines using a Luminex 52-plex cytokine assay.

Study Design

Study participants were a blend of performance-oriented individuals and the general health-conscious population. Diet and activity levels were standardized prior to the testing, and subjects were instructed to consume a consistent diet throughout the entire study. For the 24-hour period preceding exercise testing, subjects were instructed to consume the same menu consisting of ~60% carbohydrate, ~15% protein and ~25% fat. Subjects were allowed to drink and eat freely until their pre-exercise venous blood sampling was obtained; from that point on they consumed approximately 10 ounces plain water until beginning the exercise, and they did not consume anything during the 60-minute endurance sessions. Subjects were advised to refrain from long or hard workouts for 2 days prior to their $VO_2$max test and throughout the trial weeks. They were also instructed to refrain from altering their training unless required to by the study design.

The study was designed as a crossover study (FIG. 49). Study subjects were randomized to two groups. One group consumed 1.5 L of RB per day for 2 weeks, and after a washout period of 2 weeks consumed 1.5 L per day of placebo water (PW). The other group started with consumption of 1.5 L of PW for 2 weeks, and after the washout period continued with 1.5 L per day of RB.

FIG. 49 shows a study design overview. Study subjects were randomized to 2 groups. Group 1 consumed 1.5 L of RB per day for 2 weeks, and after a washout period of 2 weeks consumed 1.5 L per day of PW. Group 2 started with consumption of 1.5 L of PW for 2 weeks, and after the washout period continued with 1.5 L per day of RB. Within each of the two beverage consumption periods, $VO_2$max was determined on day 12 and an exercise testing was performed on day 15.

$VO_2$max measurements. On day 12 of beverage consumption, $VO_2$max was determined according to the Modified Astrand protocol (variable 5-8 mph and increasing by 2.5% incline per stage). Subjects who required greater than 8 mph velocity used the Costill and Fox protocol (8-9 mph and increasing by 2% incline per stage). All tests were completed on Precor Treadmills under standard laboratory conditions of temperature (62-67° F.), pressure (700-715 mmHg) and relative humidity (30-40%). Prior to each test, the equipment was calibrated. The exercise protocol required subjects to complete a 10-minute self-paced warm-up before beginning the first stage of the test, which targeted an RPE of 11. Following a 3-minute first stage, the incline was increased every 2 minutes to the point of maximal effort. On completion of the test, final power output and $VO_2$max were noted. 75% of the $VO_2$max power output was calculated as a target for the exercise testing, which followed 3 days later.

Exercise testing. Exercise testing was conducted on day 15 of beverage consumption. During each test, subjects ran continuously for 60 minutes at 75% $VO_2$max on a level treadmill. Participants performed both exercises on the same treadmill and at the same pace. Blood samples were collected from the antecubital veins at three time intervals: immediately pre-exercise, 30 minutes into the exercise, just prior to completion of the exercise at 60 minutes, and 24 hours after completion of the exercise. For the sampling during the exercise, subjects slowed to a walk 3.0-3.5 mph for less than 3 minutes (average: 2.5 minutes) before returning to their running pace. The blood samples were used to measure complete blood count, complete metabolic profile, magnesium, calcium, phosphorous, myoglobin, lactic acid, creatine kinase (CK), and C-reactive protein (CRP). In addition, the plasma concentrations of a panel of cytokines were measured with a Luminex 52-plex cytokine assay.

RPE was recorded according to the Modified Borg Scale at 15 and 50 minutes. Lactate measurements were obtained utilizing an Accusport Lactate Plus analyzer at the following times: pre-exercise, during exercise at 20, 30, and 40 minutes and at the conclusion of exercise at 60 minutes. Twenty four-hour urine collection for total volume, creatinine clearance, osmolarity, and urine electrolytes were collected prior to starting beverage, prior to exhaustive exercise and 24 hours after the exercise.

Figure 1:
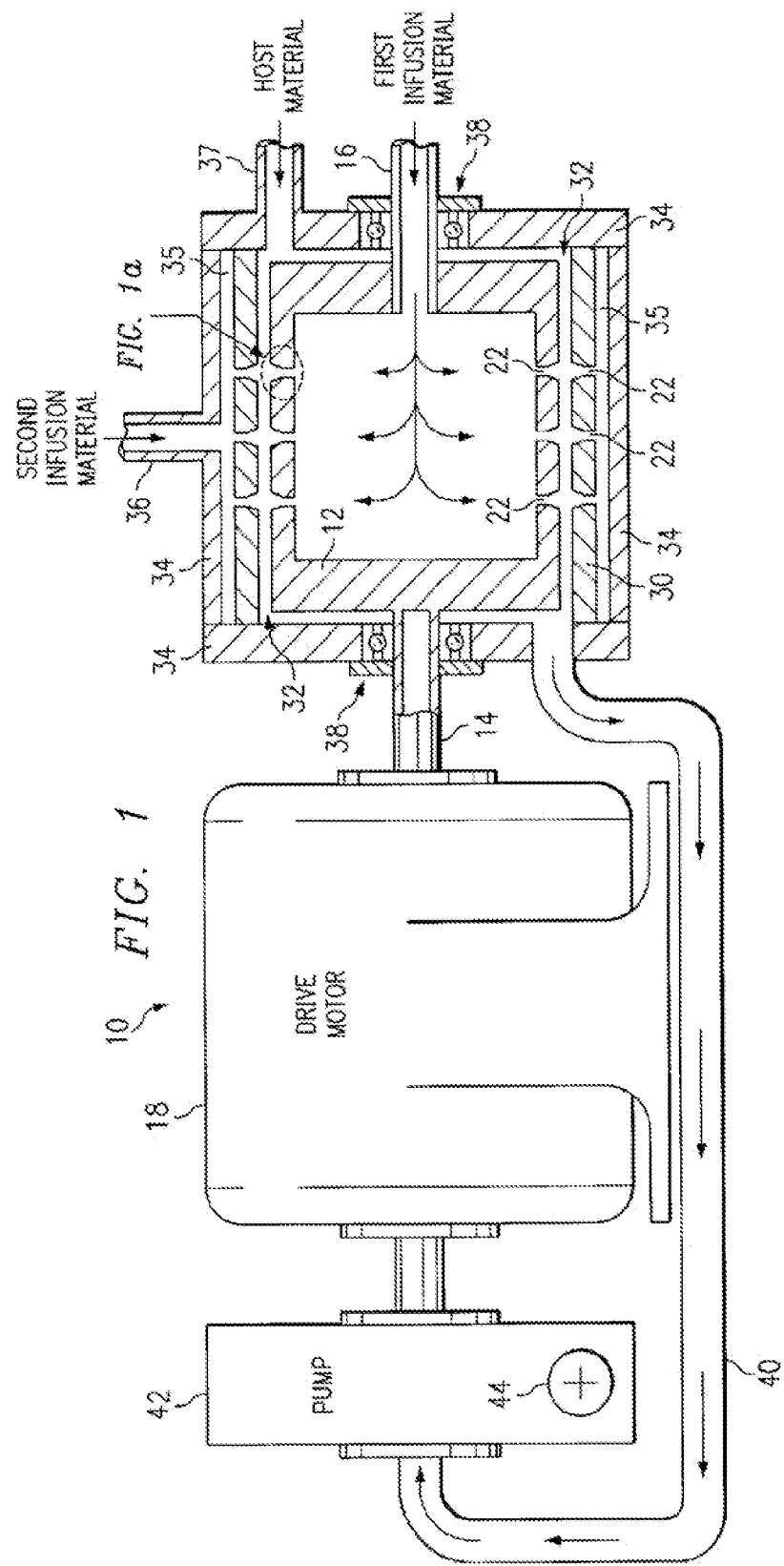
FIG. 1 is a partial cross-section, partial block diagram of a prior art mixing device.
Figure 2:
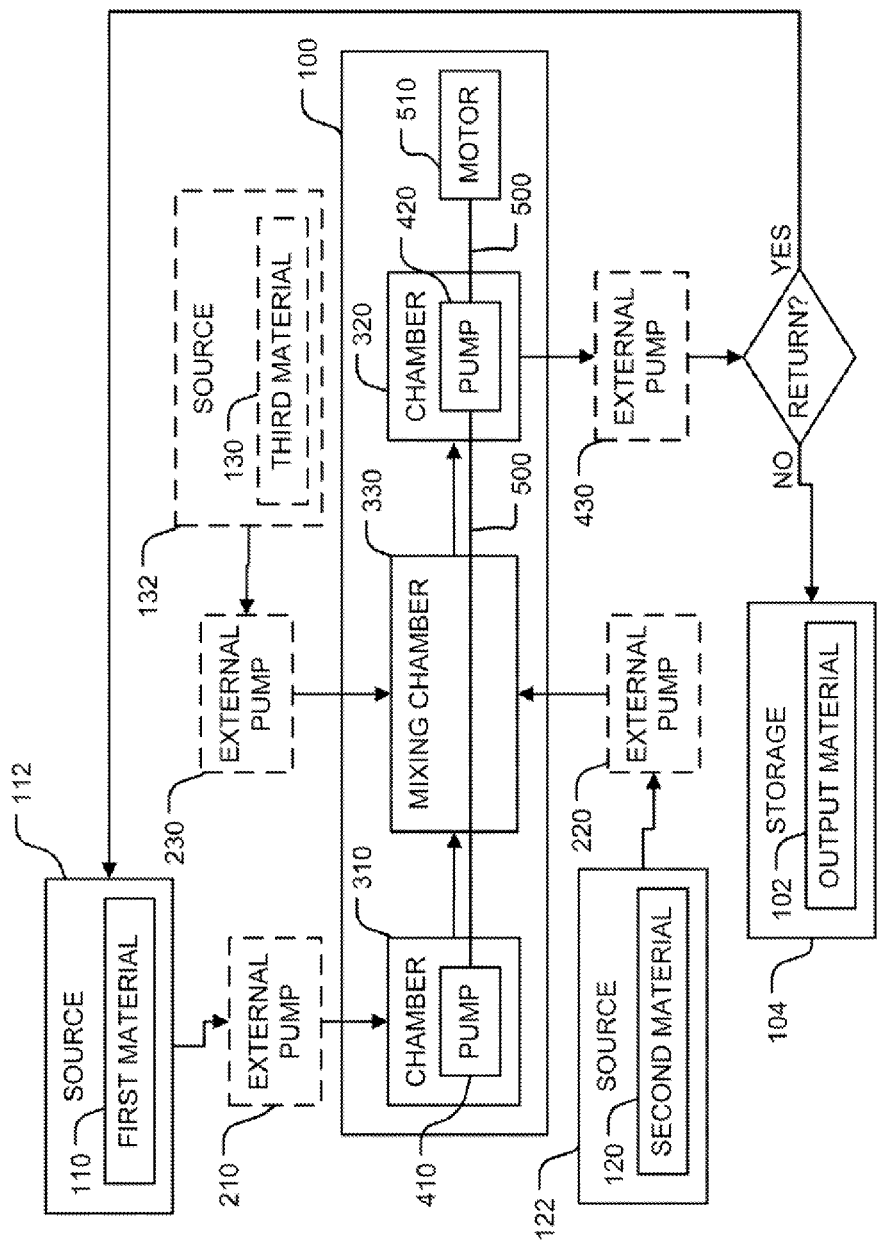
FIG. 2 is block diagram of an exemplary embodiment of a mixing device.
Figure 50A:
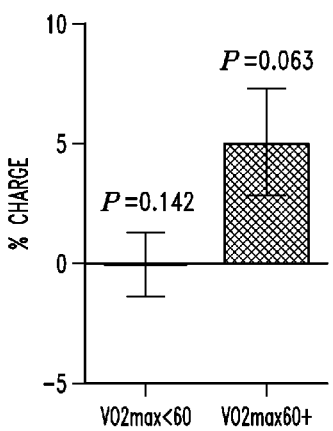

Results and Discussion:

RB consumption improved $VO_2$max in experienced athletes. Twenty-five fit male subjects (age: 18-35 years) were randomly assigned to the study groups. The study groups comprised individuals with a regular training history as well as more sedentary individuals, with a mean $VO_2$max of 53.4 mL/kg/min. A comparison of $VO_2$max values within the entire study population did not reveal a difference between subjects receiving Applicants' Sports Beverage (RB) and subjects receiving normal, purified water (PW). However, when study subjects were analyzed based on their beginning fitness level, a 5% improvement in the subgroup with a $VO_2$max above 60 mL/kg/min was observed (FIG. 50A). The difference did not reach statistical significance, likely due to the small number of subjects in this $VO_2$max range (n=6). It is noteworthy, though, that 5 out of the 6 subjects showed an increase in $VO_2$max (FIG. 2B). In study subjects with a $VO_2$max below 60 mL/kg/min, there was no difference in $VO_2$max between those who consumed RB and those who consumed PW (FIG. 2A).

Figure 50B:
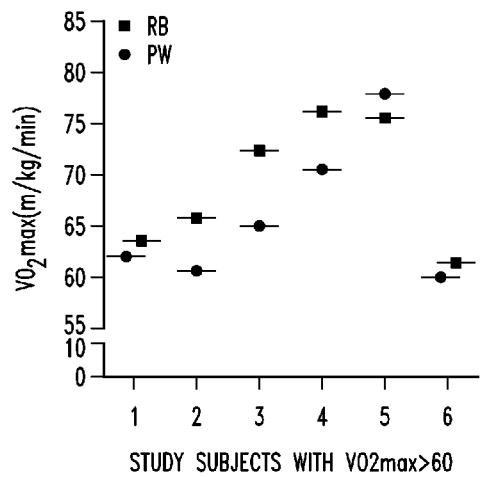

FIGS. 50 A and B show that RB consumption improves $VO_2$max in fitter athletes. FIG. 50A. Data are presented as percent change in RB groups separated by a $VO_2$max threshold of 60, compared to the corresponding PB groups (mean±SEM). FIG. 50B. Absolute VO$_2$max values for the six study subjects with a VO$_2$max>60 mL/kg/min.

VO$_2$max is defined by the Fick equation, VO$_2$max=Q (CaO$_2$–CvO$_2$), where Q is cardiac output, CaO$_2$ is the arterial oxygen content, and CvO$_2$ is the venous oxygen content. VO$_2$max, therefore, is to a large part dependent on cardiac output. In particular aspects, RB has the capacity to directly or indirectly alter cardiac ion channels. Other elements that influence VO$_2$max are related to oxygen delivery, uptake, and utilization [2]. Pulmonary contribution is not usually a limiting factor; however, in some elite athletes, exercise-induced hypoxemia (EIH) can result from very high stroke volume and rapid pulmonary circulatory transit time, where hemoglobin does not pick up adequate oxygen due to insufficient time spent at the alveolar level [18,19]. Additionally, the oxygen-carrying capacity of the blood, which is determined by plasma volume, iron status, and hemoglobin levels, is an important component of oxygen delivery [20]. At the muscle level, capillary density and membrane diffusion contribute to oxygen delivery, and mitochondrial density as well as enzyme and substrate status determine oxygen utilization rate [20].

While VO$_2$max is a trainable exercise parameter, it has been shown to have a genetic component, and among adults, high and low responders have been reported [21]. A 4.1% VO$_2$max increase was reported for a group of elite athletes after an intensive 24-day "live high-train low" altitude training regimen [22], and in untrained subjects, training at 75% of aerobic power for 30 minutes, 3 times a week, over 6 months, was necessary to yield an average VO$_2$max increase of 15-20% [23]. The 5% increase observed in the fitter athletes of our study represents a substantial improvement considering the short period of beverage consumption and the absence of a rigorous training program.

While a high VO$_2$max is required for competitive exercise performance, it is not the only determinant of the actual exercise performance. As an additional exercise response parameter, the rating of perceived exertion (RPE) was measured.

Figure 3:
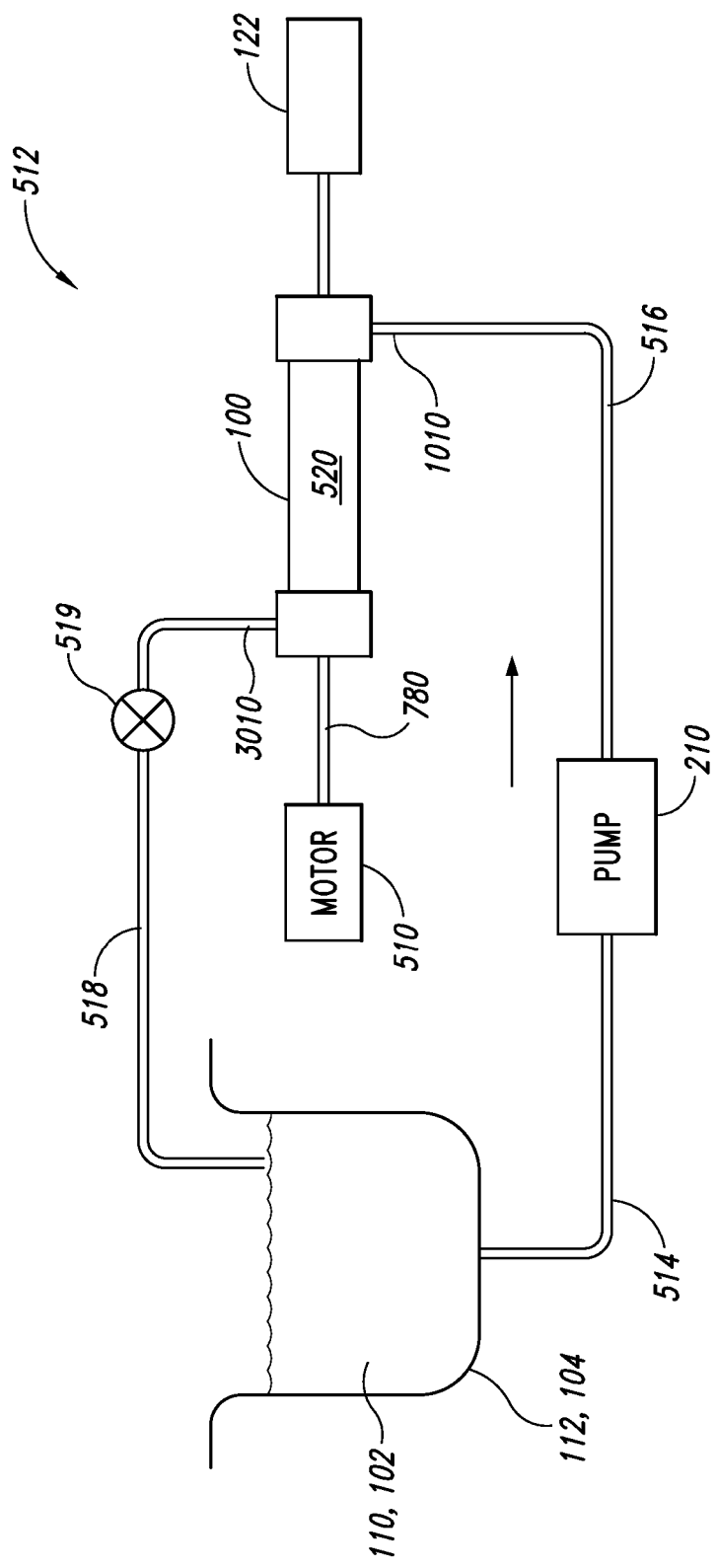
FIG. 3 is an illustration of an exemplary system for delivering a first material to the mixing device of FIG. 2.
Figure 4:
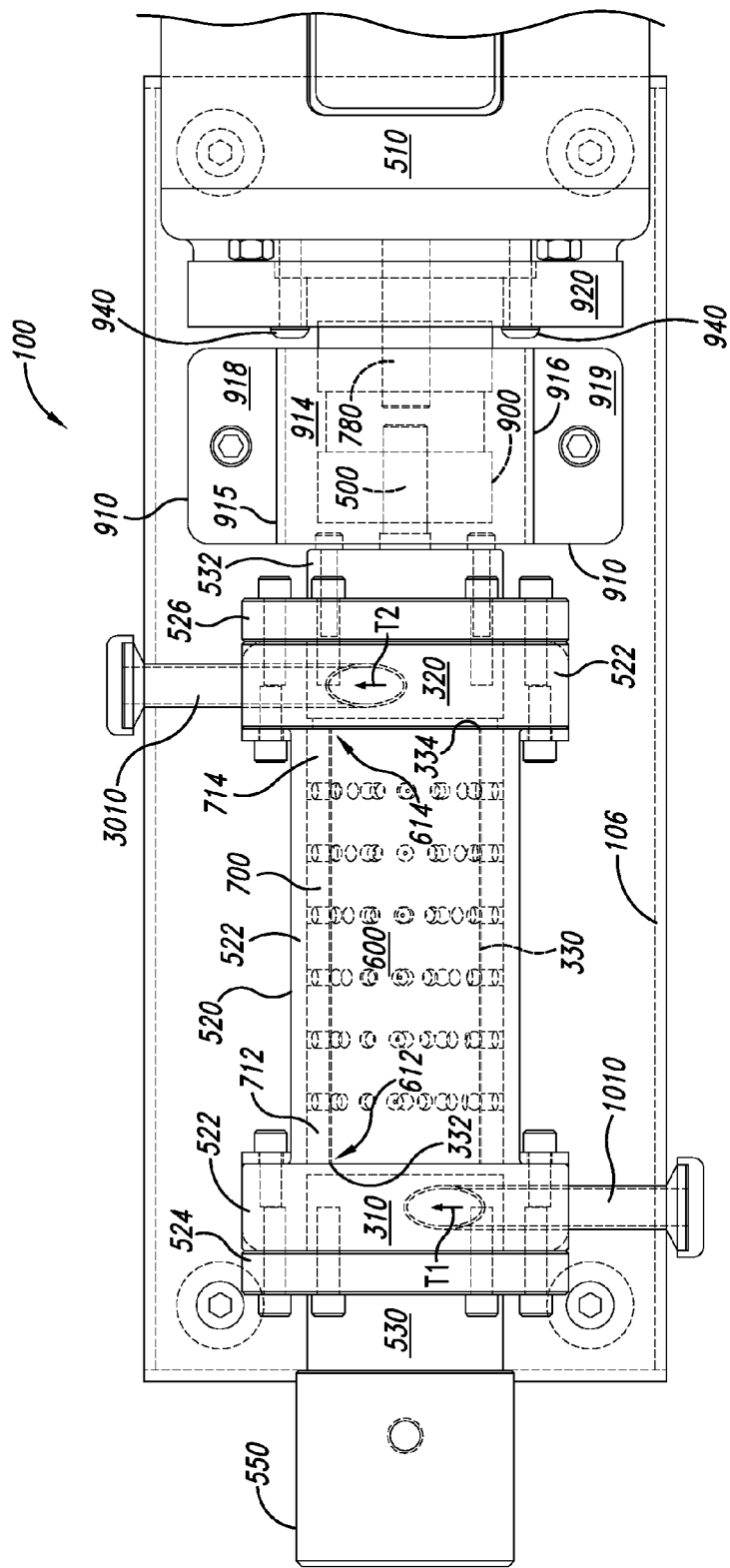
FIG. 4 is a fragmentary partial cross-sectional view of a top portion of the mixing device of FIG. 2.
Figure 5:
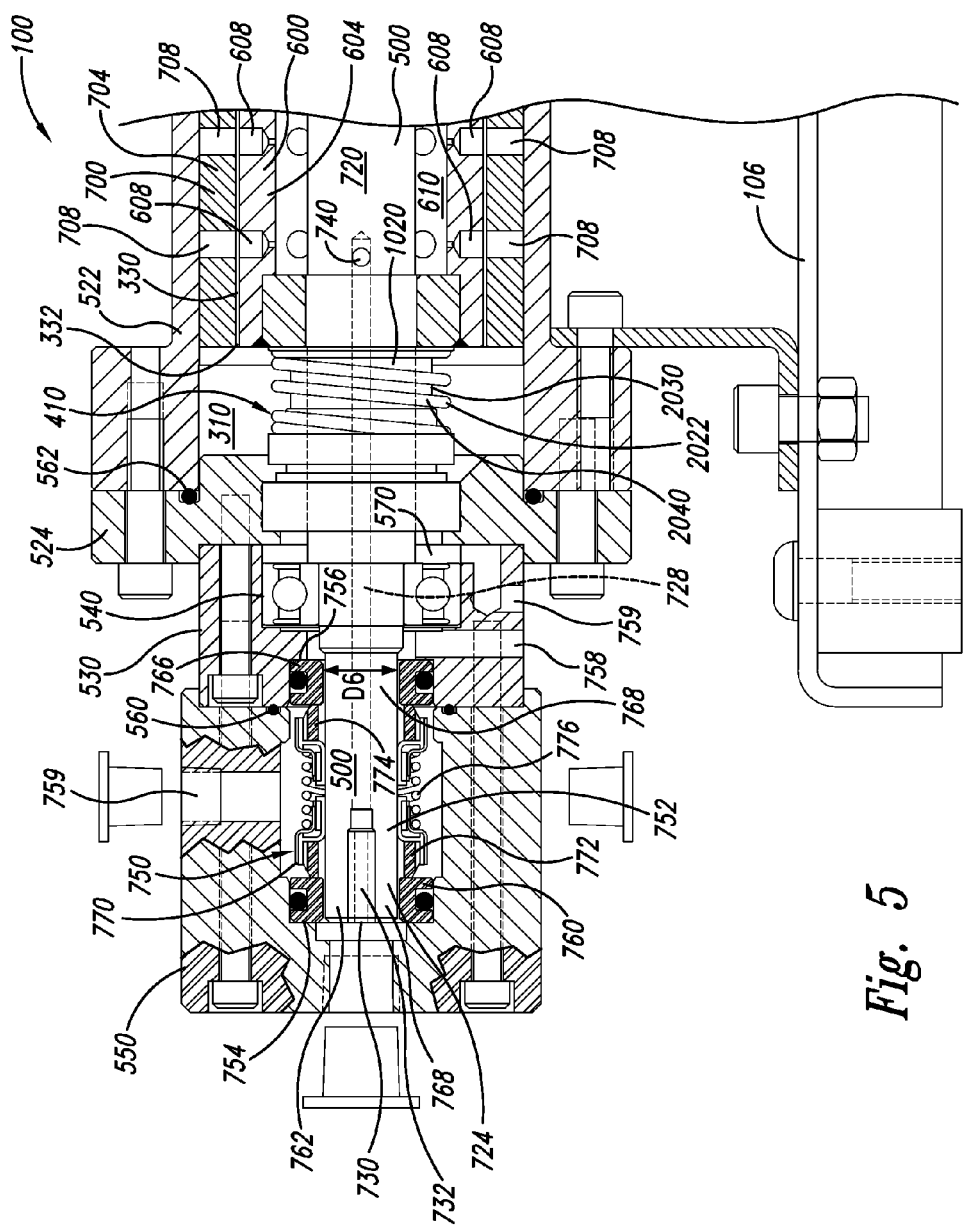
FIG. 5 is a fragmentary cross-sectional view of a first side portion of the mixing device of FIG. 2.

RB consumption altered RPE. RPE was measured at time points of 15 and 50 minutes during the treadmill exercise. As expected, RPE increased over time (FIG. 51). After consumption of RB, the study participants showed a lower RPE when compared to PW consumption (FIG. 3); this was particularly apparent in the subgroup of participants with a VO$_2$max <60 mL/kg/min (FIG. 3). The more highly trained subgroup likely operated on a lower RPE level compared to the lesser trained subgroup (12.5±1.5 vs. 14.8±0.3, p=0.02) and therefore may not have benefitted as much from the effect of RB.

FIG. 51 shows that RB consumption decreases RPE. RPE was recorded utilizing a Modified Borg Scale at 15 and 50 minutes during the performance exercise. The data are presented separated by a VO$_2$max-threshold of 60 mg/kg/min.

A lowered RPE means that an individual can complete a given exercise with a lower level of perceived exertion, or exercise longer until exhaustion is reached, and therefore indicates a potentially beneficial training response.

Crossover study artifacts. When analyzing the data from the second exercise trial, Applicants noticed that the subjects in the PW group of this trial (group 1 in FIG. 49) behaved more like they had in the first trial, when they consumed RB, than the PW group of the first trial (data not shown). This phenomenon was independent of the subjects' VO$_2$max. An adaptation to training as the underlying reason is not likely in such a short time frame. One possible explanation is that the washout period between the two trials was not sufficient to "reset" changes introduced by previous RB consumption. To avoid skewed data based on an insufficient washout, we excluded study group 1 (RB first) from further analysis and instead analyzed group 2 (PW first) only. All data shown below therefore represent the paired analysis of group 2 individuals consuming PW in trial 1 and RB in trial 2.

RB consumption lowered plasma myoglobin and CK levels. When the study subjects consumed PW, circulating myoglobin levels increased during exercise, peaking at a 2.8-fold elevation (absolute mean increase: 73 ng/mL) by the end of the exercise. When the subjects consumed RB, however, myoglobin levels did not rise above pre-exercise values (FIG. 52). CK levels increased more slowly when compared to myoglobin, which is in agreement with published reports [5]. The highest increase in plasma CK (1.9-fold, absolute mean increase: 202 units/L) was present 24 hours after the endurance trial when the subjects had consumed PW. RB consumption attenuated the elevation of plasma CK levels at the 60-minute and 24 h-hour time points in a statistically significant manner (FIG. 52).

FIG. 52 shows time point differences in levels of plasma myoglobin. Data are presented as differences (mean±SEM) between two time points as indicated by the labels of the x-axis. D0=day before start of beverage consumption, PE=time point immediately prior to starting the endurance exercise, 30 min=30-minute time point of endurance exercise, 60 min=60-minute time point of endurance exercise (end of exercise), 24 h=24 hours after completion of the exercise. P-values were calculated by Wilcoxon signed rank test.

FIG. 53 shows time point differences in plasma CK levels. Data are presented as differences (mean±SEM) between two time points as indicated by the labels of the x-axis. D0=day before start of beverage consumption, PE=time point immediately prior to starting the endurance exercise, 30 min=30-minute time point of endurance exercise, 60 min=60-minute time point of endurance exercise (end of exercise), 24 h=24 hours after completion of the exercise. P-values were calculated by Wilcoxon signed rank test.

According to particular aspects, therefore, the reduction of plasma myoglobin and CK levels indicates that muscle damage after exercise is attenuated by drinking RB.

Effects of RB consumption on plasma cytokine levels.

IL-6. Across all study groups, circulating levels of IL-6 were low, with a modest maximal increase of ~2-fold, from 3.97±7.79 (SD) pg/mL before the exercise to 8.30±8.14 (SD) pg/mL by the end of the exercise (p<0.0001). While others have reported post-exercise IL-6 levels to increase up to 100-fold [24], higher exercise levels and/or longer exercise durations are typically needed to achieve an increase of this magnitude. In several published studies, for example, running for a period of 2-3 hours was associated with maximal IL-6 levels in the range of 40 pg/mL to 120 pg/mL [7,13,25].

Applicants did not measure significant differences in plasma IL-6 levels between consumption of RB and consumption of PW (data not shown). Consumption of a 6% carbohydrate beverage was reported by others to decrease circulating IL-6 levels in marathon runners [13]; compared to Applicants' study, however, this effect was observed after a longer exercise duration (2.5 hours) and with IL-6 levels in a higher concentration range (50-75 pg/mL) [13]. Both, the increase of IL-6 after prolonged exercise and the lowering achieved by consumption of a carbohydrate-containing beverage, are in agreement with the fact that IL-6 production is induced in glycogen-depleted skeletal muscle [26,27].

IFN-α, ENA-78, and M-CSF. Two pro-inflammatory cytokines that displayed reduced plasma concentrations when study subjects consumed RB were interferon-α (IFN-α) and epithelial neutrophil activating protein 78 (ENA-78) (FIG. 54).

FIG. 54 shows that RB inhibited the exercise-induced increase of plasma levels of IFN-α (A) and ENA-78 (B). Data are presented as differences (mean±SEM) between two time points as indicated by the labels of the x-axis. D0=day before start of beverage consumption, PE=time point immediately prior to starting the endurance exercise, 30 min=30-minute time point of endurance exercise, 60 min=60-minute time point of endurance exercise (end of exercise), 24 h=24 hours after completion of the exercise. P-values were calculated by Wilcoxon signed rank test.

Figure 6:
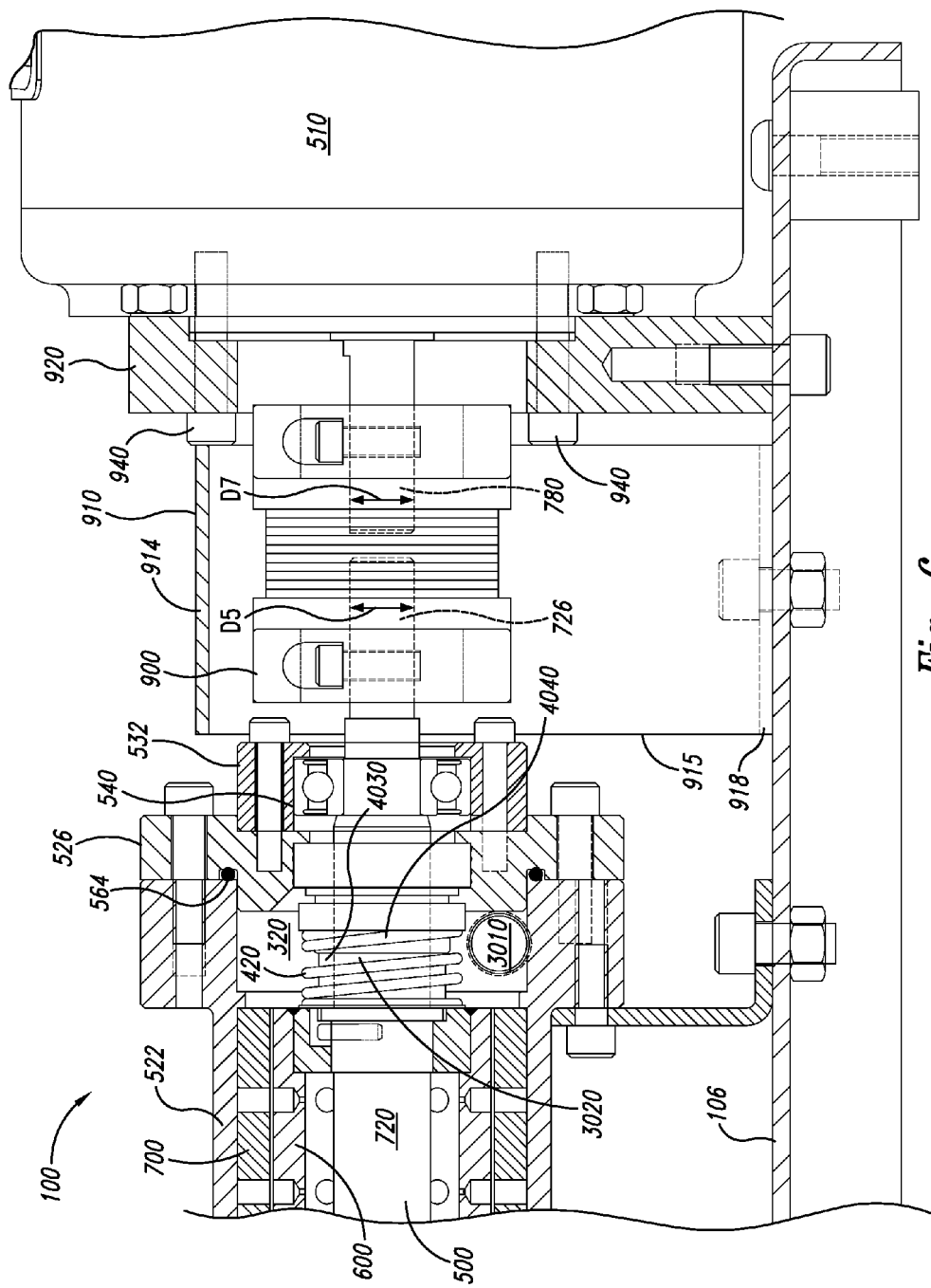
FIG. 6 is a fragmentary cross-sectional view of a second side portion of the mixing device of FIG. 2.
Figure 7:
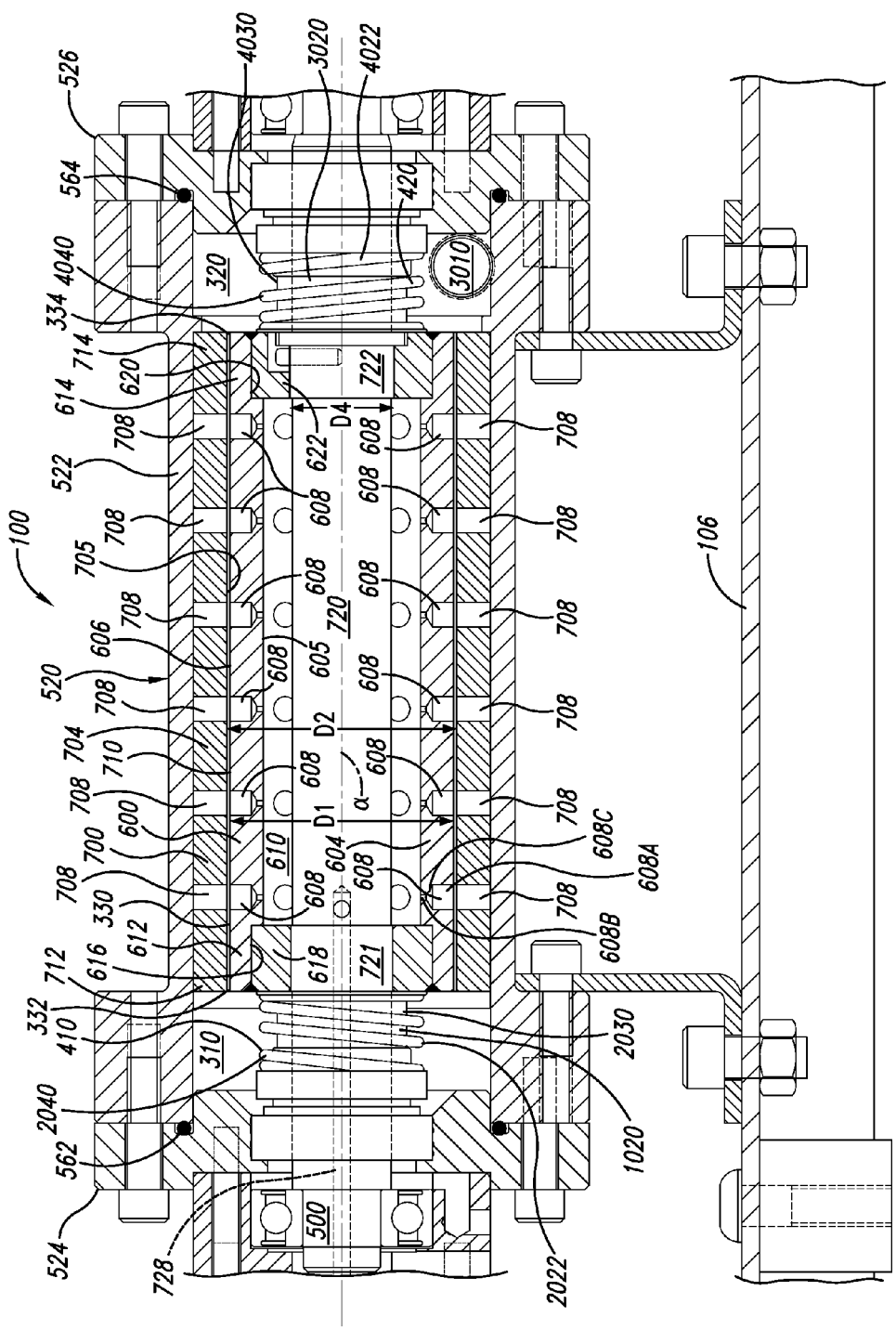
FIG. 7 is a fragmentary cross-sectional view of a side portion of the mixing device of FIG. 2 located between the first side portion of FIG. 5 and the second side portion of FIG. 6.
Figure 8:
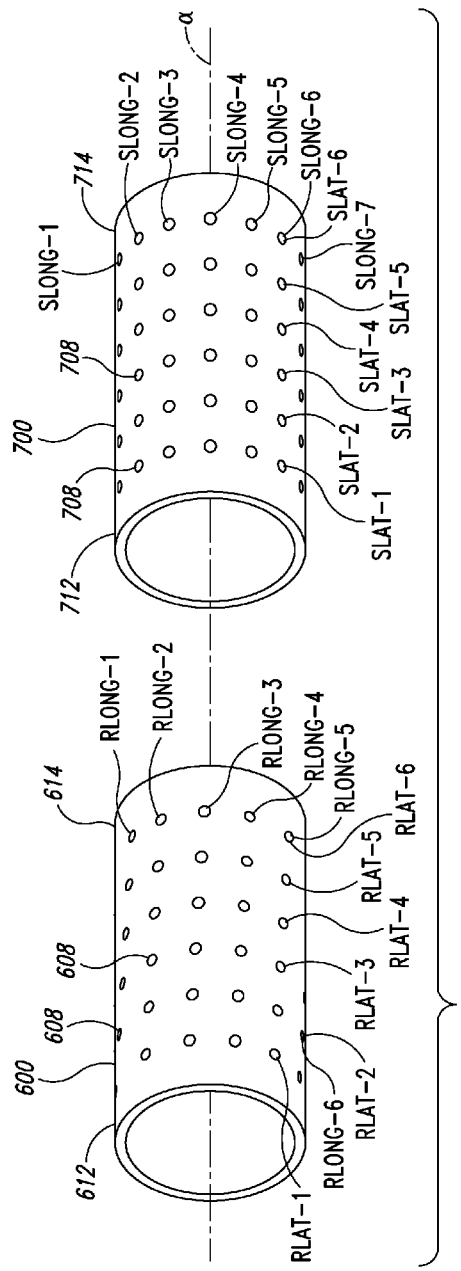
FIG. 8 is a perspective view of a rotor and a stator of the mixing device of FIG. 2.
Figure 9:
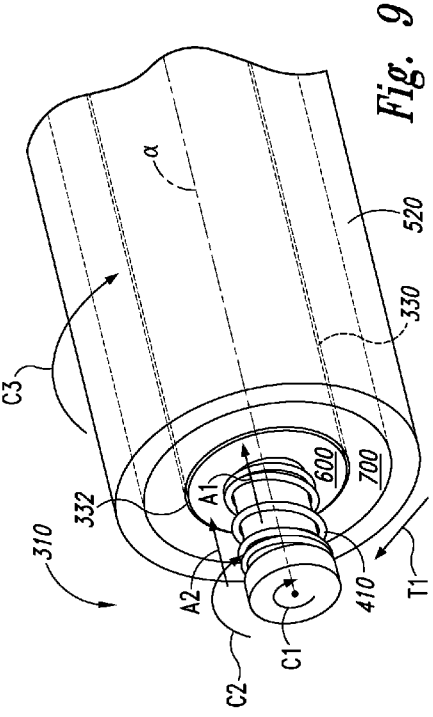
FIG. 9 is a perspective view of an inside of a first chamber of the mixing device of FIG. 2.
Figure 10:
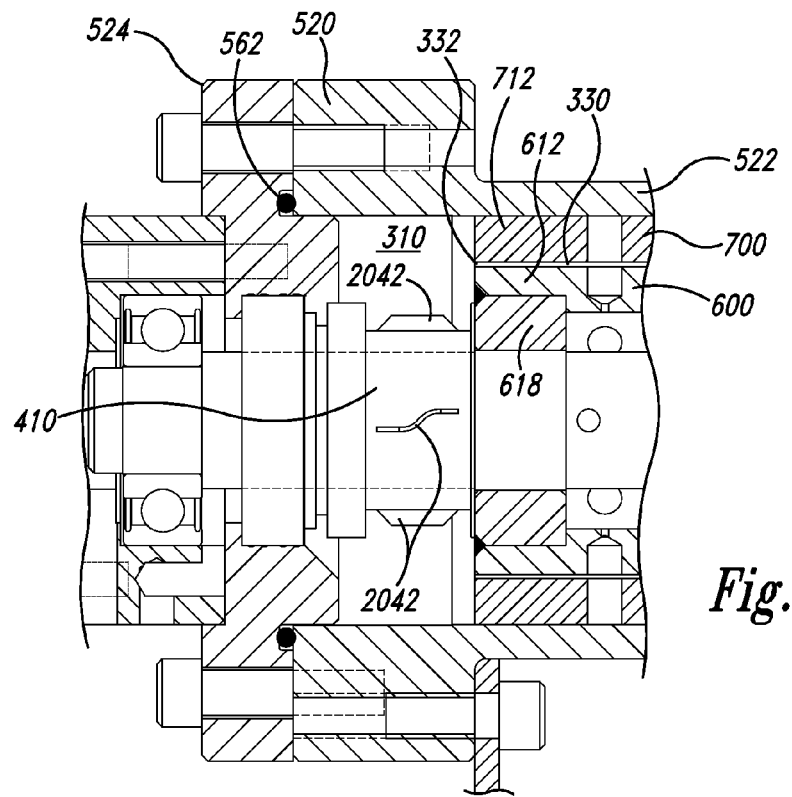
FIG. 10 is a fragmentary cross-sectional view of the inside of a first chamber of the mixing device of FIG. 2 including an alternate embodiment of the pump 410.
Figure 11:
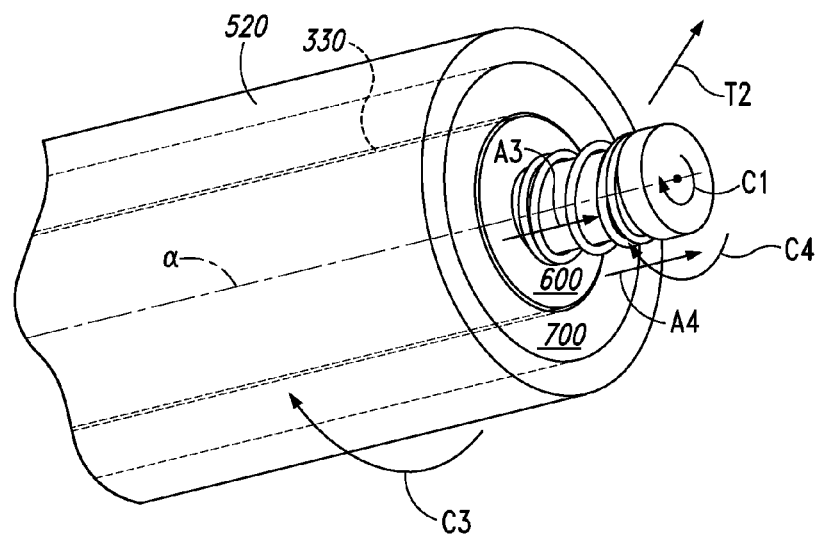
FIG. 11 is a perspective view of an inside of a second chamber of the mixing device of FIG. 2.
Figure 12:
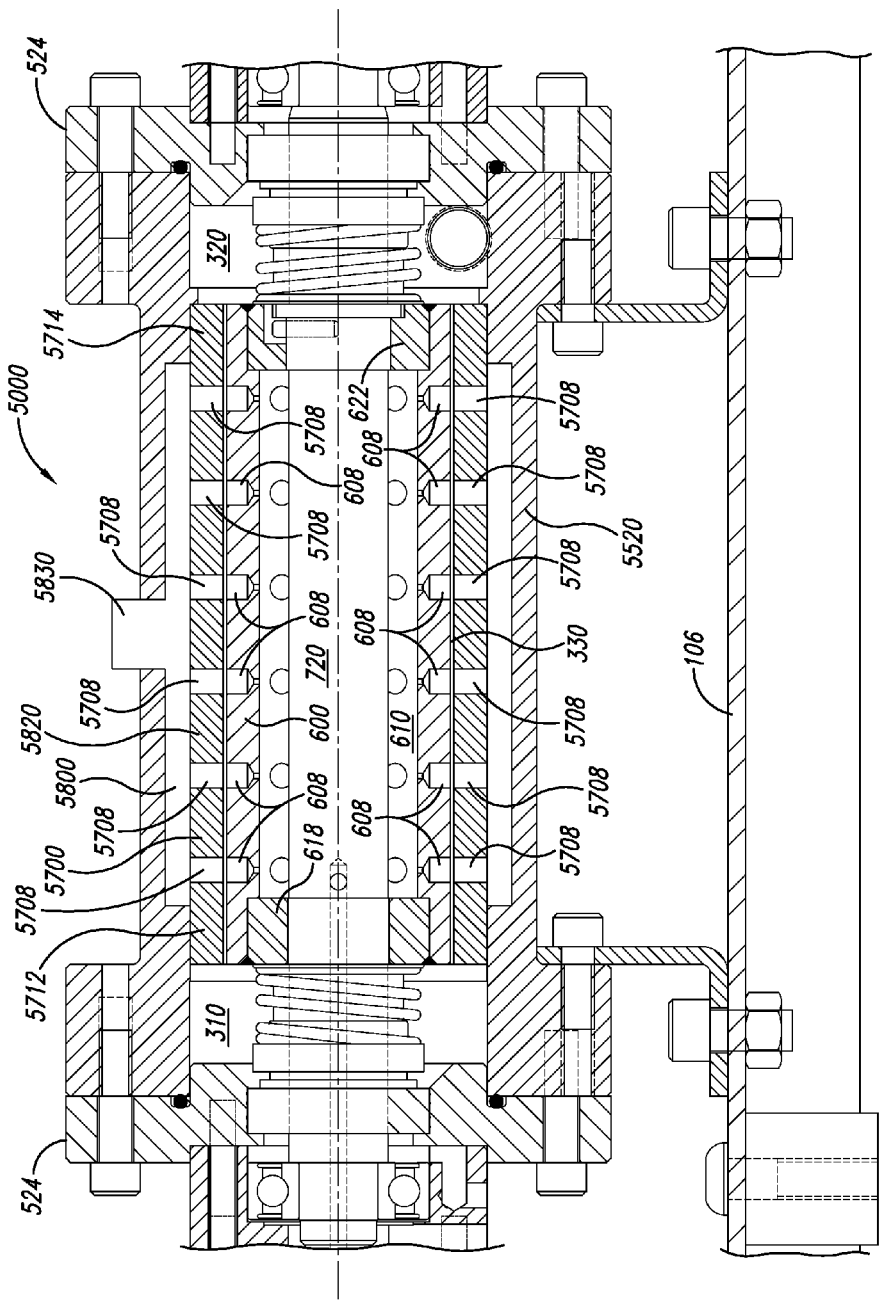
FIG. 12 is a fragmentary cross-sectional view of a side portion of an alternate embodiment of the mixing device.
Figure 13:
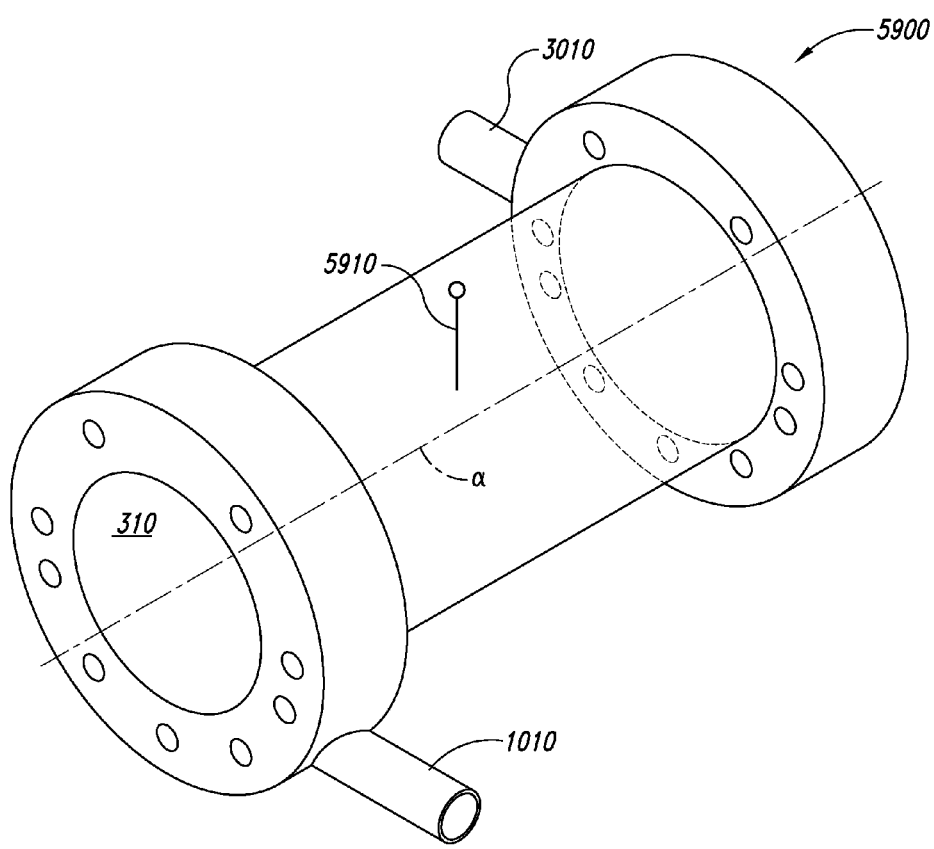
FIG. 13 is a perspective view of an alternate embodiment of a central section of the housing for use with an alternate embodiment of the mixing device.
Figure 14:
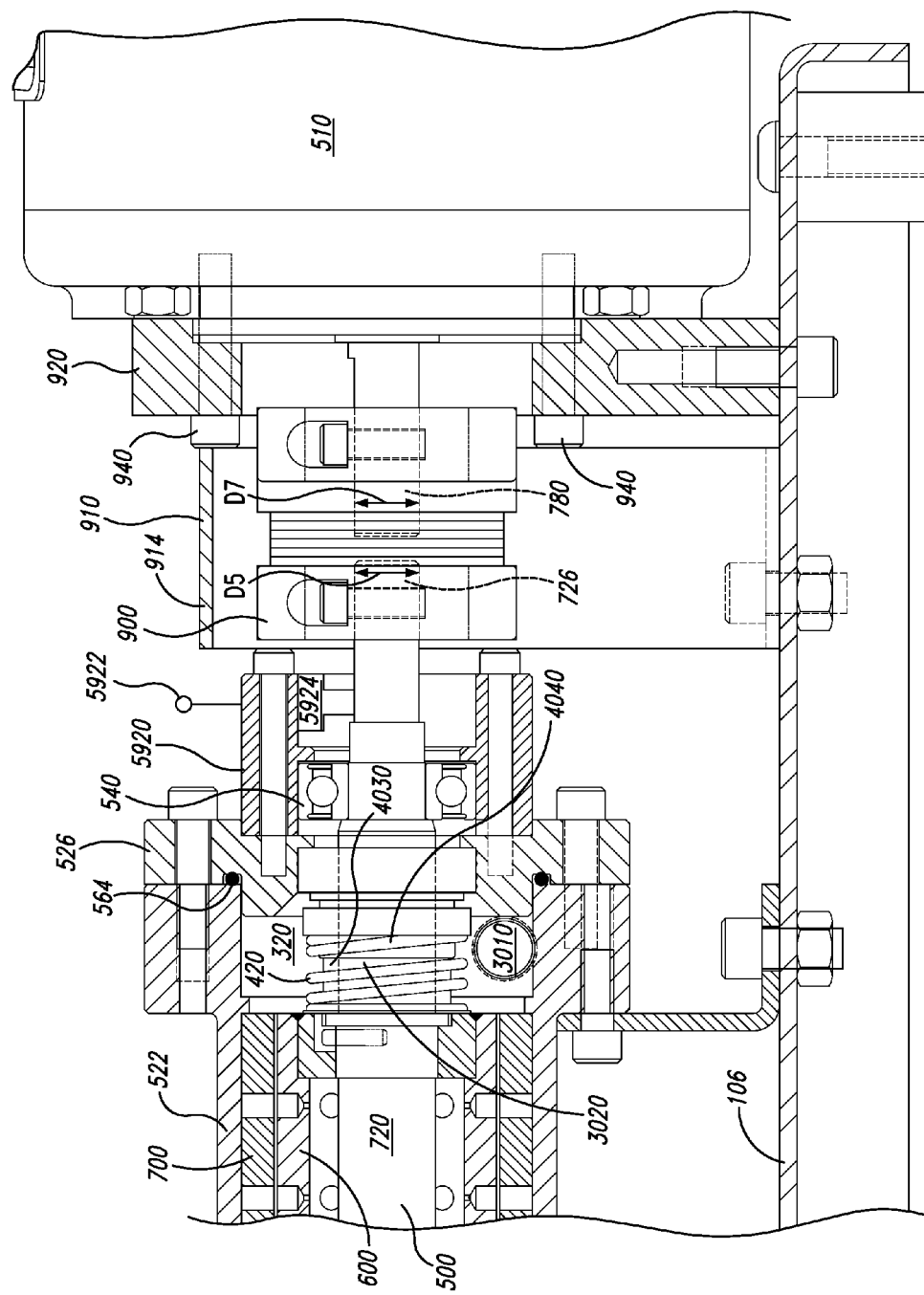
FIG. 14 is a fragmentary cross-sectional view of an alternate embodiment of a bearing housing for use with an alternate embodiment of the mixing device.
Figure 29:
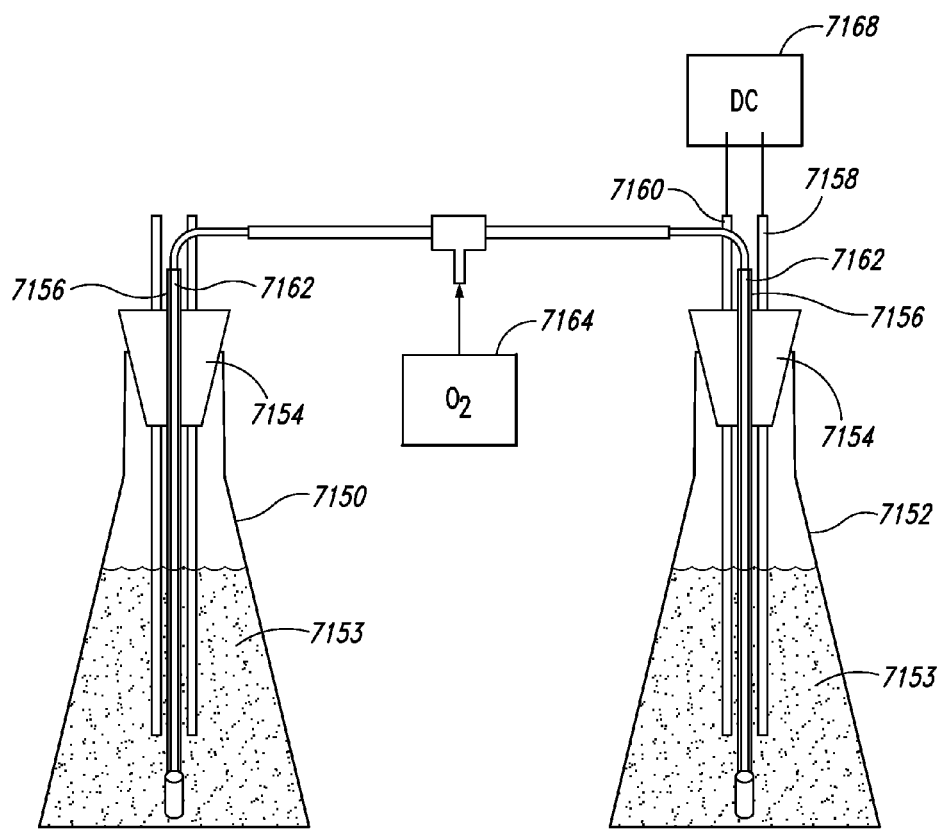
FIG. 29 is an illustration of an experimental setup.
Figure 30:
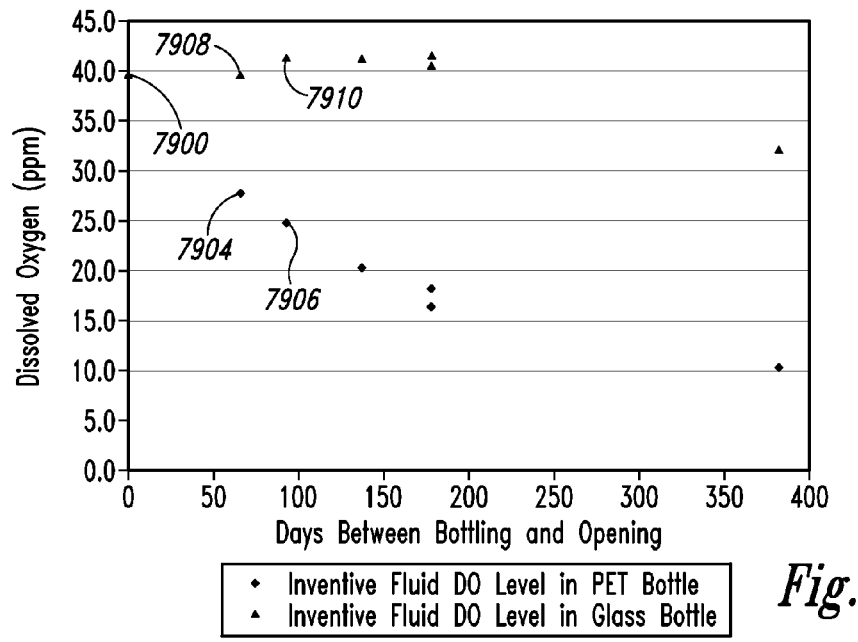
FIG. 30 illustrates dissolved oxygen levels in water processed with oxygen in the mixing device of FIG. 2 and stored a 500 ml thin walled plastic bottle and a 1,000 ml glass bottle each capped at 65° Fahrenheit.
Figure 31:
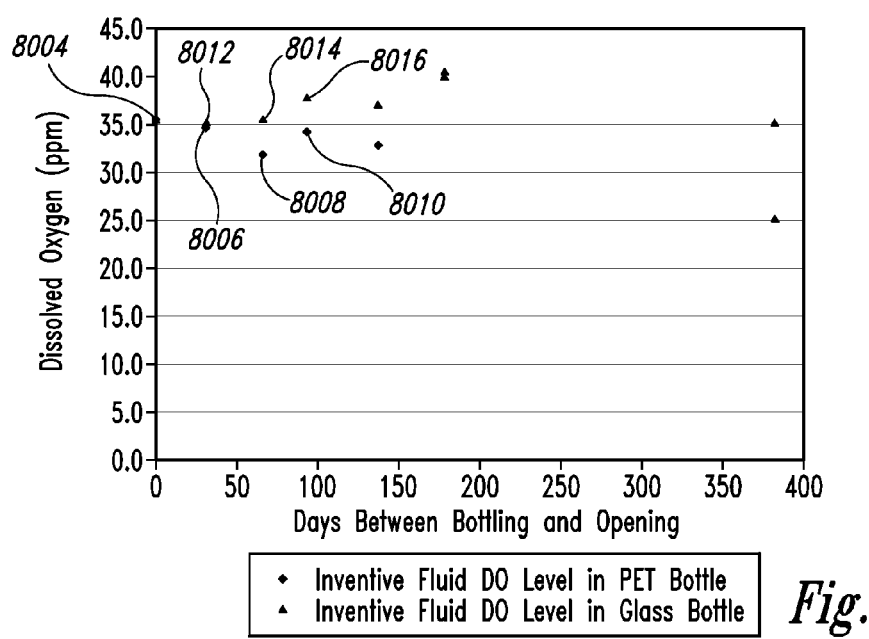
FIG. 31 illustrates dissolved oxygen levels in water processed with oxygen in the mixing device of FIG. 2 and stored in a 500 ml plastic thin walled bottle and a 1,000 ml glass bottle both refrigerated at 39° Fahrenheit.
Figure 32:
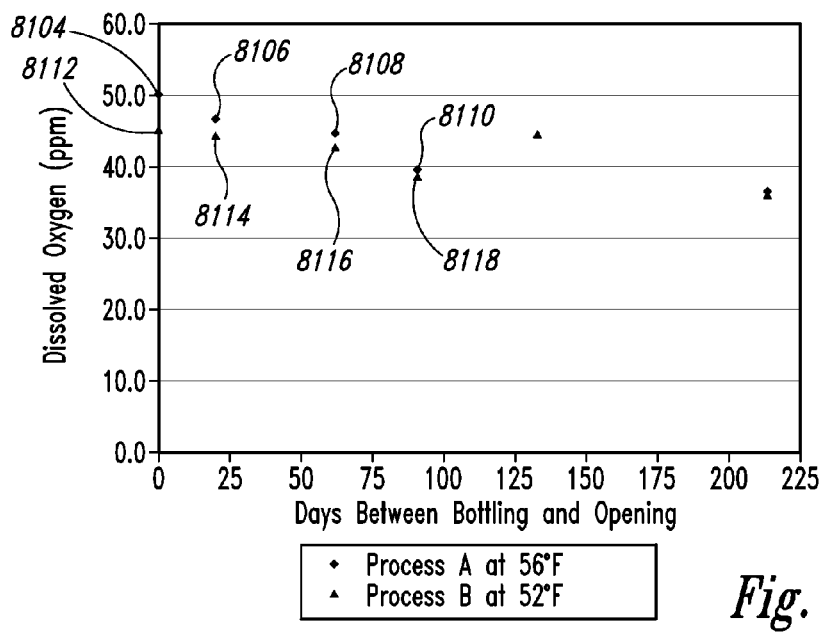
FIG. 32 illustrates the dissolved oxygen levels in GATORADE® processed with oxygen in the mixing device of FIG. 2 and stored in 32 oz. GATORADE® bottles having an average temperature of 55° Fahrenheit.
Figure 33:
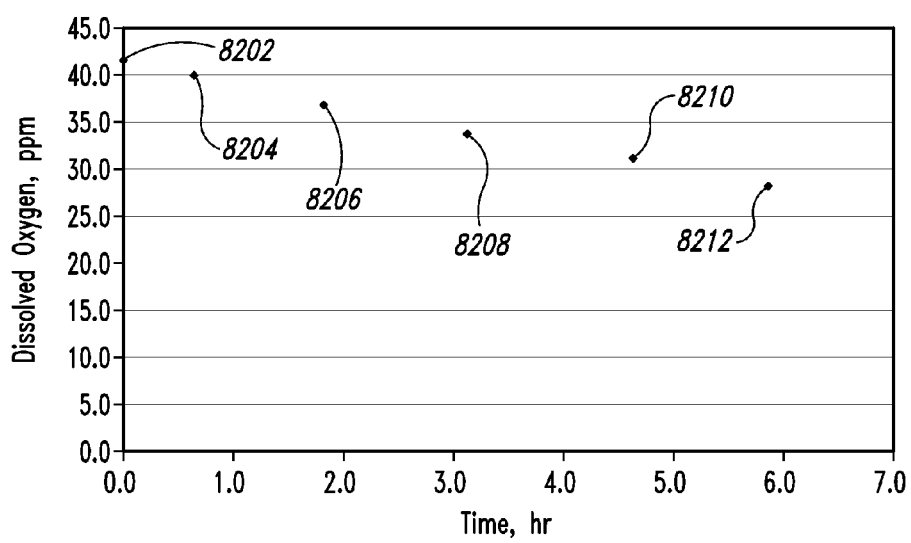
FIG. 33 illustrates the dissolved oxygen retention of a 500 ml braun balanced salt solution processed with oxygen in the mixing device of FIG. 2.
Figure 34:
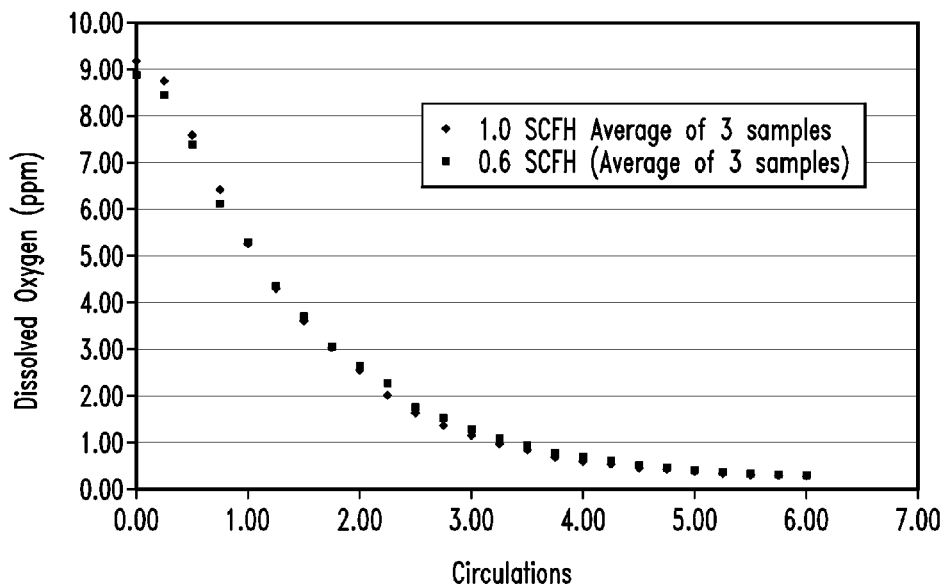
FIG. 34 illustrates a further experiment wherein the mixing device of FIG. 2 is used to sparge oxygen from water by processing the water with nitrogen in the mixing device of FIG. 2.
Figure 35:
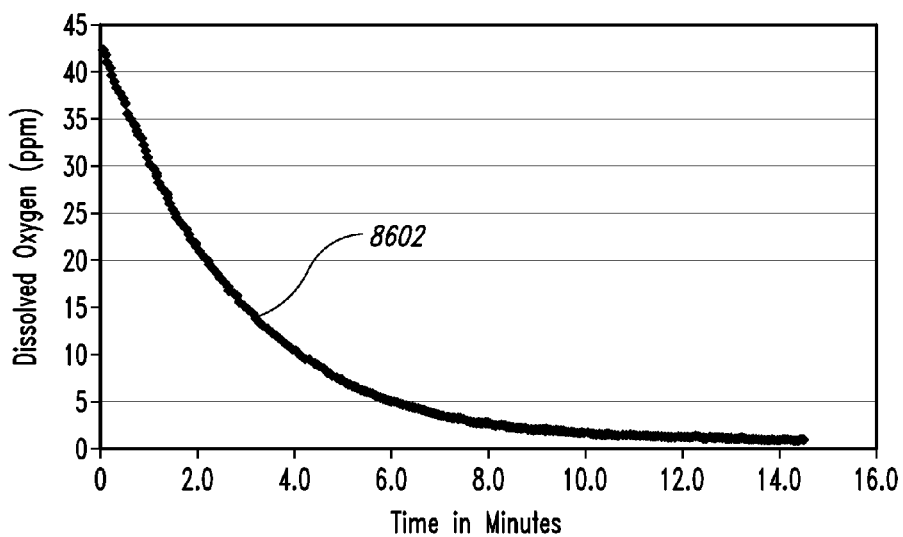
FIG. 35 illustrates the sparging of oxygen from water by the mixing device of FIG. 2 at standard temperature and pressure.
Figure 36:
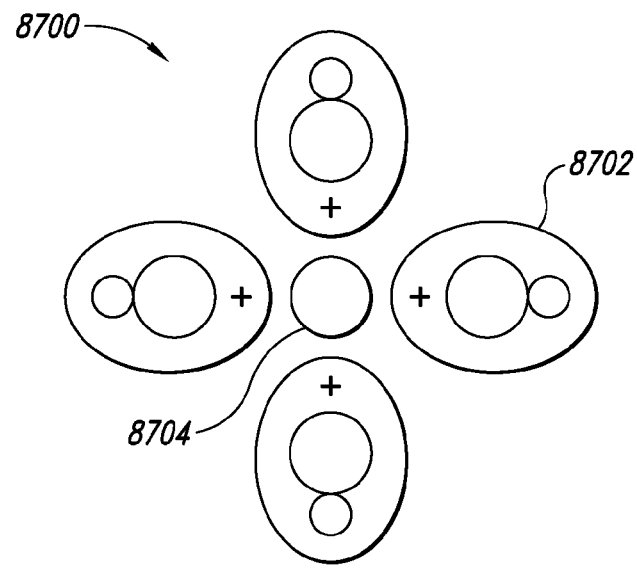
FIG. 36 is an illustration of a nanocage.
Figure 37:
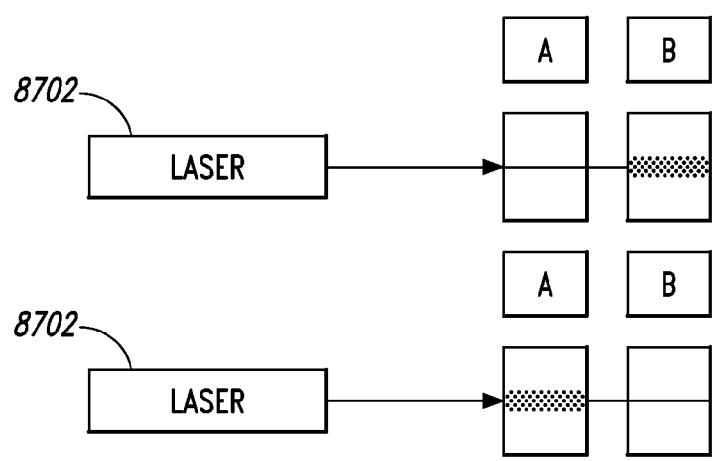
FIG. 37 illustrates the Rayleigh scattering effects produced by a sample of the water processed with oxygen by the mixing device of FIG. 2.
Figure 38:
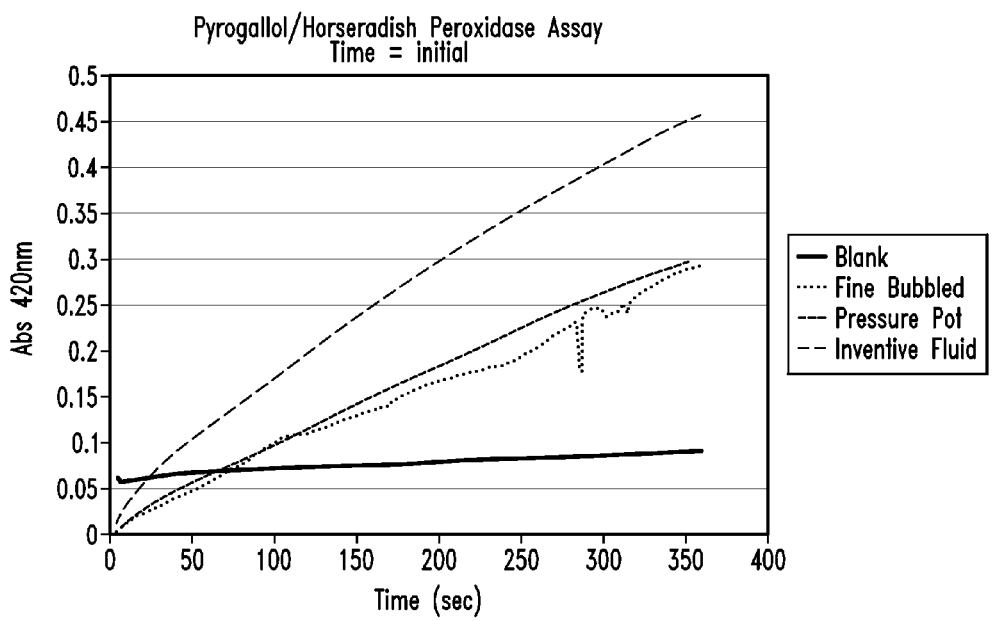
FIGS. 38-41 illustrate the inventive oxygen-enriched fluid tested positive for reactivity with horseradish peroxidase by pyrogallol, while the pressure pot and fine bubbled water samples had far less reactivity.
Figure 39:
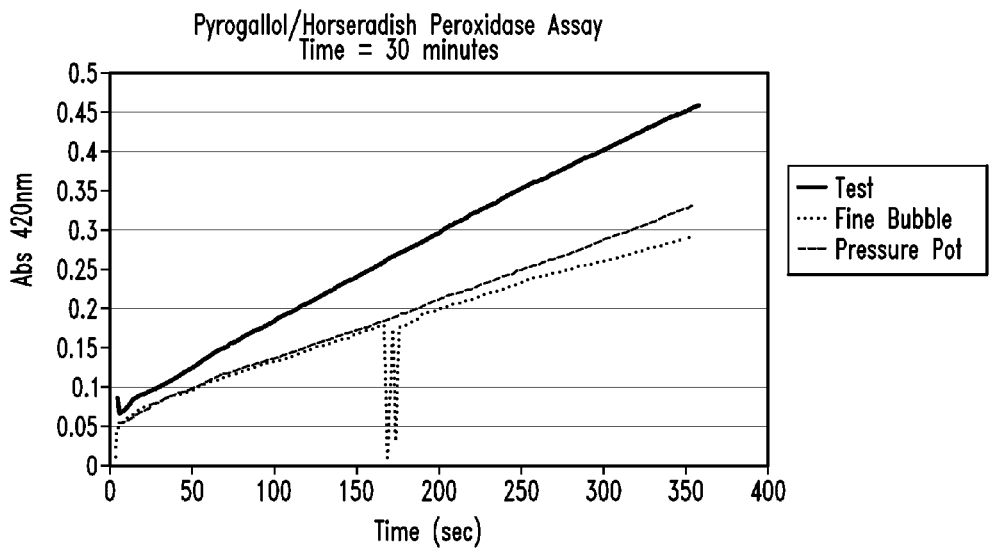
Figure 40:
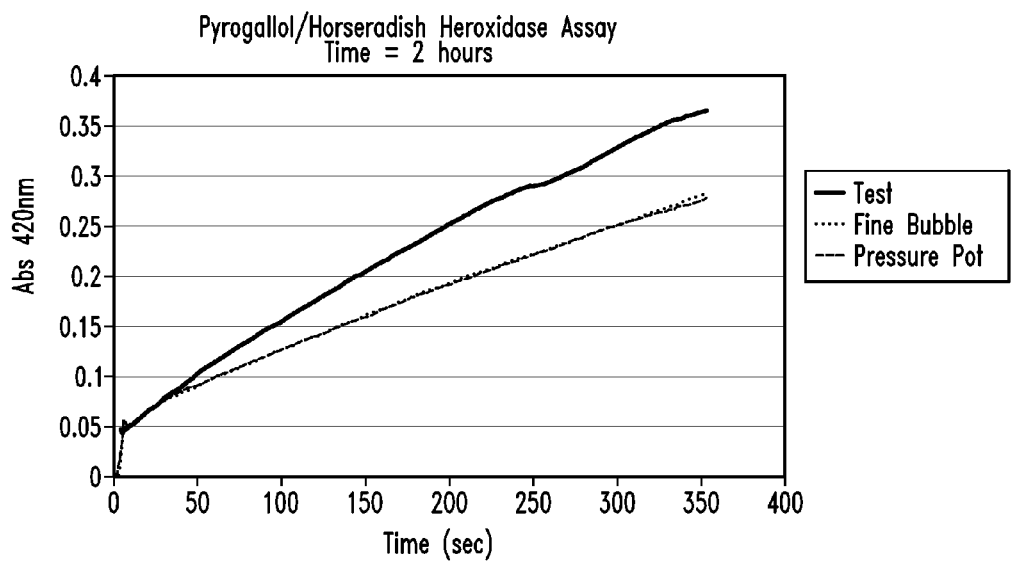
Figure 41:
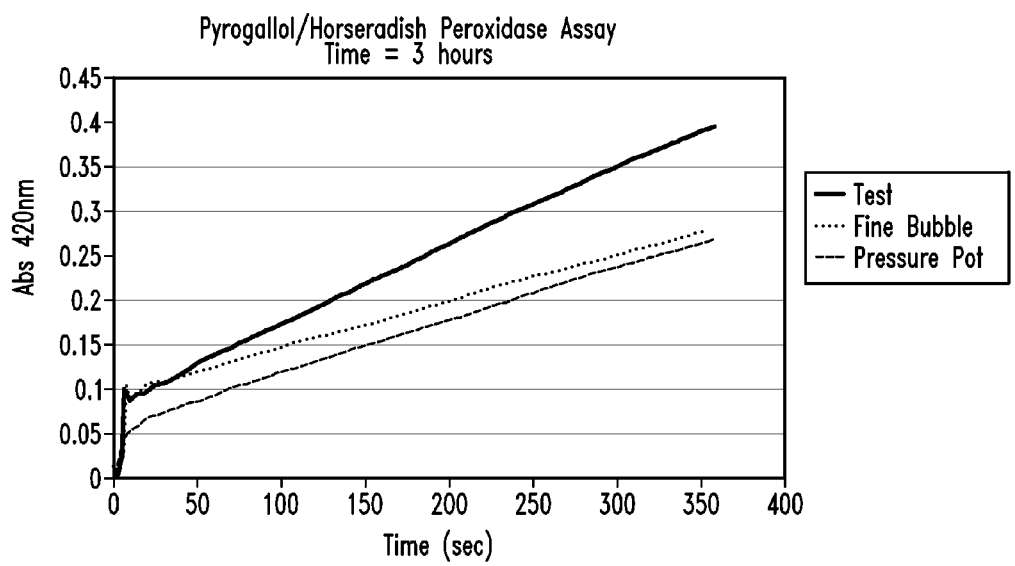
Figure 42:
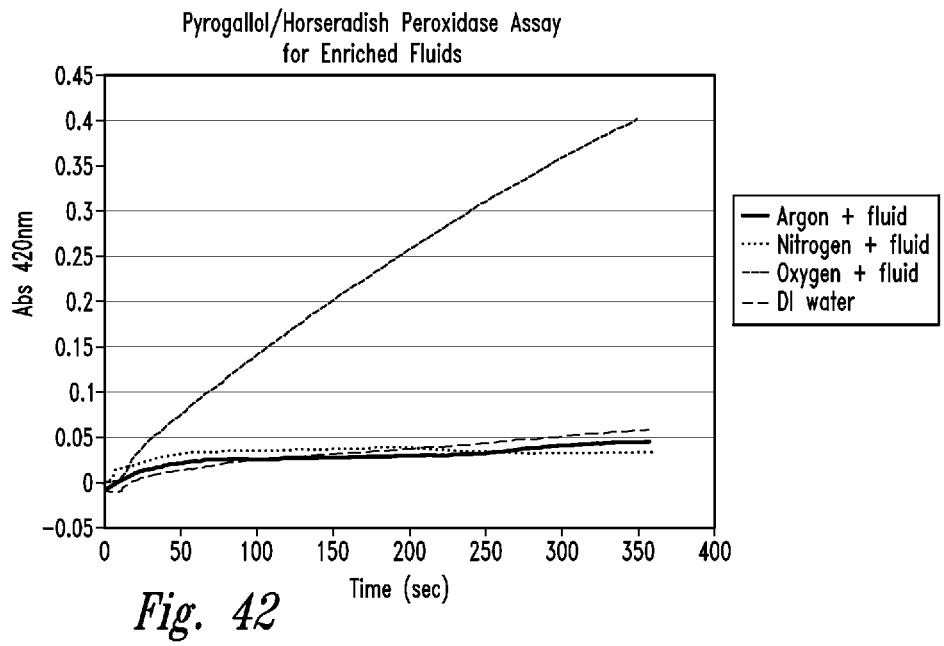
FIG. 42 illustrates pyrogallol/HRP assays as described herein, showing that oxygen is required for the reaction with pyrogallol in the presence of horseradish peroxidase, as inventive fluid enriched with other gases (argon and nitrogen) did not react in the same manner.
Figure 43:
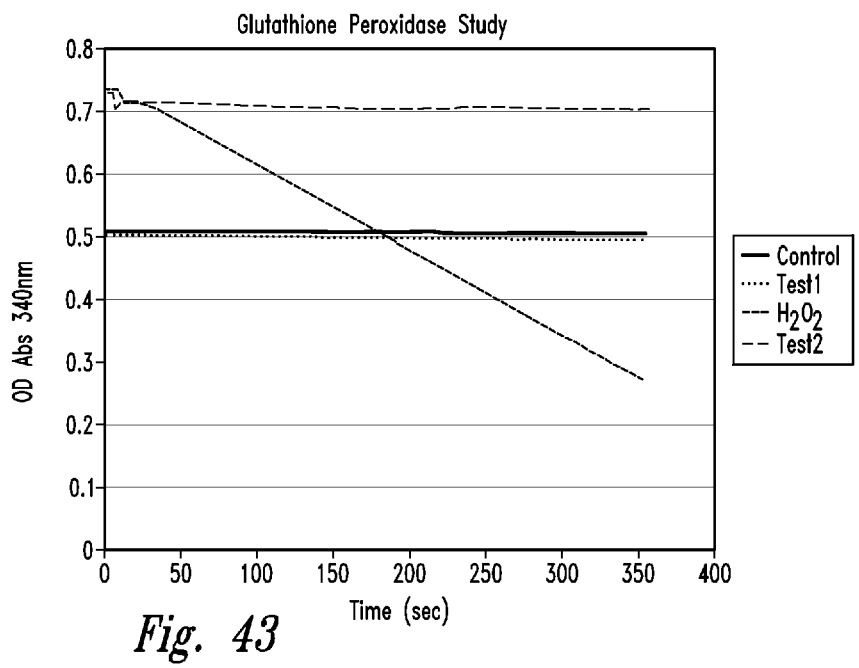
FIG. 43 illustrates the hydrogen peroxide positive control showed a strong reactivity, while none of the other fluids tested reacted with the glutathione.
Figure 44:
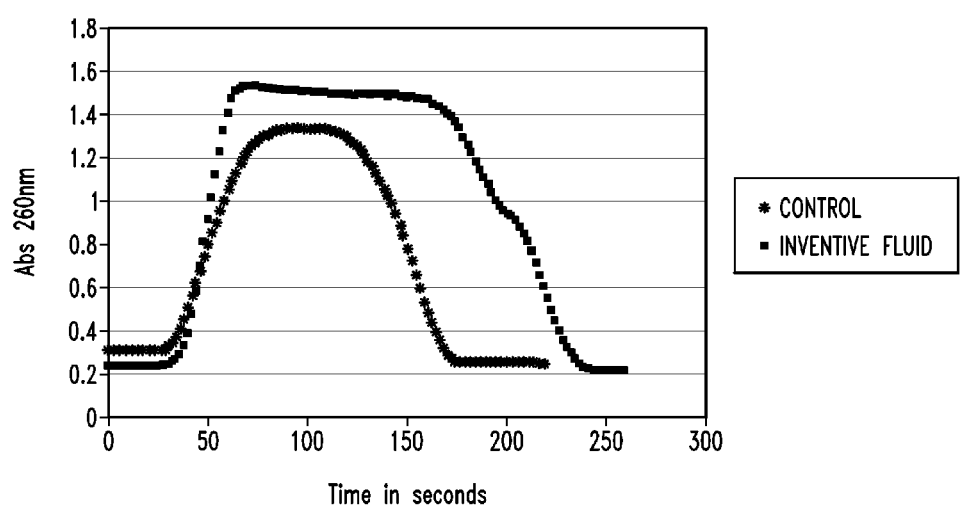
FIG. 44 illustrates T7 DNA shows a conformational change at about 50° C. in the control (deionized water), whereas the DNA in the oxygen-enriched inventive fluid remains intact until about 60° C.
Figure 45A:
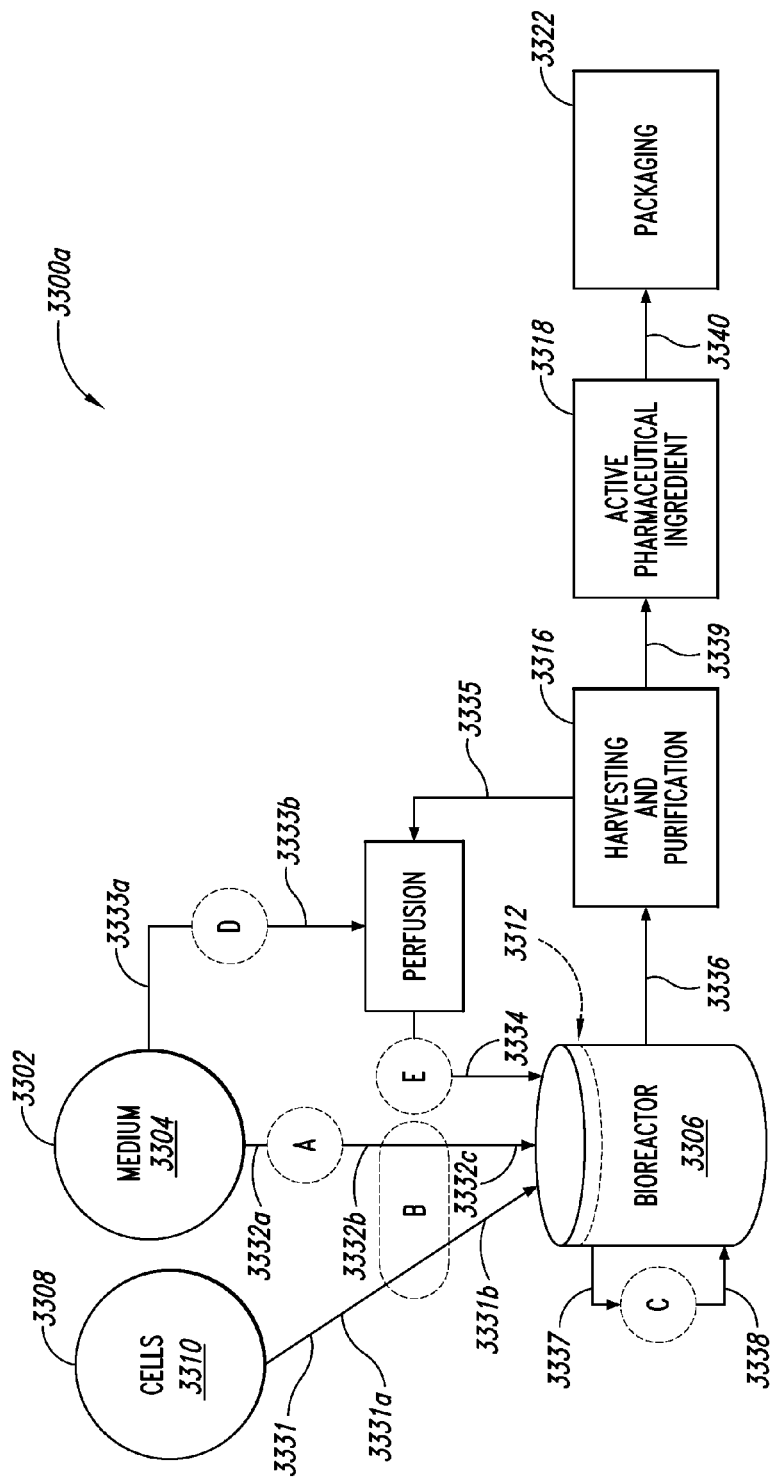
Figure 45B:
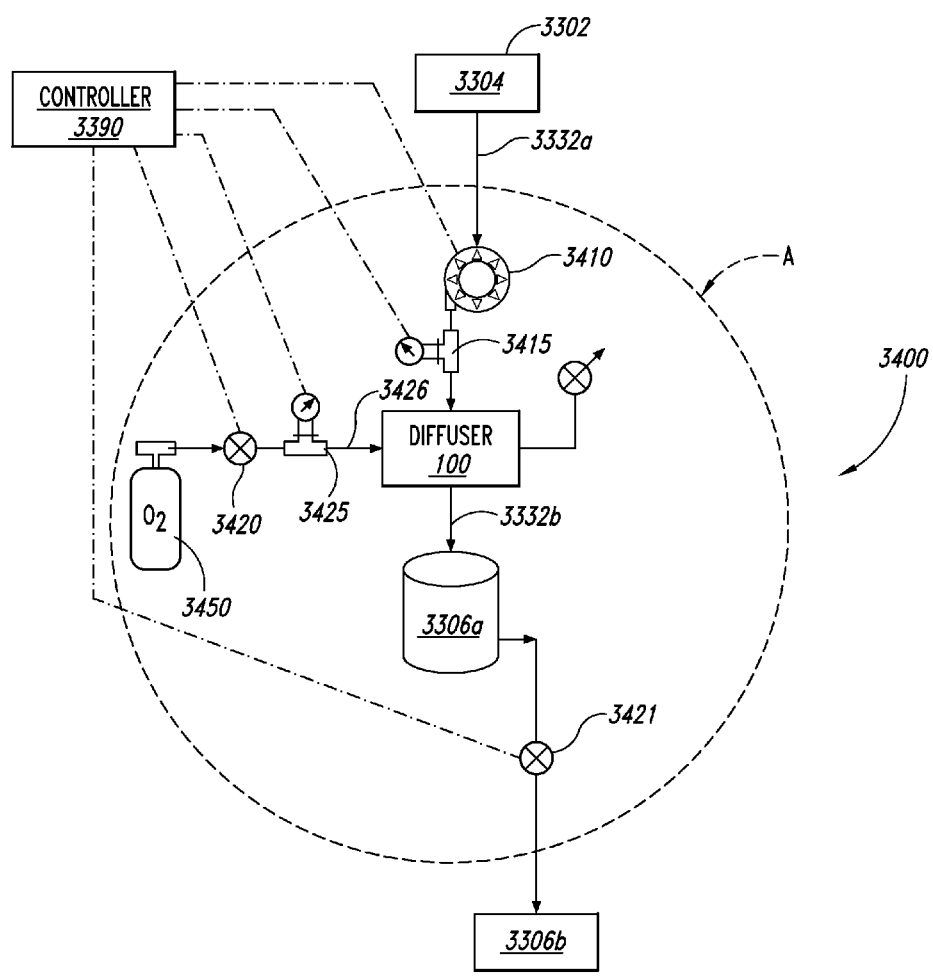
Figure 46:
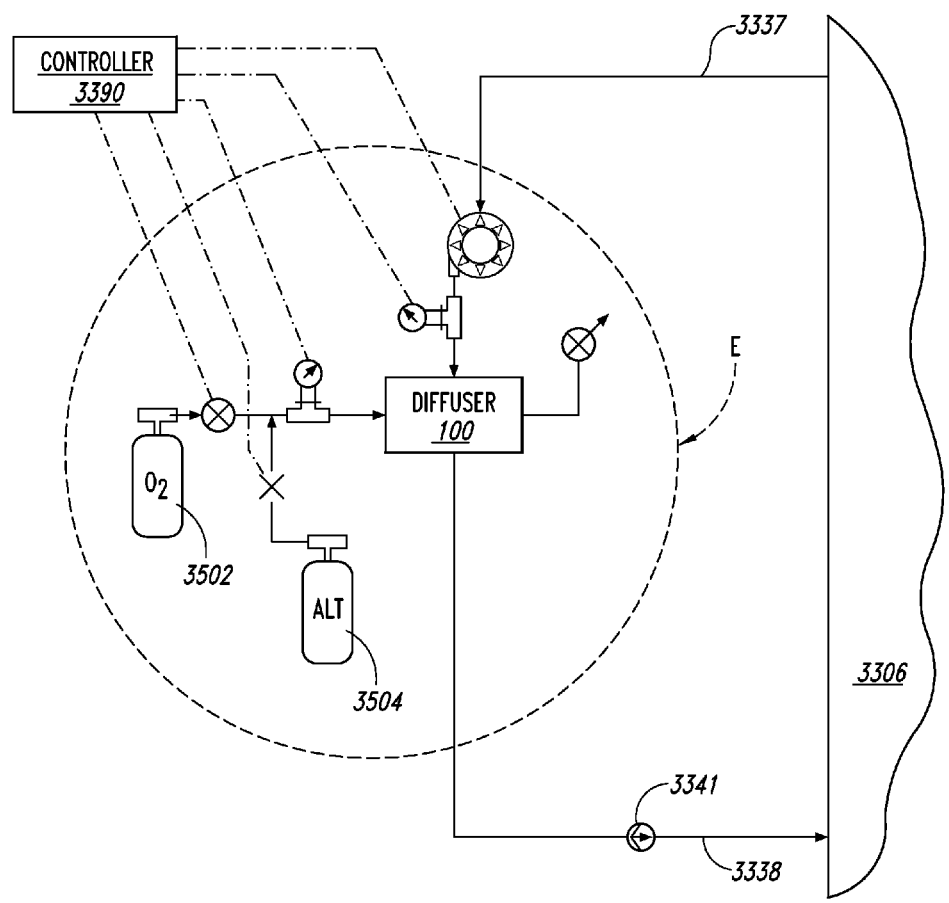
FIG. 46 shows detailed portions of exemplary embodiments of the bioreactor system 3300a of FIGS. 45A and 45B.

Both cytokines increased 24 hours after completion of the exercise trial that was performed after 2 weeks of PW consumption; however, this increase was absent when the subjects had consumed RB (FIG. 6). IFN-α is a cytokine with a broad range of anti-proliferative activities [28]. Similar to IL-6, elevated levels of IFN-α have been linked to fatigue and depression [29,30]. Because IFN-α induces IL-6 [31], these effects of IFN-α may in part be caused indirectly. ENA-78 is a chemokine of the IL-8 family that has similar effects to the ubiquitous IL-8: it attracts neutrophils and thereby promotes inflammation [32]. Elevated ENA-78 levels are found in blood and synovial fluid of rheumatoid arthritis patients and have been associated with disease progression in Crohn's disease, ulcerative colitis, acute appendicitis and chronic pancreatitis [32]. ENA-78 expression has been shown to increase in injured skeletal muscle [33], and the inhibition of plasma ENA-78 by RB therefore is consistent with the protective effective suggested by the myoglobin and CK data.

M-CSF, IFN-α, and ENA-78 showed the same trend: increased plasma levels in the subjects consuming PW at the 24-hour time point that were blunted in subjects receiving RB (data not shown). Absolute M-CSF levels, however, were below the limit of detection in a high proportion of samples.

BDNF. Plasma levels of brain-derived neurotrophic factor (BDNF) were markedly increased 24 hours after the completion of the exercise trial when the study subjects had consumed PW (FIG. 6). RB consumption abolished the post-exercise BDNF peak (FIG. 55).

FIG. 55 shows that RB consumption prevents the rise in BDNF plasma concentration 24 hours after the exercise trial. Data are presented as differences (mean±SEM) between two time points, as indicated by the labels of the x-axis. D0=day before start of beverage consumption, PE=time point immediately prior to starting the endurance exercise, 30 min=30-minute time point of endurance exercise, 60 min=60-minute time point of endurance exercise (end of exercise), 24 h=24 hours after completion of the exercise. P-values was calculated by Wilcoxon signed rank test.

BDNF is a member of the neurotrophin family that is expressed at high levels in the brain and in the peripheral nervous system [34]. BDNF has diverse effects on neuronal cells, including growth, differentiation, and repair [34], and has been suggested to be a pro-angiogenic factor in ischemic tissue [35]. BDNF has also been reported to act as a natural anti-depressant [36,37] and has been associated with the beneficial effects of exercise on memory function and depression [38,39]. In contrast to these positive effects, high BDNF expression in coronary arteries has been found in patients with heart disease and has been suggested to contribute to plaque instability and unstable angina [40]. How to interpret the reduction of BDNF after RB consumption in our study is not clear at present. Of note, however, the study subjects with the highest plasma concentrations of BDNF also had the highest concentrations of ENA-78 (data not shown). One might speculate that post-exercise increases in BDNF, could be linked to the increase of pro-inflammatory factors such as ENA-78 in a similar fashion to the one that has been hypothesized for IL-6, TNF-α and IL-1β [9]. In other words, the presence of factors that counteract a damage response may not be needed if the damaging factors are not released in the first place.

sCD40L. In contrast to IFN-α, ENA-78, and BDNF, all of which showed increased plasma levels 24 hours after exercise, sCD40L showed a difference at earlier time points that was lost later on (FIG. 56). While sCD40L levels increased from the pre-exercise time point to 30 minutes into the exercise when the subjects consumed PW, they decreased when the subjects drank RB (FIG. 56). Absolute plasma concentrations, however, were not significantly different between both experimental conditions (data not shown).

FIG. 56 shows the effect of RB consumption on circulating sCD40L levels. Data are presented as differences (mean±SEM) between two time points, as indicated by the labels of the x-axis. D0=day before start of beverage consumption, PE=time point immediately prior to starting the endurance exercise, 30 min=30-minute time point of endurance exercise, 60 min=60-minute time point of endurance exercise (end of exercise), 24 h=24 hours after completion of the exercise. P-values were calculated by Wilcoxon signed rank test.

In summary of this Example. According to particular aspects, Applicants' Sports Beverage (RB) favorably alters the response to exercise. The study demonstrated promising trends caused by RB consumption. Most importantly, $VO_2$max appeared to be elevated in highly fit subjects, whereas lesser-trained subjects showed a trend towards a lower RPE. At the same time, plasma myoglobin and CK, two markers of muscle damage, were lower across both study subgroups.

References cited in this Example:

1. Mega T L, Ghosh S, German S, Burke L M, Diegel M L, et al. (2010) Anti-Inflammatory Properties of Saline Altered by Controlled Turbulence. submitted.

2. Levine B D (2008) VO2max: what do we know, and what do we still need to know? J Physiol (Lond) 586: 25-34.

3. Nerbonne J M, Kass R S (2005) Molecular physiology of cardiac repolarization. Physiological Reviews 85: 1205-1253.

4. O'Sullivan S B (1984) Perceived exertion. A review. Phys Ther 64: 343-346.

5. Brancaccio P, Lippi G, Maffulli N (2010) Biochemical markers of muscular damage. Clin Chem Lab Med 48: 757-767.

6. Pedersen B K, Akerström T C A, Nielsen A R, Fischer C P (2007) Role of myokines in exercise and metabolism. J Appl Physiol 103: 1093-1098.

7. Ostrowski K, Hermann C, Bangash A, Schjerling P, Nielsen J N, et al. (1998) A trauma-like elevation of plasma cytokines in humans in response to treadmill running. J Physiol (Lond) 513 (Pt 3): 889-894.

8. Pedersen B K, Toft A D (2000) Effects of exercise on lymphocytes and cytokines. Br J Sports Med 34: 246-251.

9. Petersen A M W, Pedersen B K (2006) The role of IL-6 in mediating the anti-inflammatory effects of exercise. J Physiol Pharmacol 57 Suppl 10: 43-51.

10. Fry R W, Morton A R, Keast D (1991) Overtraining in athletes. An update. Sports Med 12: 32-65.

11. Robson-Ansley P J, de Milander L, Collins M, Noakes T D (2004) Acute interleukin-6 administration impairs athletic performance in healthy, trained male runners. Can J Appl Physiol 29: 411-418.

12. Kullo I J, Khaleghi M, Hensrud D D (2007) Markers of inflammation are inversely associated with VO2 max in asymptomatic men. J Appl Physiol 102: 1374-1379.

13. Nehlsen-Cannarella S L, Fagoaga O R, Nieman D C, Henson D A, Butterworth D E, et al. (1997) Carbohydrate and the cytokine response to 2.5 h of running. J Appl Physiol 82: 1662-1667.

14. Geertsema L, Lucas S J, Cotter J D, Hock B, McKenzie J, et al. (2008) The cardiovascular risk factor, soluble CD40 Ligand (CD154), but not soluble CD40, is lowered by ultra-endurance exercise in athletes. Br J Sports Med.

15. Bjornstad H H, Bruvik J, Bjornstad A B, Hjellestad B L, Damas J K, et al. (2008) Exercise training decreases plasma levels of soluble CD40 ligand and P-selectin in patients with chronic heart failure. Eur J Cardiovasc Prey Rehabil 15: 43-48.

16. Varo N, de Lemos J A, Libby P, Morrow D A, Murphy S A, et al. (2003) Soluble CD40L: risk prediction after acute coronary syndromes. Circulation 108: 1049-1052.

17. Suzuki K, Nakaji S, Yamada M, Totsuka M, Sato K, et al. (2002) Systemic inflammatory response to exhaustive exercise. Cytokine kinetics. Exerc Immunol Rev 8: 6-48.

18. Powers S K, Martin D, Dodd S (1993) Exercise-induced hypoxaemia in elite endurance athletes. Incidence, causes and impact on VO2max. Sports Med 16: 14-22.

19. Prefaut C, Durand F, Mucci P, Caillaud C (2000) Exercise-induced arterial hypoxaemia in athletes: a review. Sports Med 30: 47-61.

20. Hoppeler H, Weibel E R (1998) Limits for oxygen and substrate transport in mammals. J Exp Biol 201: 1051-1064.

21. Bouchard C, An P, Rice T, Skinner J S, Wilmore J H, et al. (1999) Familial aggregation of VO(2max) response to exercise training: results from the HERITAGE Family Study. J Appl Physiol 87: 1003-1008.

22. Wehrlin J P, Zuest P, Hallen J, Marti B (2006) Live high-train low for 24 days increases hemoglobin mass and red cell volume in elite endurance athletes. J Appl Physiol 100: 1938-1945.

23. Pollock M L (1973) The quantification of endurance training programs. Exerc Sport Sci Rev 1: 155-188.

24. Fischer C P (2006) Interleukin-6 in acute exercise and training: what is the biological relevance? Exerc Immunol Rev 12: 6-33.

25. Starkie R L, Rolland J, Angus D J, Anderson M J, Febbraio M A (2001) Circulating monocytes are not the source of elevations in plasma IL-6 and TNF-alpha levels after prolonged running. Am J Physiol, Cell Physiol 280: C769-774.

26. Keller C, Steensberg A, Pilegaard H, Osada T, Saltin B, et al. (2001) Transcriptional activation of the IL-6 gene in human contracting skeletal muscle: influence of muscle glycogen content. FASEB J 15: 2748-2750.

27. Steensberg A, van Hall G, Osada T, Sacchetti M, Saltin B, et al. (2000) Production of interleukin-6 in contracting human skeletal muscles can account for the exercise-induced increase in plasma interleukin-6. J Physiol (Lond) 529 Pt 1: 237-242.

28. Schnyder-Candrian S, Strieter R M, Kunkel S L, Walz A (1995) Interferon-alpha and interferon-gamma down-regulate the production of interleukin-8 and ENA-78 in human monocytes. J Leukoc Biol 57: 929-935.

29. Dieperink E, Willenbring M, Ho S B (2000) Neuropsychiatric symptoms associated with hepatitis C and interferon alpha: A review. Am J Psychiatry 157: 867-876.

30. Malik U R, Makower D F, Wadler S (2001) Interferon-mediated fatigue. Cancer 92: 1664-1668.

31. Kennedy R L, Jones T H (1991) Cytokines in endocrinology: their roles in health and in disease. J Endocrinol 129: 167-178.

32. Walz A, Schmutz P, Mueller C, Schnyder-Candrian S (1997) Regulation and function of the CXC chemokine ENA-78 in monocytes and its role in disease. J Leukoc Biol 62: 604-611.

33. Pelosi L, Giacinti C, Nardis C, Borsellino G, Rizzuto E, et al. (2007) Local expression of IGF-1 accelerates muscle regeneration by rapidly modulating inflammatory cytokines and chemokines. FASEB J 21: 1393-1402.

34. Binder D K, Scharfman H E (2004) Brain-derived neurotrophic factor. Growth Factors 22: 123-131.

35. Kermani P, Hempstead B (2007) Brain-derived neurotrophic factor: a newly described mediator of angiogenesis. Trends Cardiovasc Med 17: 140-143.

36. Dwivedi Y (2009) Brain-derived neurotrophic factor: role in depression and suicide. Neuropsychiatric disease and treatment 5: 433-449.

37. Shelton R C (2007) The molecular neurobiology of depression. Psychiatr Clin North Am 30:1-11.

38. Greenberg M E, Xu B, Lu B, Hempstead B L (2009) New insights in the biology of BDNF synthesis and release: implications in CNS function. Journal of Neuroscience 29: 12764-12767.

39. Lafenêtre P, Leske O, Ma-Högemeie Z, Haghikia A, Bichler Z, et al. (2010) Exercise can rescue recognition memory impairment in a model with reduced adult hippocampal neurogenesis. Front Behav Neurosci 3: 34.

40. Ejiri J, Inoue N, Kobayashi S, Shiraki R, Otsui K, et al. (2005) Possible role of brain-derived neurotrophic factor in the pathogenesis of coronary artery disease. Circulation 112: 2114-2120.

Example 5

Beneficial Effects of Electrokinetically Processed Fluids on Human Exercise Performance and/or Recovery Following Intense Exercise Overview:

Exercise-induce muscle damage in humans is widely recognized in the art (see, e.g., Clarkson & Hubal, Am. J. Phys. Med. Rehabil. 81:S52-S69, incorporated by reference herein for its teachings on exercise-induce muscle damage).

According to particular aspects, a blinded (e.g., double-blind, randomized, placebo-controlled, two-arm trial) exercise performance and recovery test is conducted (e.g., to test the effects on extent of muscle fiber micro-injury and recovery), using electrokinetically-altered purified water (test fluid), characterizing that the disclosed electrokinetically-processed fluids have substantial utility for preventing tissue damage and/or enhancing tissue and/or physiological recovery after intense exercise, including preventing muscle and/or tendon damage and/or enhancing/facilitating muscle and/or tendon recovery from exercise (e.g., eccentric exercise), particularly from intense exercise.

Materials:

Electrokinetically-altered purified water (test fluid) processed as previously described (see also US2008/02190088 (now U.S. Pat. No. 7,832,920), US2008/0281001 (now U.S. Pat. No. 7,919,534); US2010/0038244, WO2008/052143, incorporated by reference herein in their entirety for their respective teachings on processing and properties of electrokinetically-altered fluids) is used. The control (negative control fluid) is the corresponding non-electrokinetically-processed purified water.

Preferred route of administration is oral.

Methods:

An art-recognized arm-curl model (see, e.g., Borsa & Sauers, *Med Sci Sports Exerc* 32(5): 891-896, 2000; and Borsa & Liggett *J Athl Train* 33(2): 150-155, 1998; see also McHugh et al., *Sports Med.* 27:157-170, 1999, all incorporated herein by reference for their teachings on eccentric exercise models and related measurements) comprising eccentric exercise to the bicep brachii muscle, is used for inducing skeletal muscle soreness and dysfunction in human subjects using eccentric exercise. The extent of muscle damage and recovery (e.g., the effects on extent of muscle fiber micro-injury and recovery) is determined by analysis of serum biological markers of muscle damage and/or recovery. In particular aspects, the exercise comprises a single bout of enhanced eccentric exercise.

In certain aspects, muscle microinjury is measured. For, example, a concentric/eccentric isokinetic exercise protocol for the biceps brachii muscle is used to induce muscle microinjury (e.g., extent of muscle fiber micro-injury and recovery). As a result of this exercise, subjects will display similar signs and symptoms associated with a mild, sport-related musculotendinous injury. In certain aspects, exercise is performed on a Kin-Com 500-H dynamometer (Chattecx Corp.). The subject (e.g., male and female adults between the ages of 18-35 years are included if they are healthy, non-smoking, and free of nutritional or dietary supplements for a minimum of six weeks) is seated and stabilized the same as for typical force measurements. In certain aspects, the angular velocity is set at $30° s^{-1}$ for concentric actions, and $60° s^{-1}$ for eccentric actions. In particular aspects, the range of motion for the exercise is preset at 45-110° of elbow flexion. Subjects are seated and the elbow aligned with the axis of rotation of the dynamometer. Subjects typically use their nondominant arm for testing. Each subject performs near-maximal concentric and eccentric actions consisting of 10 sets of 5 repetitions with a 30-s recovery period between sets.

In certain aspects, peak force production is measured, for example, using a Kin-Com 500-H dynamometer (Chattecx Corp., Chattanooga, Tenn.). Peak force production is the maximal voluntary isometric force produced during a muscle action. Subjects are typically seated with their nondominant arm placed at their side in 90° elbow flexion, neutral rotation of humerus, and supination of the forearm. In certain aspects, each subject performs a plurality (e.g., three) of maximal voluntary isometric actions held, for example, for 2.5 seconds. The average of the values is recorded as peak force in Newtons (N). The mid-range position is used as the reference angle because of the length-tension relationship. The length-tension relationship is recognized as demonstrating that maximal tension is generated at the mid-range of elbow joint flexion due to optimal available sarcomere cross-bridging. Test/retest reliability is demonstrated.

According to additional aspects, the peak rate of force production is the steepest point on the slope of the force-time curve, and represents the muscle's ability to rapidly generate force or tension ($N s^{-1}$). To calculate this value, raw data from the force-time curve is typically reduced and displayed using an executable program (e.g., Visual Basic 4.0), and test/retest reliability is demonstrated.

In certain aspects, pain perception and muscle dysfunction are assessed as indicators of microinjury. Pain perception is, for example, assessed using an art-recognized visual analog scale (VAS). The use of a VAS is known in the art to be a reliable and valid method of quantifying pain perception. In certain aspects, the VAS consists of a horizontal line (e.g., 10 cm in length) with 0 at the extreme left representing "no pain" and 10 cm on the extreme right representing "pain as bad as it possibly could be" for the biceps brachii muscle. Each subject is then asked to draw a vertical line at the point that most accurately corresponds to their perceived level of pain with active flexion and extension of their involved arm.

In certain aspects, pain-free active range of motion (ROM) is used as a measure of dysfunction. A standard, plastic goniometer may be used to assess ROM for elbow flexion and extension. The goniometer approximats the axis of rotation for the ulnohumeral joint and bisects the humerus and forearm. Extension is typically measured with the subject seated and their arm resting pain free at their side). For flexion, subjects are asked to flex their elbow to the point just before discomfort. This process is repeated, for example, twice for both flexion and extension and the average score is recorded in degrees (°). The criterion measure for pain-free ROM is calculated by subtracting the extension score from the flexion score. Both measures are recorded and analyzed separately before and after the exercise induced microinjury protocol.

For statistical treatment, pre- and post-injury data for pain perception and dysfunction are analyzed, for example, using a one-way ANOVA with repeated measures. Intraclass correlation coefficients (ICCs) and standard error of measurements (SEMS) are calculated for the force measures. Repeated measures are performed for each dependent variable and the ICC is obtained from analysis of variance taking into account the between-subjects mean square, error mean square, trial mean square, number of trials, and number of subjects.

Exemplary detailed study design. A double-blind, randomized, placebo-controlled, two-arm trial is designed to investigate the protective effects of the test beverage (test bev.) compared to control/placebo (non electrokinetically processed) beverage on and muscle function following a single bout of enhanced eccentric exercise. Subjects (e.g., male and female adults between the ages of 18-35 years are included if they are healthy, non-smoking, and free of nutritional or dietary supplements for a minimum of six weeks) are randomly assigned to either a test beverage group (n=20) or placebo control group (n=20). The effects of the test bev. are compared to the placebo control. Subjects are required to complete a 21-day supplement trial spanning pre-supplement baseline testing, a controlled water beverage supplementation regimen, pre-exercise baseline testing, eccentric arm exercise to induce muscle damage, and planned follow-up post-exercise data collection time points. A "between subjects two-arm trial design" is preferably chosen over a "within-subjects cross-over design" in order to prevent the influence of confounds due to repeated bout effects. The repeated bout effect is a phenomenon characterized by less muscle damage, inflammation, delayed-onset muscle soreness (DOMS) and strength deficits after the second of 2 separate eccentric exercise bouts performed in close proximity usually within days to weeks.

Study population. Inclusion/Exclusion criteria: male and female adults between the ages of 18-35 years are included if they are healthy, non-smoking, and free of nutritional or dietary supplements for a minimum of six weeks. Supplements include but are not limited to ephedra, yohimbine, pro-hormones, creatine or anabolics. Subjects are excluded if they have been involved in a regular weight-training program within the last six weeks, have a prior history of injury to the neck, shoulder or elbow region of the non-dominant arm, recent history of a bacterial infection or current reported use of anti-inflammatory medication within the last 6 weeks.

Test article and dosing. The test beverage and placebo are packaged in 500-ml plastic bottles, and subjects are instructed to consume a prescribed dose of the beverage (bottles/day) based on the following body weight categories. For example, <130 lb=2 bottles/day; 130-160 lb=3 b/d; 160-190 lb=4 b/d; 190-220 lb=5 b/d; >220 lb=6 b/d.

Blood biomarker measures. Assays are used to track serum levels for biomarkers of muscle damage (e.g., creatine kinase (CK)]) and inflammation (C-reactive protein (CRP), interleukin-6 (IL-6), tumor necrosis factor alpha (TNF-α)) and/or other cytokines or markers as appropriate.

Functional measures. Isometric muscle strength (peak force production) is used as a measure of overall arm function. Symptoms and impairments are measured using pressure pain ratings (algometer) and self-report functional questionnaires.

Blood collection. Blood samples are collected via venipuncture in the early morning (between 7-10 am) after a 10-hr fast. Phlebotomy-trained personnel complete all blood draws. After separation, all specimens are aliquoted into the appropriate number of cryovials based on the proposed number of assays. Blood is taken from the antecubital vein and collected into two 10 mL Vacutainer® tubes containing ethylenediaminetetraacetic acid ($K_3$EDTA; 8.4 mg/Vacutainer®) or into two 10 mL serum collection tubes. Since various biochemical assays require different blood collection procedures, two 10 mL Vacutainer® containing either sodium citrate (3.2%, 0.109M) and sodium heparin are collected. Blood is centrifuged at 4° C. at 1500×g for five minutes. For some analyses, plasma is allocated to storage tubes containing 100 μM butylated hydroxytoluene (BHT), Trolox (100 μM) and 100 μM diethylenetriamine pentaacetic acid (DTPA). DTPA serves as a metal chelator, and BHT acts as a chain-breaking antioxidant to prevent lipid peroxidation ex vivo. Samples are stored immediately at −80° C. in multiple aliquots (6 to 8). Samples stored in multiple aliquots (~0.25 mL) are thawed only once and immediately analyzed for a specific biomarker (samples subjected to one freeze-thaw cycle, may show increases in baseline lipid peroxidation products). Cryovial labels are color coded by study and include the subject ID number, date, visit number (specific per study), and cryovial number.

Each sample is logged into an Excel spreadsheet by a lab technician and frozen at −80° C. in locked freezers connected to an emergency power supply and an alarm system.

Visit 1 (Baseline measurements, day 0). Report to lab at assigned meeting time. A signed informed consent is obtained prior to any testing. The following procedures are performed: brief medical screen (height, weight, pulse, blood pressure and body temperature), blood draw, subjective evaluation of arm function, muscle point tenderness, and isometric strength measures. Body temperature is measured to ensure that the subject is not running a fever. Subjects are instructed to maintain current activity levels and not to initiate a resistance-training or weight-loss program for the duration of the study. Subjects are randomly assigned to a group (test beverage/placebo) and instructed to consume the test beverage (or placebo), which is dispensed for the next 18 days. A pre-exercise visit is scheduled for 10 days later. All pre-exercise and follow-up measurements are compared with baseline measures.

Visit 2 (pre-exercise measurements, eccentric exercise protocol, day 10). Report to lab at assigned meeting time. The following procedures are performed: brief medical screen (height, weight, pulse, blood pressure and body temperature), blood draw, subjective evaluation of arm function, muscle point tenderness, and isometric strength measures. Subjects then undergo a standardized single bout of eccentric resistance exercise to the non-dominant biceps brachii muscle. A standard arm-curl machine (Cybex International, Inc., Medway, Mass.) is used for the eccentric exercise protocol. Exercise weights for each subject re determined by establishing their one repetition maximum (1-RM) concentric or shortening contraction. The 1-RM is determined by having the subject perform a concentric arm curl against a low resistance with continued repetitions being performed with weight being incrementally added until a 1-RM is reached. Each subject then performs five sets of ten repetitions of lengthening contractions on the arm curl machine using a weight equivalent to 140% of their 1-RM. Each repetition takes 4-6 seconds to ensure maximal tension is being applied to the muscle. Subjects are given a one-minute rest period between sets. Exercise is not performed in the usual way (concentric)—meaning shortening of muscles during contraction. It is rather performed eccentrically—lengthening the muscle while still developing tension (overload). The angular velocity will be set at 45°/sec for concentric and 60°/sec for eccentric actions. Subjects will be given a one-minute rest period between sets. The exercise session takes less than 10 minutes.

Visits 3-5 are scheduled for follow-up measurements.

Precautionary measures are taken to prevent and monitor adverse reactions to the exercise protocol. Follow-up visits (e.g., day 19, 20 and 21) are scheduled post-exercise.

Data analysis. Data are analyzed using a two way ANOVA with repeated measures on the second factor (time). Outcome measures are analyzed using a two (group) by four (time) ANOVA. Statistical significance is set at $p<0.05$. If significant interactions occur, the Tukey post-hoc test is used to reveal where the differences occur. All data analyses are performed using SPSS™ for Windows 16.0 (SPSS, Inc., Chicago, Ill.).

Results:

According to particular aspects, the electrokinetically-processed fluids have substantial utility for preventing or alleviating/reducing tissue damage and/or enhancing tissue and/or physiological recovery after intense exercise, including preventing muscle damage and/or enhancing/facilitating muscle recovery from exercise (e.g., eccentric exercise), particularly from intense exercise.

In certain embodimens, the electrokinetically-processed fluids have substantial utility for preventing or alleviating/reducing the extent of muscle fiber micro-injury, and/or enhancing recovery thereof.

According to particular aspects, the electrokinetically-processed fluids have substantial utility for reducing biomarkers of exercise-induced muscle injury (e.g., creatine kinase (CK)).

According to additional aspects, the electrokinetically-processed fluids have substantial utility for reducing subjective ratings of muscle soreness.

According to yet additional aspects, the electrokinetically-processed fluids have substantial utility for preserving muscle contractile function (e.g., maximal force, joint ROM).

According to yet additional aspects, the electrokinetically-processed fluids have substantial utility for preventing and/or ameliorating/reducing exercise-induced tendon damage and/or enhancing/facilitating tendon recovery from exercise and/or exercise-induced damage (e.g., eccentric exercise, tendinosis, tendonitis, tenosynovitis), particularly from intense exercise, and/or reducing exercise-induced tendon-related pain and/or swelling. In certain aspects at least one of peroneal tendon, flexor tendon, Achilles tendon is treated.

According to yet additional aspects, the electrokinetically-processed fluids have substantial utility for preventing and/or ameliorating/reducing and/or enhancing recovery from tendon strain associated with chronic, repetitive movement, comprising administration, to a subject in need thereof, a electrokinetically-altered sports beverage composition as disclosed herein in an amount sufficient to prevent and/or ameliorate and/or enhance recovery from tendon strain associated with chronic, repetitive movement.

According to further aspects, and as demonstrated in Example 3 above and in this Example 4, the electrokinetically-processed fluids have substantial utility for improving exercise performance.

The invention claimed is:

1. A method for enhancing exercise performance and/or recovery time, comprising administering to a subject in need thereof, an ionic aqueous solution of charge-stabilized oxygen-containing nanobubbles having an average diameter of less than 100 nanometers in an amount sufficient to provide for enhancing exercise performance and/or recovery time, wherein the ionic aqueous solution comprises oxygen in an amount of at least 15 ppm at ambient temperature and, atmospheric pressure, wherein the exercise comprises at least one of intense exercise, eccentric exercise, exercise in elevated ambient temperature, repetitive exercise, aerobic exercise, and/or high altitude exercise, and wherein enhancing exercise performance and/or recovery time comprises reducing exercise-induced increases of plasma inflammatory cytokine levels in the subject or comprises ameliorating exercise-mediated muscle and/or tendon damage and enhancing muscle and/or tendon recovery therefrom.

2. The method of claim 1, wherein the exercise-induced plasma inflammatory cytokine is one selected from the group consisting of interferon-alpha (IFN-alpha), epithelial neutrophil activating protein 78 (ENA-78), and brain-derived neurotrophic factor (BDNF).

3. The method of claim 1, wherein the ionic aqueous solution comprises oxygen in an amount selected from the group consisting of at least 25 ppm, at least 30 ppm, at least 40 ppm, at least 50 ppm, and at least 60 ppm oxygen at ambient temperature and, atmospheric pressure.

4. The method of claim 1, wherein the ionic aqueous solution comprises a saline solution.

5. The method of any one of claims 1, 2, and 3-4, wherein the ionic aqueous solution comprises oral administration of aqueous solution or sports beverage.

6. The method of claim 5, wherein the sports beverage comprises a sugar, carbohydrate, electrolyte or other sports beverage ingredient.

7. The method of claim 6, wherein the ionic aqueous solution comprises at least one positively-charged ion selected from the group consisting of: alkali metal based salts; alkali metal based salts of Li+, Na+, K+, Rb+, and Cs+; alkaline earth based salts; alkaline earth based salts of Mg++ and Ca++; and transition metal-based positive ions of Cr, Fe, Co, Ni, Cu, and Zn.

* * * * *